US008278063B2

(12) United States Patent
Pandey et al.

(10) Patent No.: US 8,278,063 B2
(45) Date of Patent: Oct. 2, 2012

(54) METHODS FOR DEGRADING TOXIC COMPOUNDS

(75) Inventors: Gunjan Pandey, Florey (AU); Chris M. Coppin, Ngunnawal (AU); Susan J. Dorrian, Fraser (AU); Robyn Russell, Wanniassa (AU); John Oakeshott, Wanniassa (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 111 days.

(21) Appl. No.: 12/666,601

(22) PCT Filed: Jun. 27, 2008

(86) PCT No.: PCT/AU2008/000948
§ 371 (c)(1),
(2), (4) Date: Apr. 27, 2010

(87) PCT Pub. No.: WO2009/003222
PCT Pub. Date: Jan. 8, 2009

(65) Prior Publication Data
US 2010/0279380 A1 Nov. 4, 2010

Related U.S. Application Data

(60) Provisional application No. 60/947,147, filed on Jun. 29, 2007.

(30) Foreign Application Priority Data

Jun. 29, 2007 (AU) ................................ 2007903522

(51) Int. Cl.
| C12N 1/20 | (2006.01) |
| C12N 9/16 | (2006.01) |
| C12N 11/02 | (2006.01) |
| C02F 3/34 | (2006.01) |
| C12Q 1/44 | (2006.01) |
| C07H 21/04 | (2006.01) |

(52) U.S. Cl. ........ 435/19; 435/177; 435/196; 435/252.1; 435/252.33; 435/262; 435/320.1; 536/23.2

(58) Field of Classification Search ........................ None
See application file for complete search history.

(56) References Cited

U.S. PATENT DOCUMENTS

| 4,945,050 | A | 7/1990 | Sanford et al. |
| 5,004,863 | A | 4/1991 | Umbeck |
| 5,014,310 | A | 5/1991 | Walker et al. |
| 5,141,131 | A | 8/1992 | Miller, Jr. et al. |
| 5,159,135 | A | 10/1992 | Umbeck |
| 5,177,010 | A | 1/1993 | Goldman et al. |
| 5,362,865 | A | 11/1994 | Austin |
| 5,384,253 | A | 1/1995 | Krzyzek et al. |
| 5,416,011 | A | 5/1995 | Hinchee et al. |
| 5,451,513 | A | 9/1995 | Maliga et al. |
| 5,463,174 | A | 10/1995 | Moloney et al. |
| 5,472,869 | A | 12/1995 | Krzyzek et al. |
| 5,518,908 | A | 5/1996 | Corbin et al. |
| 5,545,813 | A | 8/1996 | Piper et al. |
| 5,569,834 | A | 10/1996 | Hinchee et al. |
| 5,589,617 | A | 12/1996 | Nehra et al. |
| 5,792,924 | A | 8/1998 | Yoder et al. |
| 5,859,347 | A | 1/1999 | Brown et al. |
| 5,877,402 | A | 3/1999 | Maliga et al. |
| 5,932,479 | A | 8/1999 | Daniell et al. |
| 6,100,447 | A | 8/2000 | Wu et al. |
| 6,541,257 | B2 | 4/2003 | Lemaux et al. |
| 2004/0029129 | A1 | 2/2004 | Wang et al. |
| 2007/0118916 | A1 | 5/2007 | Puzio et al. |

FOREIGN PATENT DOCUMENTS

| AU | 667939 | 1/1994 |
| CA | 2092588 | 9/1994 |
| WO | 8402913 | 8/1984 |
| WO | 8706614 | 11/1987 |
| WO | 9209696 | 6/1992 |
| WO | 9321335 | 10/1993 |
| WO | 9419930 | 9/1994 |
| WO | 9748814 | 12/1997 |
| WO | 9905265 | 2/1999 |
| WO | 9914314 | 3/1999 |
| WO | 0064539 | 11/2000 |
| WO | 2004112482 | 12/2004 |
| WO | 2005026269 | 3/2005 |

OTHER PUBLICATIONS

Pandey et al. Cloning and biochemical characterization of novel carbendazim (methyl-1H-benzimidazol-2-ylcarbamate-hydrolyzing esterase from the newly isolated Nocadioides sp. strain SG-4G and its potential for use in enzymatic bioremediation. Appl. Envirn. Microbiol. May 2010, vol. 76 (9) pp. 2940-2945.*
GenBank: AB177893, Nov. 18, 2004 *Ralstonia solanacearum* hpx1 gene for hypothetical protein, complete cds, strain:RS1000 is 61.12% identical to SEQ ID No. 2.
GenBank: AF005024 Mar. 23, 2007 Nocardioides nitrophenolicus strain NSP 41 16S ribosomal RNA gene, partial sequence is 99.6% identical to SEQ ID No. 4.
Harada, et al., Isolation and characterization of microorganisms capable of hydrolysing the herbicide mefenacet, Soil Biology and Biochemistry, vol. 38, Issue 1, Jan. 2006, pp. 173-179.
Kubota, et al., Nocardioides aromaticivorans sp. nov., a dibenzofuran-degrading bacterium isolated from dioxin-polluted environments, Syst Appl Microbiol. Mar. 2005;28(2):165-74.
STN File CAPLUS Accession No. 1993:535253, & Kozyreva, L.P. et al. Mikrobiologiya (1993), 62(1), p. 110-119. (with English Abstract).

(Continued)

*Primary Examiner* — Nashaat Nashed
(74) *Attorney, Agent, or Firm* — Carol L. Francis; Bozicevic, Field & Francis LLP

(57) ABSTRACT

The invention relates to bacteria, bacterial extracts, supernatants obtained from the culturing of said bacteria, polypeptides and compositions for degrading benzimidazole carbamate fungicides, carbanilate fungicides, sulfonamide herbicides, thioamide herbicides and/or synthetic pyrethroid insecticides. In particular, the invention relates to the identification of *Nocardioides* sp. which degrades benzimidazole carbamate fungicides, carbanilate fungicides, sulfonamide herbicides, thioamide herbicides and/or synthetic pyrethroid insecticides.

31 Claims, 13 Drawing Sheets

OTHER PUBLICATIONS

Figure 1A:
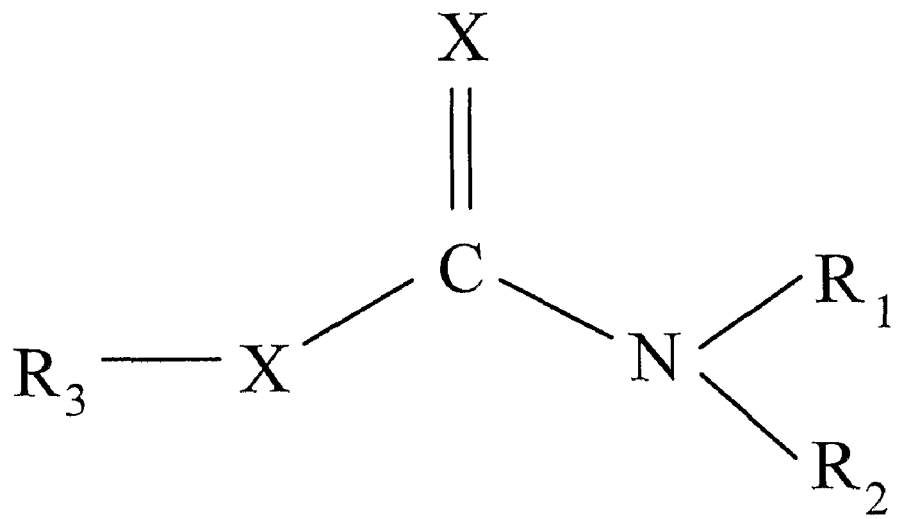

Topp, et al., Characterization of S-Triazine Herbicide Metabolism by a Nocardioides sp. Isolated from Agricultural Soils, Applied and Environmental Microbiology, Aug. 2000, p. 3134-3141, vol. 66, No. 8.

Abdullah, et al. (1986) "Efficient Plant Regeneration from Rice Protoplasts Through Somatic Embryogenesis" Nature Biotechnology 4:1087-1090.

Bornscheuer (2002) "Microbial Carboxyl Esterases: Classification, Properties and Application in Biocatalysis" FEMS Microbiol. Rev. 26(1):73-81.

Cheng, et al. (1996) "Production of Fertile Transgenic Peanut (*Arachis Hypogaea* L.) Plants Using Agrobacterium Tumefaciens" Plant Cell Reports 15:653-657.

Derbyshire (1987) "Purification and Characterization of an N-Methylcarbamate Pesticide Hydrolyzing Enzyme" J. Agric. Food Chem. 35:871-877.

Grant, et al. (1995) "Transformation of Peas (*Pisum sativum* L.) Using immature Cotyledons" Plant Cell Reports 15:254-258.

Harayama (1998) "Artificial Evolution by DNA Shuffling" Trends Biotechnol. 16(2):76-82.

Hayatsu, et al. (2001) "Purification and characterization of Carbaryl Hydrolase from *Arthrobacter* sp. RC100" FEMS Microbiol. Lett. 201(1):99-103.

Huang, et al. (2005) "Development of Optically Pure Pyrethroid-Like Fluorescent Substrates for Carboxylesterases" Chem. Res. Toxicol. 18(3):516-527.

Jing-Liang, et al. (2006) "Isolation and Characterization of a Carbendazim-Degrading *Rhodococcus* sp. djl-6" Curr Microbiol. 53(1):72-76.

Karns, et al. (1986) "Metabolism of Carbofuran by a Pure Bacterial Culture" Pestic. Biochem. Physiol. 25:211-217.

Karns, et al. (1991) "Carbofuran Hydrolase—Purification and Properties" J. Agric. Food Chem. 39:1004-1008.

Koziel, et al. (1996) "Optimizing Expression of Transgenes with an Emphasis on Post-transcriptional Events" Plant Mol. Biol. 32(1-2):393-405.

Lejuene, et al. "Nerve Agents Degraded by Enzymatic Foams" (1998) Nature 395:27-28.

Lu, et al. (1993) "High Efficiency Retroviral Mediated Gene Transduction into Single Isolated Immature and Replatable CD34(3+) Hematopoietic Stem/Progenitor Cells from Human Umbilical Cord Blood" J. Exp. Med. 178(6):2089-2096.

Needleman and Wunsch (1970) "A General Method Applicable to the Search for Similarities in the Amino Acid Sequence of Two Proteins" J. Mol Biol. 48:443-453.

Petrikovics, et al. (2000) "Long-Circulating Liposomes Encapsulating Organophosphorus Acid Anhydrolase in Diisopropyfluorophosphate Antagonism" Toxicology Science 57:16-21.

Petrikovics et al. (2000) "In Vitro Studies on Sterically Stabilized Liposomes (SL) as Enzyme Carriers in Organophosphorus (OP) Antagonism" Drug Delivery 7:83-89.

Tomasek (1989) "Cloning of a Carbofuran Hydrolase Gene From *Achromobacter* sp. Strain WM111 and Its Expression in Gram-Negative Bacteria" J. Bacteriol. 171(7):4038-4044.

Topp, et al. (1993) "Isolation and Characterization of an N-Methylcarbamate Insecticide-Degrading Methylotrophic Bacterium" Appl. Environ. Microbiol. 59(10):3339-3349.

Toriyama, et al. (1986) "Haploid and Diploid Plant Regeneration from Protoplasts of Anther Callus in Rice" Theor. Appl. Genet. 73:16-19.

Wagner, et al. (1992) "Coupling of Adenovirus to Transferrin-Polylysine/DNA Complexes Greatly Enhances Receptor-Mediated Gene Delivery and Expression of Transfected Genes" Proc. Natl. Acad. Sci, USA 89 (13):6099-6103.

Zhang, et al. (2005) "Isolation and Characterization of a New Carbendazim-Degrading *Ralstonia* sp. Strain" World J. Microbiol. Biotechnol. 21:265-269.

Database: Uniprot Accession No. A1VIR9 SubName: Full=Putative Esterase dated Feb. 6, 2007.

GenBank Accession No. AB177893, "*Ralstonia Solanacearum* hpx1 Gene for Hypothetical Protein, Complete cds, Strain:RS1000" dated Nov. 18, 2004.

Pandey, et al. (2010) "Cloning and Biochemical Characterization of a Novel Carbendazim (Methyl-1H-Benzimidazol-2-Ylcarbamate)-Hydrolyzing Esterase from the Newly Isolated Nocardioides sp. Strain SG-4G and Its Potential for Use in Enzymatic Bioremediation" Applied and Environmental Microbiology 76(9):2940-2945.

Cousin, et al., (1997) "The αβ fold family of proteins database and the cholinesterase gene server ESTHER" Nucleic Acids Research, 25(1):143-146.

Hotelier, et al., (2004) "ESTHER, the database of the αβ-hydrolase fold superfamily of proteins" Nucleic Acids Research, 32:D145-D147.

Satoh, et al., (2002) "Current Progress on Esterases: from Molecular Structure to Function" Drug Metabolism and Disposition, 30(5):488-493.

* cited by examiner

MBC　　　　　2-AB　　　　　2-HB

Figure 6

Figure 6 (continued)

```
                 230       240       250       260       270       280       290       300       310       320
                 ....|....|....|....|....|....|....|....|....|....|....|....|....|....|....|....|....|....|....|....|
MheI             EMPLLLAGGSAVKQ-RVYILAD------GWDPSPRYFAKLYD-------GKPGWQVVKFPCGHDVMVDMPNELAEKLAALG---------------------
ZP_02187615.1    SEKLHLSGAGDRIAD-RVYIRAG-----GYPNPAFDAALEMAR-------ADSRFRCHVVDCGHDIMVDAPDELTRILLESA---------------------
YP_001415909.1   TDPAVLTGAWMEIKV-LAYACTL-----REPAPDERDIAAQLA-------KDPRETIRELTSGHDAMIDVPQDVADLLLACAEAARTVEATCAAPTGSPS
ZP_02122769.1    ESPLRLKGPLGNGLP-RTYVDCT-----NPSYPPLDGVKDWVR-------RQPGWDWAALATGHDAMVSTPDALARLLVELATPRP----------------
YP_001772634.1   ESPLVLRNPVGNGLP-RTYVDCT-----APTYPALDGVKEWVR-------RQPGWRFADLATGHDAMVSAPEATARLLLDCAGA-----------------
YP_001262405.1   CEPVELTGAWEGIAR-KTYVRATGWA--GYAALGFDP-MAKVE-------AGAGWSTIDVDCGHEVALDAPARLADMLNA--------------------
YP_980468.1      QAPLDFDVQRVAAVP-RTFVSCT-----EPALATIAPSRLRAKDPKFWDGAWLPGASTIELQTGHDPMVSEPAALVRILLGCGA----------------
YP_785170.1      TTPLTLQHPIGNGRP-RTYIHCT-----QPELPVLEQSRKLVK-------SQQGWNWVDLAAPHEAHITHPALLTEVLLGLS-----------------
YP_547141.1      QAPLNEDMQRVAAVP-RTYVSCT-----QPALATIDPSRLRARDPKEWDGAWLPNSKFVEIQTGHDPMISDPHALTKILLDCAA---------------
NP_628561.1      RQPVRLGNPAADAIP-RTHIHNVG----AMP-TGITRRPVPPI--QPNGTAAQVWELPTGHDCMITMPTELSELLLKLP--------------------
ZP_02892931.1    QEKFYLKNPIGNGVP-RIYVDCV-----AHSFAPLAKLKKDIR-------AQPGWIWRELDARHDPMVTEPHLLDEFLQSI-----------------
NP_773254.1      ETKLKLEHG-DPPMP-RSYIYCTR----IPPGDVFGQFAKHTK-------NEDGWRYFELDASHAPNVTAPALMAVLNEIAA---------------
LQPIRLAGGADGVRR-RDYAYALN----WPGQSPMRRSYERVR-------DDPAWTVHELDGKHNLMRDNPDDLLRILLAAAAH---------------
ZP_001071298.1   LQPIRLAGGAGVRR-RDYAYALD-----WPGESPLRRSYERVR-------DDPAWTVHELDGKHNLMRDNADDLLRILLAAAAH----------------
YP_640176.1      TQSVEIKNSKQLIP-HIYVEVKDNPEHWPMTPIFLESAKKAR-------DRKWEVFSIEVGGHWVMETNPEALVRILNQCVEVV----------------
NP_980782.1      EQPVP-DAPAPGALP-GTYIHCTA----APAYFDDVARR-----------AADDGLAVVTLDAGHMALLTHADEVSATLLELAQEAPR------------
YP_119481.1      VEAVRFTGEEAKIPR-RIYVYANG----WQP-TPFAKFADAVQ-------DDPAWEYHEAEASHNVMADQPEQLLRIVLGCA-----------------
YP_498129.1      LQPLRLRGDLNGFRR-RIFVYALD----WPGESPLRPSYDRVR-------DDPTWICHELDGRHNLMRDRPADLIRLILSASQS--------------
YP_954166.1      TQSVEIKNSKAQCIP-HIYVEVKDNPEHWPMTSIFLESAKKAR-------DRKWEVFSIEVGGHWVMETNPEALVRILNQSVEVI---------------
ZP_02253708.1    TQSVEIKNSKAQCIP-HIYVEVKDNPEHWPMTSIFLESAKKAR-------DRKWEIFSIEVGGHWVMETNPEALVRILNQSVEVI---------------
ZP_085728.1      REPLPFDGERWARLR-RSFIDCN-----APAYPTISAMRERVR-------QLPGFDVREIATGHCPMVSEPAALVAHLLAIAAT---------------
YP_001793382.1   TQAVEIKNPIVQHIP-HIYVEIQDHPEYWPMTPIFLASAKKAR-------DRKWNVFSIESGGHWIMETNPEALVHILNKCVE---------------
YP_001376340.1   TDAISLSKNPAEMEIGKSYVLCVEDT--ALPHS-MPWHPRLSE-------KLGLFRLVTTGGSHEACFTDPEGLADAILRAGRD---------------
ZP_01014266.1    TDAIKLRTNPAEMTIAKSYINCTEDT--ALPHG-LPWHPRLSS-------KLGLERLVQVPGSHELCFSEPARLAQAIMDAGRD---------------
YP_001239781.1   TDAIKLTNPAEMTIAKSYINCTEDT--ALPHS-LPWHPRLSG-------KLGLFRLVQVPGSHELCFSDPARLAQAIMDAGRD---------------
YP_001205313.1   QQELKISEENFGAID-RIYIETTLDR--AIPIDFQRRMNTETP-------CKKIITLEADHSPFFSKVSELVLNLNELS------------------
ZP_02581895.1    TDKVPLKS-FDKLQIPKTYLNAQADV--AMPEGQYAWFPREAE-------RLFPCRVHMSGSHQVMFSNPAGLAEKIIQAGRD---------------
YP_001890475.1   TERLDLRR-FYRSTLPMHYIDAVDDR--ALPRG-LDREAMIE--------RLKNVRVHRVRGGHEVLFTDPAGIAAVIVEAGVS--------------
YP_886169.1      HDRLDLKK-FYTLNIPKSYLNCTEDQ--ALPAG-FWHPKMSN--------RLGEFKLVEMGGSHEAMFTRQELATKIIEASHD--------------
YP_046113.1      TVPATLTG-ASDTVP-RRYIFCTEDR--AIPLAHQKQMAAGFS-------ADETFDLATGHSPFFSAPGPLADILDRIANAT---------------
ZP_01015348.1    ETPLTLSD-RFASVP-KVYIRCAEDR--TIPPEYQEEMTADWP-------SDRVHVMNSSHSPFFADPQGLARLLTRIEGQF---------------
YP_165260.1
```

Figure 6 (continued)

US 8,278,063 B2

METHODS FOR DEGRADING TOXIC COMPOUNDS

FIELD OF THE INVENTION

The invention relates to bacteria, bacterial extracts, supernatants obtained from the culturing of said bacteria, polypeptides and compositions for degrading benzimidazole carbamate fungicides, carbanilate fungicides, sulfonamide herbicides, thioamide herbicides and/or synthetic pyrethroid insecticides. In particular, the invention relates to the identification of *Nocardioides* sp. which degrades benzimidazole carbamate fungicides, carbanilate fungicides, sulfonamide herbicides, thioamide herbicides and/or synthetic pyrethroid insecticides.

BACKGROUND OF THE INVENTION

Chemical pesticides have become indispensable in modern agriculture for controlling insect, plant and fungal pests. It has been estimated that, worldwide, 4 million tonnes of pesticides were applied to crops in 1999. Global pesticide sales reached approximately US$33 billion in 2004. However, the vast majority of the active ingredients do not reach target pests but instead enter groundwater and rivers through misapplication, runoff and leaching. Accordingly, there is mounting public concern about the deleterious effects of pesticide contamination, through its impacts on both the environment and on human health. Technologies for decontaminating pesticide residues are therefore needed. Traditional methods of remediation of toxic compounds including incineration, burial or chemical degradation (oxidation, reduction and hydrolysis) are often too expensive or otherwise impractical for cleaning up the pesticide residues, but these problems may be ameliorated by bioremediation, a process by which biological agents and processes are utilised to detoxify environmental pollutants. Bioremediation has been applied effectively to the clean-up of pesticides in irrigation tail water, groundwater and soil.

The direct application of live microorganisms to contaminated soils has been used to degrade a number of pesticides. An alternative to microbial remediation is the use of a relatively new technology known as enzymatic bioremediation. It is particularly suited to environments not conducive to microbial growth or situations where rapid remediation is required. This includes irrigation run-off water, spills, commodity clean-up, wash-down of farm machinery and for the personal protection of agricultural workers. Enzyme-based bioremediation often utilises the degradative capabilities of pesticide-resistant microorganisms, insects or weeds as a source of catalytic proteins. Typically, once an organism possessing the desired degradative property is isolated, gene technology is then used to clone the gene(s) responsible. The enzymatic properties of the resultant gene products are determined and, if necessary, improved using modern molecular biology techniques. These enzymes are then produced in quantity and applied directly to the affected area, e.g. field or drainage waters, in order to reduce pesticide load and, hence, toxicity. This technology is currently being applied to the clean-up of pesticide residues from agricultural wastewater.

Carbamate pesticides are derived from carbamic acid (HOOC—$NH_2$) and possess the general structure shown in FIG. 1A. The chemical side chains principally govern the biological activity of the pesticide. The atom denoted by the X is either an oxygen or a sulfur, whereas $R_1$ and $R_2$ can be a number of different organic side chains, although quite often a methyl group or a hydrogen. $R_3$ is usually a bulky aromatic group or an oxime moiety. Benzimidazole carbamate fungicides include benomyl, carbendazim, cypendazole, debacarb and mecarbinzid.

Early studies provided evidence that microorganisms play a role in enhancing carbamate degradation in "aggressive" soils in which repeated pesticide applications led to a greatly reduced persistence of these compounds (Karns et al., 1986; Derbyshire et al., 1987; Karns et al., 1991; Tomasek et al., 1989). It has since been shown that the primary step in the carbamate degradation process is often hydrolysis across the carbamate linkage (Topp et al., 1993). This simple reaction is predominantly a cofactor-independent process and thus advantageous for enzymes that are to be considered for bioremediation. Several carbamate hydrolase enzymes responsible for the degradation have now been isolated from various organisms. Examples of enzymes which have been shown to degrade carbamates include MCD (Tomasek et al., 1989), cahA (Hayatsu et al., 2001), cehA (Bomscheuer et al., 2002) and PCD (Genbank Accession No. M94965).

Involvement of fungi and bacteria in enhanced and nonenhanced biodegradation of carbendazim and other benzimidazole compounds in soil has been reported (Yarden et al., 1990). Furthermore, two carbendazim degrading bacteria, *Ralstonia* sp. strain 1-1 and *Rhodococcus* sp. Dj1-6 have been described (Zhang et al., 2005; Jing-Liang et al., 2006). However, no gene-enzyme system responsible for the carbendazim hydrolytic activity is known to date.

There is a need for methods and enzymes which can be used for the bioremediation of, for example, soils, foodstuff and water samples contaminated with toxic compounds including degrading benzimidazole carbamate fungicides, carbanilate fungicides, sulfonamide herbicides, thioamide herbicides and/or synthetic pyrethroid insecticides.

SUMMARY OF THE INVENTION

The present inventors have identified bacteria which degrade benzimidazole carbamate fungicides, carbanilate fungicides, sulfonamide herbicides, thioamide herbicides and/or synthetic pyrethroid insecticides.

Thus, in a first aspect the present invention provides a composition for degrading a benzimidazole carbamate fungicide, a carbanilate fungicide, a sulfonamide herbicide, a thioamide herbicide and/or a synthetic pyrethroid insecticide, the composition comprising a *Nocardioides* sp., an extract thereof or supernatant obtained from the culture thereof, which degrades a benzimidazole carbamate fungicide, a carbanilate fungicide, a sulfonamide herbicide, a thioamide herbicide and/or a synthetic pyrethroid insecticide.

Examples of benzimidazole carbamate fungicides which can be degraded using a composition of the invention include, but are not limited to, benomyl, carbendazim, cypendazole, debacarb and mecarbinzid. In a particularly preferred embodiment, the benzimidazole carbamate fungicide is carbendazim.

An example of a carbanilate fungicide which can be degraded using a composition of the invention is diethofencarb.

Examples of sulfonamide herbicides which can be degraded using a composition of the invention include, but are not limited to, asulam, carbasulam, fenasulam, oryzalin, penoxsulam and pyroxsulam.

Examples of thioamide herbicides which can be degraded using a composition of the invention include, but are not limited to, bencarbazone and chlorthiamid.

Examples of synthetic pyrethroid insecticides which can be degraded using a composition of the invention include, but are not limited to, permethrin, fenvalerate, esfenvalerate, cypermethrin, alpha-cypermethrin, deltamethrin, fenpropathrin, fluvalinate, flucythrinate, cyfluthrin, acrinathrin, tralomethrin, cycloprothrin, lambda-cyhalothrin, tefluthrin, bifenthrin, transfluthrin, zeta-cypermethrin, and halfenprox. In a preferred embodiment, the synthetic pyrethroid insecticide is mCNMP 1(R)cis-α(S), mCNMP 1(S)trans-α(S) or mCNMP 1(R)trans-α(R).

In a preferred embodiment, the *Nocardioides* sp. comprises a nucleotide sequence provided as SEQ ID NO:4 or a sequence which is at least 99%, more preferably at least 99.5%, identical thereto.

In a further preferred embodiment, the *Nocardioides* sp., extract thereof or supernatant obtained from the culture thereof, comprises a polypeptide which comprises
  i) an amino acid sequence provided as SEQ ID NO:1, or
  ii) an amino acid sequence which is at least 41% identical to SEQ ID NO:1.

In a further embodiment, the polypeptide comprises
  i) an amino acid sequence provided as SEQ ID NO:5 and/or SEQ ID NO:6, or
  ii) an amino acid sequence which is at least 50% identical to SEQ ID NO:5 or SEQ ID NO:6.

Preferably, the polypeptide has a molecular weight of about 26 kDa. In a further preferred embodiment, the polypeptide has a $K_m$ for carbendazim which is less than about 100 µM, more preferably less than about 20 µM, more preferably less than about 10 µM. In a further embodiment, the polypeptide has a $K_m$ for carbendazim of about 6.1 µM. $K_m$ for carbendazim can be determined as described in Example 6.

In a particularly preferred embodiment, the *Nocardioides* sp. is strain SG-4G deposited under Accession number V07/015,486 on 20 Jun. 2007 at the National Measurement Institute, Australia. In a further preferred embodiment, the composition comprises, or consists of, a radiation killed freeze-dried culture of the *Nocardioides* sp. SG-4G.

In another aspect, the present invention provides an isolated strain of *Nocardioides* sp. which degrades a benzimidazole carbamate fungicide, a carbanilate fungicide, a sulfonamide herbicide, a thioamide herbicide and/or a synthetic pyrethroid insecticide.

Preferably, the *Nocardioides* sp. is strain SG-4G deposited under Accession number V07/015,486 on 20 Jun. 2007 at the National Measurement Institute, Australia.

The strain may be alive or dead (killed). In a particularly preferred embodiment, the strain is a radiation killed freeze-dried culture of the *Nocardioides* sp. SG-4G.

Also provided is an extract of the isolated strain of the invention which degrades a benzimidazole carbamate fungicide, a carbanilate fungicide, a sulfonamide herbicide, a thioamide herbicide and/or a synthetic pyrethroid insecticide. For example, the extract can be a cell lysate or have been subjected to one or more purification procedures known in the art such as, removal of nucleic acids and/or cell wall material.

The inventors have determined that the enzyme with the desired activity is secreted from the cell of *Nocardioides* sp. Thus, in a further aspect the present invention provides supernatant obtained from the culturing of the isolated strain of the invention, or a fraction thereof which degrades a benzimidazole carbamate fungicide, a carbanilate fungicide, a sulfonamide herbicide, a thioamide herbicide and/or a synthetic pyrethroid insecticide.

A new enzyme which degrades a benzimidazole carbamate fungicide, a carbanilate fungicide, a sulfonamide herbicide, and/or a thioamide herbicide has been purified. Accordingly, in another aspect the present invention provides a substantially purified and/or recombinant polypeptide comprising amino acids having a sequence provided as SEQ ID NO:1, a biologically active fragment thereof, or an amino acid sequence which is at least 41% identical to SEQ ID NO:1, wherein the polypeptide degrades a benzimidazole carbamate fungicide, a carbanilate fungicide, a sulfonamide herbicide, and/or a thioamide herbicide.

In an embodiment, the polypeptide comprises
  i) an amino acid sequence provided as SEQ ID NO:5 and/or SEQ ID NO:6, or
  ii) an amino acid sequence which is at least 50% identical to SEQ ID NO:5 or SEQ ID NO:6.

Preferably, the benzimidazole carbamate fungicide is carbendazim.

Preferably, the polypeptide can be purified from a *Nocardioides* sp. More preferably, the polypeptide can be purified from a *Nocardioides* sp strain SG-4G deposited under Accession number V07/015,486 on 20 Jun. 2007 at the National Measurement Institute, Australia.

Preferably, the polypeptide has a molecular weight of about 26 kDa.

In an embodiment, the polypeptide is fused to at least one other polypeptide sequence. The at least one other polypeptide may be, for example, a polypeptide that enhances the stability of a polypeptide of the present invention, or a polypeptide that assists in the purification of the fusion protein.

Also provided is an isolated and/or exogenous polynucleotide comprising:
  i) a sequence of nucleotides as provided in SEQ ID NO:2 or SEQ ID NO:3,
  ii) a sequence of nucleotides encoding a polypeptide of the invention,
  iii) a sequence of nucleotides which is at least 41% identical to i),
  iv) a sequence of nucleotides which hybridizes to i) under stringent conditions, and/or
  v) a sequence of nucleotides complementary to any one of i) to iv).

Preferably, the polynucleotide is operably linked to a promoter capable of directing expression of the polynucleotide in a cell.

In another aspect, the present invention provides a vector comprising the polynucleotide of the invention.

In a further aspect, the present invention provides a host cell comprising a polynucleotide of the invention and/or a vector of the invention.

The host cell can be any cell type such as a bacterial, fungal, plant or animal cell. In a preferred embodiment, the cell is a bacterial cell.

In another aspect, the present invention provides a method of producing a polypeptide of the invention, the method comprising cultivating a host cell of the invention encoding said polypeptide, or a vector of the invention encoding said polypeptide, under conditions which allow expression of the polynucleotide encoding the polypeptide, and recovering the expressed polypeptide.

In one embodiment, the method is preformed using a cell expression system. In another embodiment, the method is performed is a cell-free expression system.

Preferably, the method further comprises recovering the polypeptide.

Also provided is a polypeptide produced using a method of the invention.

In another aspect, the present invention provides a polymeric sponge or foam for degrading a benzimidazole carbamate fungicide, a carbanilate fungicide, a sulfonamide herbicide, and/or a thioamide herbicide, the foam or sponge comprising a polypeptide of the invention immobilized on a polymeric porous support.

Preferably, the porous support comprises polyurethane.

In a preferred embodiment, the sponge or foam further comprises carbon embedded or integrated on or in the porous support.

In another aspect, the present invention provides a transgenic plant comprising an exogenous polynucleotide encoding at least one polypeptide of the invention.

Preferably, the polynucleotide is stably incorporated into the genome of the plant.

In a further aspect, the present invention provides a transgenic non-human animal comprising an exogenous polynucleotide encoding at least one polypeptide of the invention.

In another aspect, the present invention provides an extract of a host cell of the invention, a transgenic plant of the invention, a transgenic non-human animal of the invention, wherein the extract comprises a polypeptide of the invention.

In another aspect, the present invention provides a composition for degrading a benzimidazole carbamate fungicide, a carbanilate fungicide, a sulfonamide herbicide, and/or a thioamide herbicide, the composition comprising a polypeptide of the invention, a polynucleotide of the invention, a vector of the invention, a host cell of the invention, an extract of the invention, and/or supernatant, or fraction thereof, obtained from the culture of a host cell of the invention.

Preferably, the composition comprises one or more acceptable carriers.

In a further aspect, the present invention provides a method for degrading a benzimidazole carbamate fungicide, a carbanilate fungicide, a sulfonamide herbicide, a thioamide herbicide and/or a synthetic pyrethroid insecticide, the method comprising contacting the benzimidazole carbamate fungicide, carbanilate fungicide, sulfonamide herbicide, thioamide herbicide and/or synthetic pyrethroid insecticide with a composition of the invention, an isolated strain of the invention, an extract of the invention, supernatant or a fraction thereof of the invention, a polypeptide of the invention, a polynucleotide of the invention, a vector of the invention, a host cell of the invention and/or a sponge or foam of the invention.

Preferably, the benzimidazole carbamate fungicide, carbanilate fungicide, sulfonamide herbicide, thioamide herbicide and/or synthetic pyrethroid insecticide is in a sample selected from, but not limited to, soil, water, biological material or a combination thereof.

In another aspect, the present invention provides a method for degrading a benzimidazole carbamate fungicide, a carbanilate fungicide, a sulfonamide herbicide, and/or a thioamide herbicide in a sample, the method comprising contacting the sample with a transgenic plant of the invention.

In an embodiment, the sample is soil such as soil in a field.

Also provided is a part of a plant of the invention which comprises the exogenous polynucleotide. Preferably, the part is a seed.

In another aspect, the present invention provides an isolated antibody which specifically binds a polypeptide of the invention.

In another aspect, the present invention provides a method of treating toxicity caused by a benzimidazole carbamate fungicide, a carbanilate fungicide, a sulfonamide herbicide, a thioamide herbicide and/or a synthetic pyrethroid insecticide in a subject, the method comprising administering to the subject a composition of the invention, an isolated strain of the invention, an extract of the invention, supernatant or a fraction thereof of the invention, a polypeptide of the invention, a polynucleotide of the invention, a vector of the invention, a host cell of the invention, a sponge or foam of the invention, a plant of the invention or a transgenic non-human of the invention.

Also provided is the use of a composition of the invention, an isolated strain of the invention, an extract of the invention, supernatant or a fraction thereof of the invention, a polypeptide of the invention, a polynucleotide of the invention, a vector of the invention, a host cell of the invention, a sponge or foam of the invention, a plant of the invention or a transgenic non-human of the invention for the manufacture of a medicament for treating toxicity caused by a benzimidazole carbamate fungicide, a carbanilate fungicide, a sulfonamide herbicide, a thioamide herbicide and/or a synthetic pyrethroid insecticide in a subject.

The polypeptides of the present invention can be mutated, and the resulting mutants screened for altered activity, such as enhanced enzymatic activity. Such mutations can be performed using any technique known in the art including, but not limited to, in vitro mutagenesis and DNA shuffling. Thus, in a further aspect, the present invention provides a method of producing a polypeptide with enhanced ability to degrade a benzimidazole carbamate fungicide, a carbanilate fungicide, a sulfonamide herbicide, and/or a thioamide herbicide, or altered substrate specificity for a different type of benzimidazole carbamate fungicide, carbanilate fungicide, sulfonamide herbicide, and/or thioamide herbicide, the method comprising (i) altering one or more amino acids of a polypeptide of the invention, (ii) determining the ability of the altered polypeptide obtained from step (i) to degrade a benzimidazole carbamate fungicide, a carbanilate fungicide, a sulfonamide herbicide, and/or a thioamide herbicide, and (iii) selecting an altered polypeptide with enhanced ability to degrade a benzimidazole carbamate fungicide, a carbanilate fungicide, a sulfonamide herbicide, and/or a thioamide herbicide, or altered substrate specificity for a different type of benzimidazole carbamate fungicide, carbanilate fungicide, sulfonamide herbicide, and/or thioamide herbicide, when compared to the polypeptide used in step (i).

Step (i) can be performed using any suitable technique known in the art such as, but not limited to, site-directed mutagenesis, chemical mutagenesis and DNA shuffling on the encoding nucleic acid.

Also provided is a polypeptide produced by a method of the invention.

The polypeptide of the invention can be used as a marker to identify recombinant cells. Thus, is a further aspect the present invention provides for the use of a polypeptide of the invention, or a polynucleotide encoding said polypeptide, as a selectable marker for detecting and/or selecting a host cell.

Also provided is a method for detecting a host cell, the method comprising i) contacting a cell or a population of cells with a polynucleotide encoding a polypeptide of the invention under conditions which allow uptake of the polynucleotide by the cell(s), and ii) selecting a host cell by exposing the cells from step i), or progeny cells thereof, to a benzimidazole carbamate fungicide, a carbanilate fungicide, a sulfonamide herbicide, and/or a thioamide herbicide.

In an embodiment, the polynucleotide comprises a first open reading frame encoding a polypeptide of the invention, and a second open reading frame not encoding a polypeptide of the invention.

In one embodiment, the second open reading frame encodes a polypeptide.

In an alternate embodiment, the second open reading frame encodes a polynucleotide which is not translated. Examples include, but are not limited to, a catalytic nucleic acid, a dsRNA molecule or an antisense molecule.

The cell can be any cell type such as, but not limited to, a plant cell, bacterial cell, fungal cell or animal cell. In a preferred embodiment, the cell is an animal cell.

In yet another aspect, the present invention provides a kit for degrading a benzimidazole carbamate fungicide, a carbanilate fungicide, a sulfonamide herbicide, a thioamide herbicide and/or a synthetic pyrethroid insecticide, the kit comprising a composition of the invention, an isolated strain of the invention, an extract of the invention, supernatant or a fraction thereof of the invention, a polypeptide of the invention, a polynucleotide of the invention, a vector of the invention, a host cell of the invention, a sponge or foam of the invention, a plant of the invention or a transgenic non-human of the invention.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

Figure 1B:
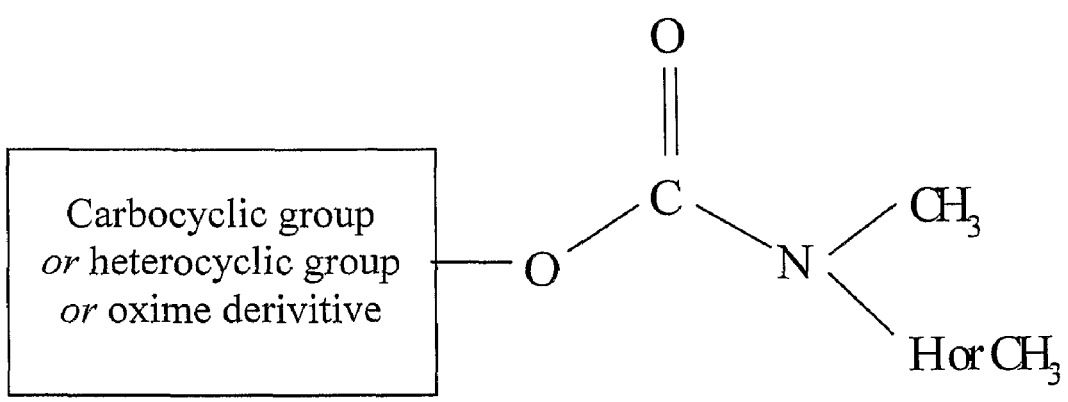

FIG. 1. General structure of carbamate pesticides (FIG. 1A) and benzimidazole carbamate fungicides (FIG. 1B).

Figure 2:
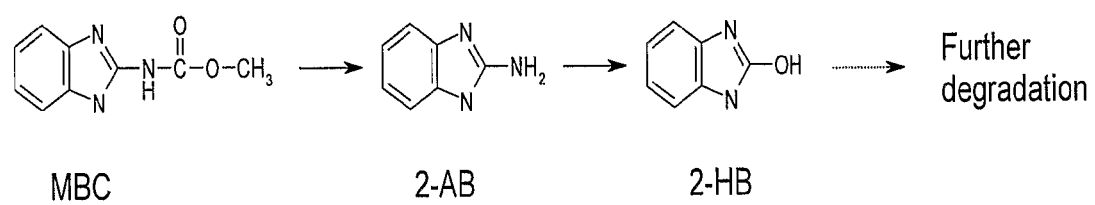

FIG. 2. Initial steps of carbendazim degradation in *Nocardioides* sp. SG-4G.

Figure 3:
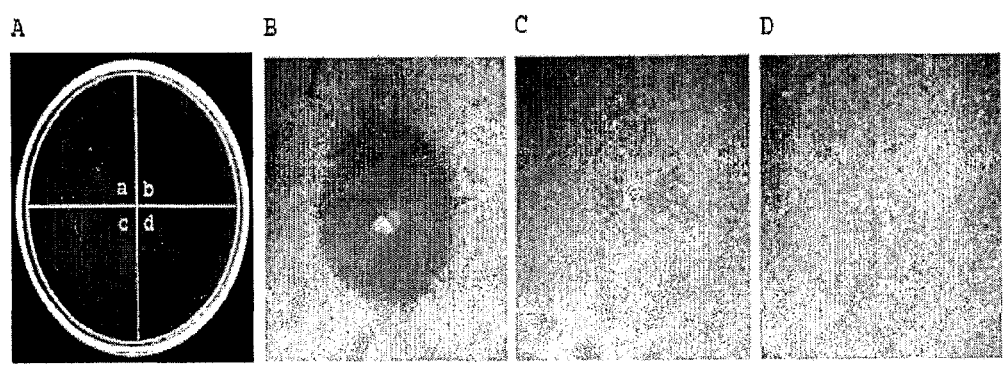

FIG. 3. HTP assay for detecting carbendazim hydrolytic activity: (Aa) strain SG. 4G; (Ab, Ac and Ad) negative controls; (B) enlarged view of the cleared spot inoculated with SG-4G; and (C,D) enlarged view of negative controls.

Figure 4:
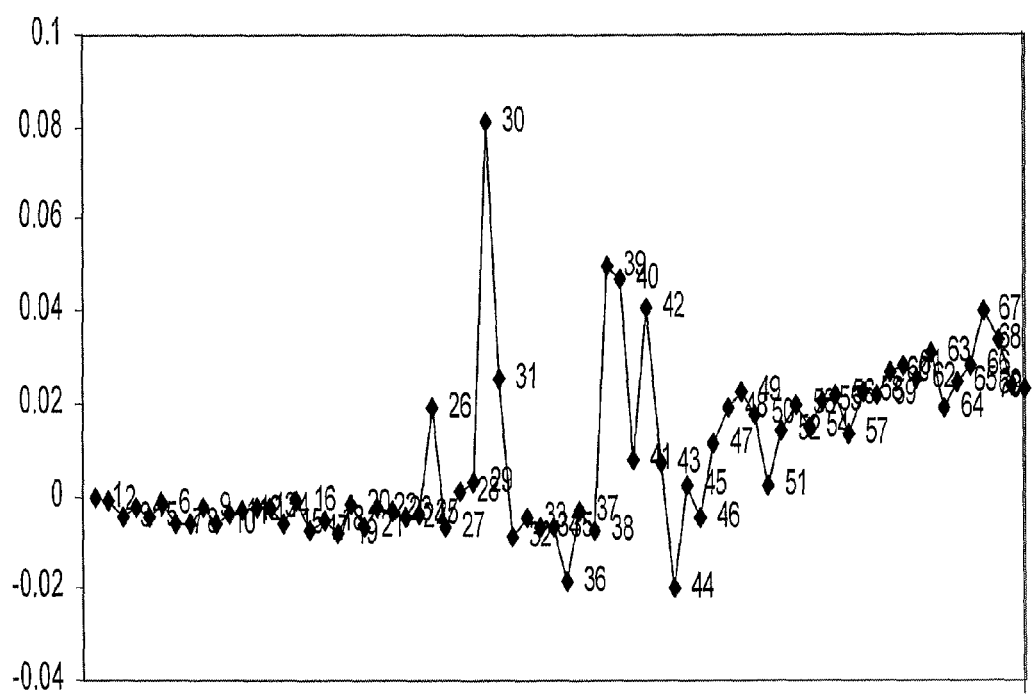

FIG. 4. Esterase activity (vertical axis) in fractions generated by ion exchange chromatography. Note that fractions 30 and 31 also have carbendazim hydrolytic activity.

Figure 5:
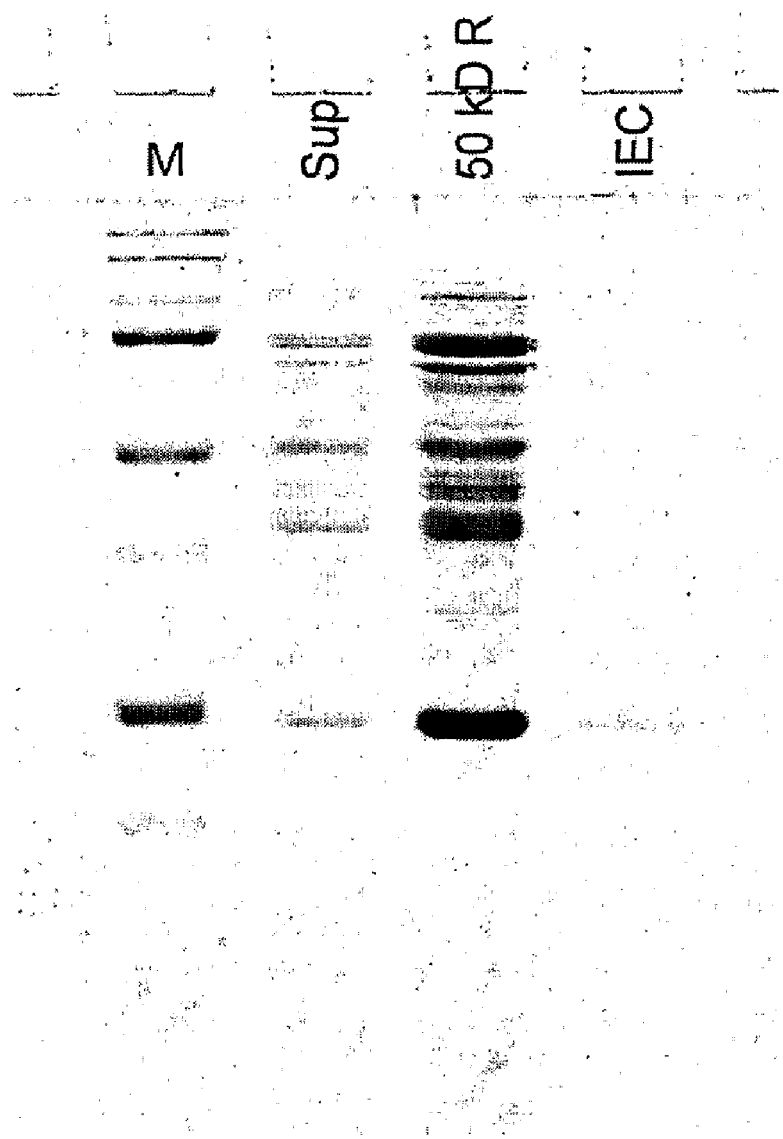

FIG. 5. SDS PAGE showing the enzyme purification steps. Sup: culture supernatant; 50 kD R: retentate of 50 kD molecular weight cut-off membranes; IEC: purified protein after ion exchange chromatography; M: molecular weight markers.

Figure 6:
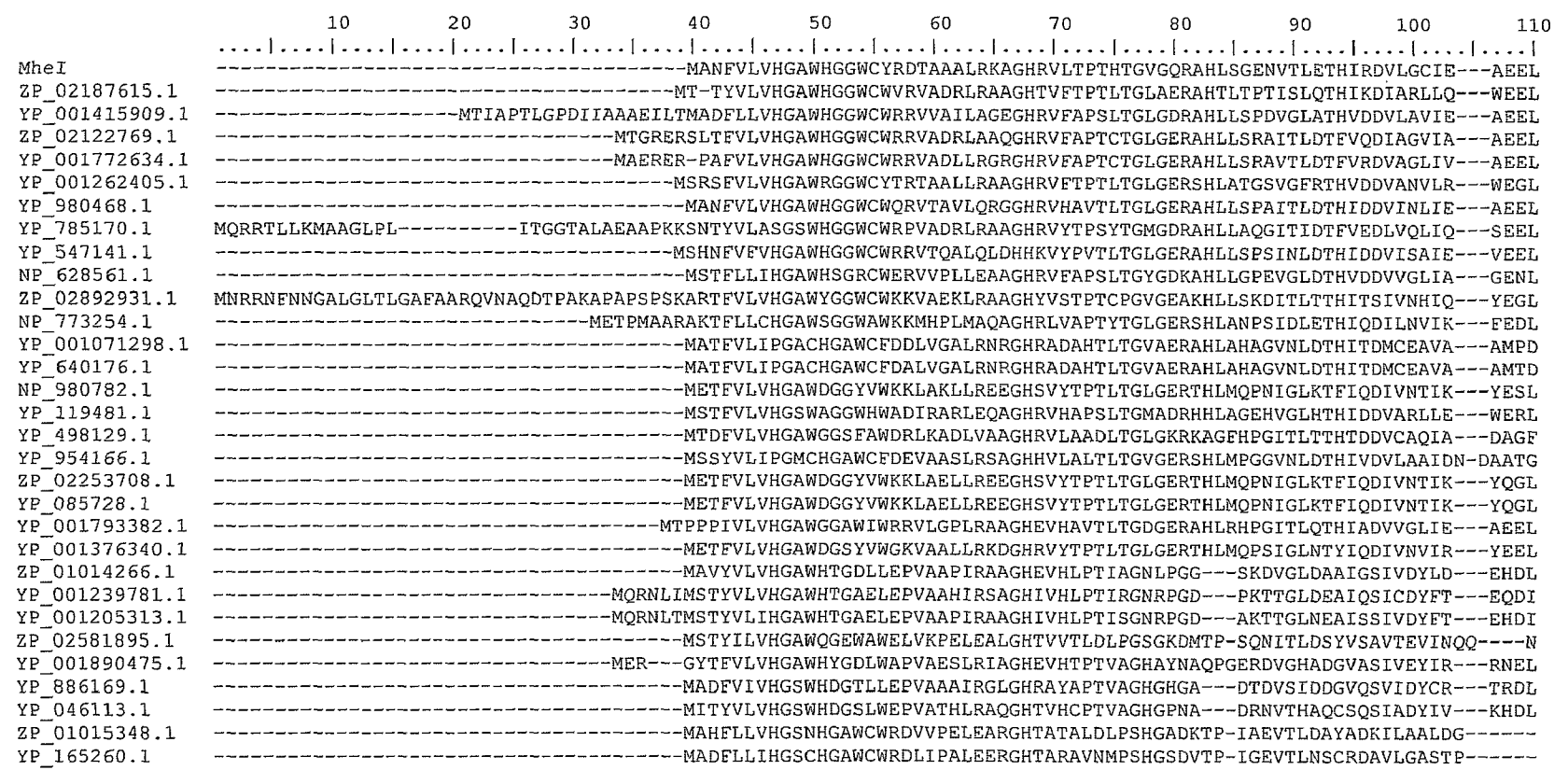
Figure 6:
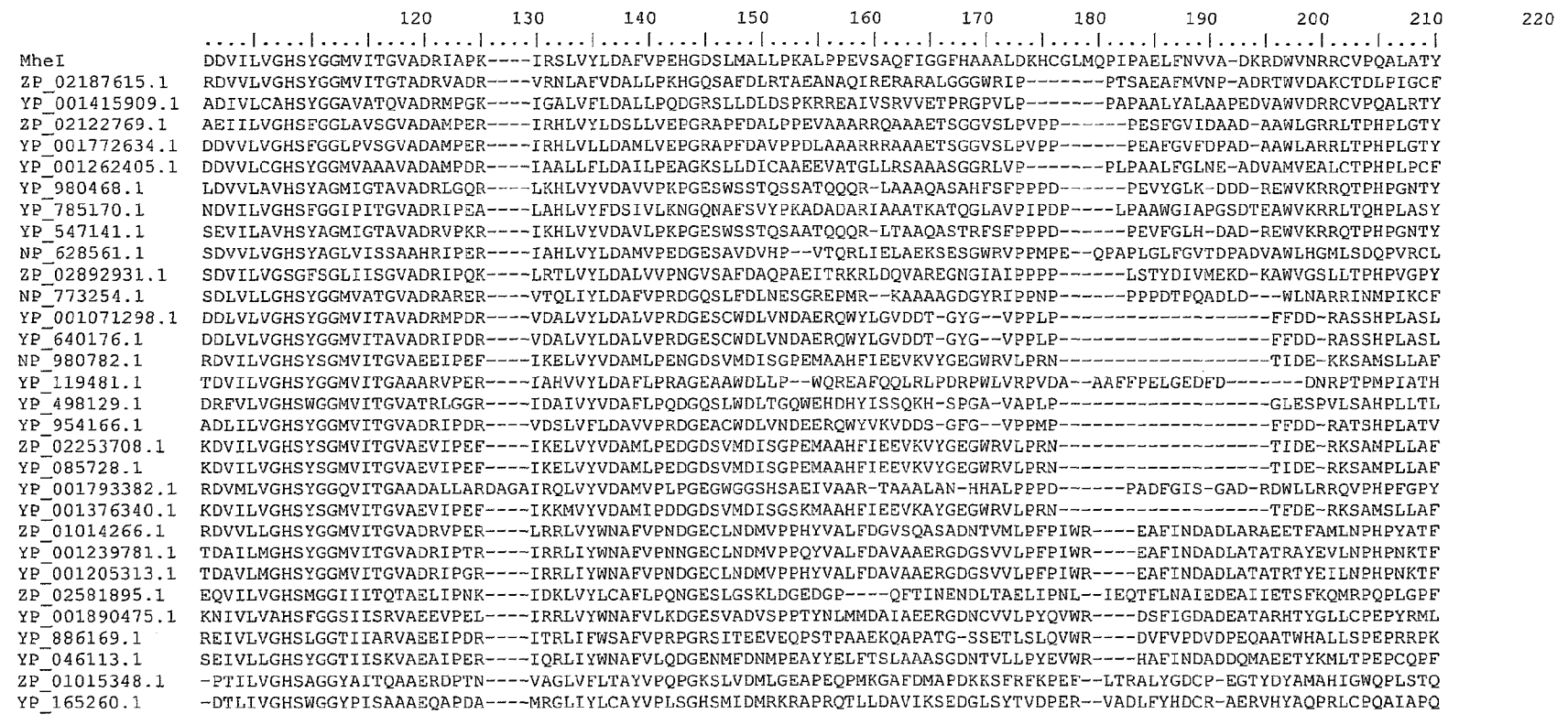

FIG. 6. Sequence alignment of MheI with previously known or predicted proteins. Sequences provided as SEQ ID NO's 1 and 14 to 43 respectively.

Figure 7:
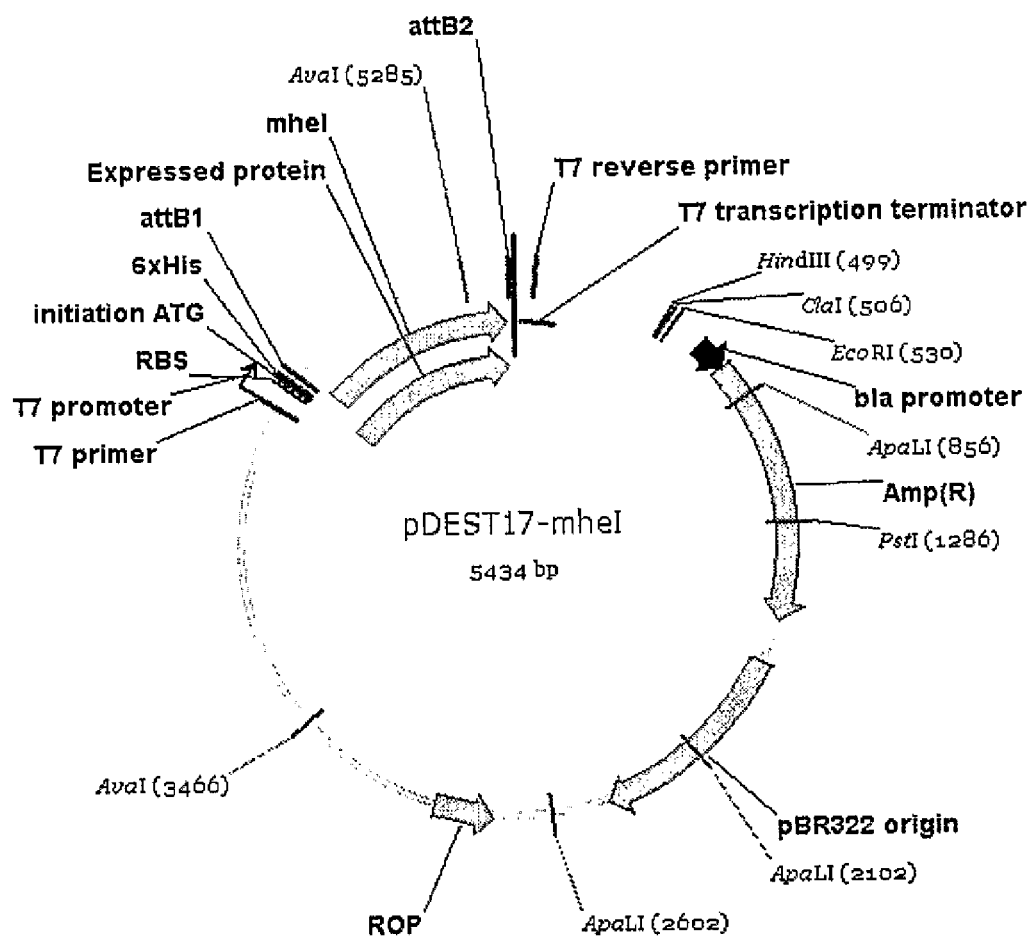

FIG. 7. Schematic representation of pDEST17-mheI.

Figure 8:
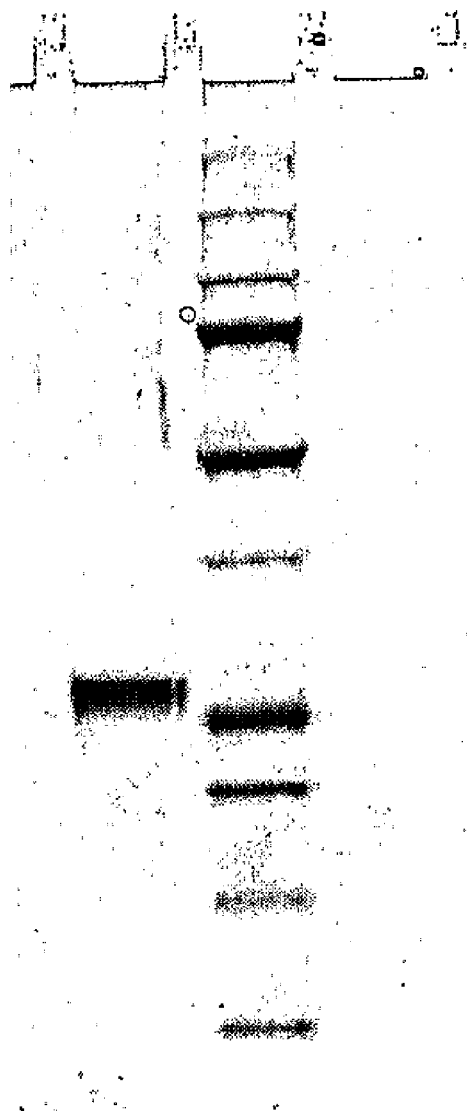

FIG. 8. SDS PAGE showing recombinantly expressed MheI (left lane).

Figure 9:
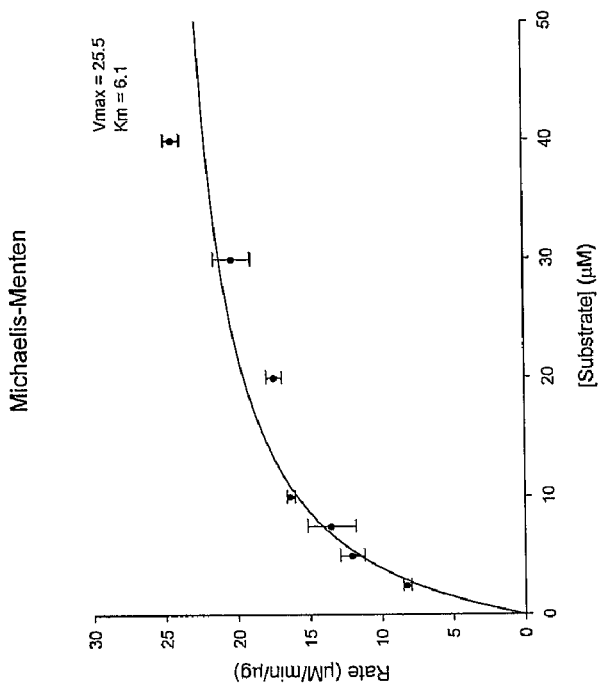
Figure 9:
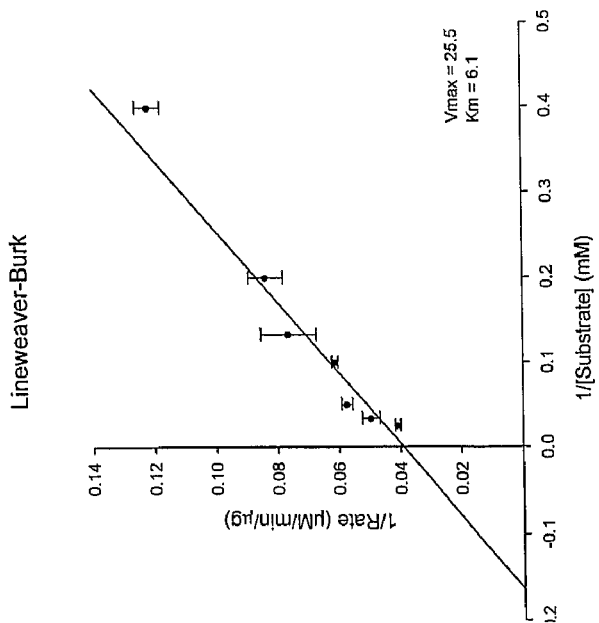

FIG. 9. Enzyme kinetics of MheI for carbendazim.

Figure 10:
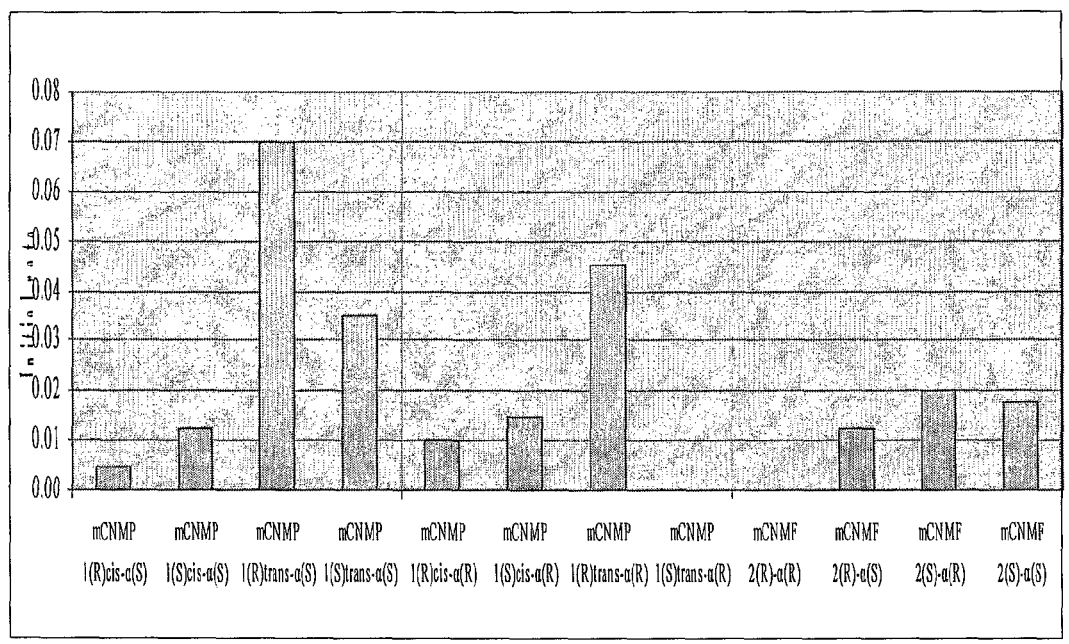

FIG. 10. Activity of SG-4G against synthetic pyrethroids.

Figure 11:
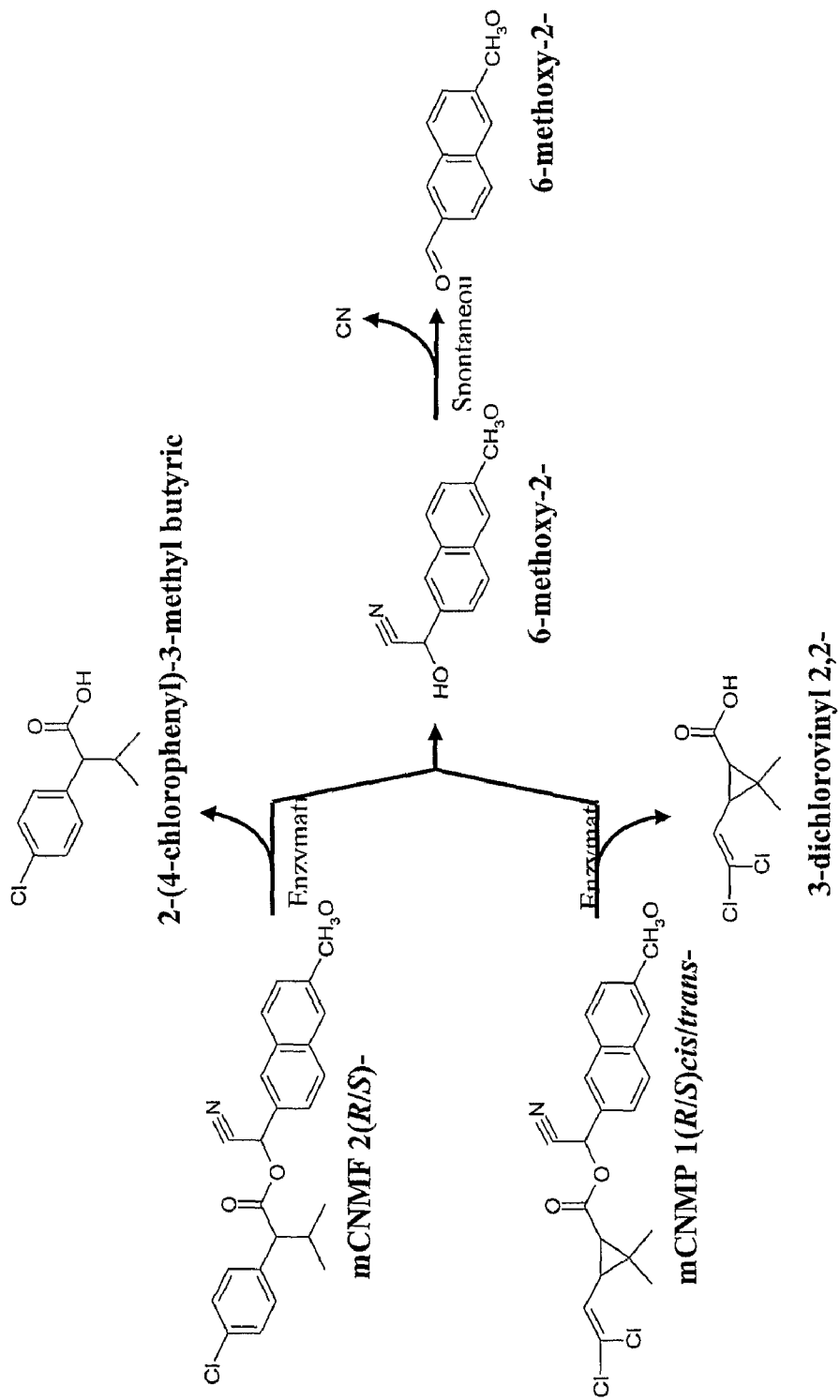

FIG. 11. Initial steps of synthetic pyrethroid degradation by the *Nocardioides* sp. 30 kD retentate.

KEY TO SEQUENCE LISTING

SEQ ID NO:1—Amino acid sequence of MheI enzyme.
SEQ ID NO:2—Nucleotide sequence encoding MheI enzyme.
SEQ ID NO:3 Codon optimized nucleotide sequence encoding MheI enzyme for expression in *E. coli*.
SEQ ID NO:4-16S rRNA gene from *Nocardioides* sp. SG-4G.
SEQ ID NO's 5 and 6—Partial sequence of MheI enzyme.
SEQ ID NO's 7 to 13—Oligonucleotide primers.
SEQ ID NO:14—*Alpha proteobacterium* BAL199 putative esterase (Genbank ZP_02187615.1).
SEQ ID NO:15—*Xanthobacter autotrophicus* Py2 putative esterase or lipase (Genbank YP_001415909.1).
SEQ ID NO:16—*Methylobacterium nodulans* ORS 2060 putative esterase (Genbank ZP_02122769.1).
SEQ ID NO:17—*Methylobacterium* sp. 4-46 putative esterase (Genbank YP_001772634).
SEQ ID NO:18—*Sphingomonas wittichii* RW1 putative esterase (Genbank YP_001262405.1).
SEQ ID NO:19—*Polaromonas naphthalenivorans* CJ2 putative esterase (Genbank YP_980468.1).
SEQ ID NO:20—*Bordetella avium* 197N esterase (Genbank YP_785170.1).
SEQ ID NO:21—*Polaromonas* sp. JS666 putative esterase (Genbank YP_547141.1).
SEQ ID NO:22—*Streptomyces coelicolor* A3(2) putative esterase (Genbank NP_628561.1).
SEQ ID NO:23—*Burkholderia ambifaria* IOP40-10 putative esterase (Genbank ZP_02892931.1).
SEQ ID NO:24 *Bradyrhizobium japonicum* USDA 110 putative esterase (Genbank NP_773254.1).
SEQ ID NO:25—*Mycobacterium* sp. JLS putative esterase (Genbank YP_001071298.1).
SEQ ID NO:26—*Mycobacterium* sp. MCS putative esterase (Genbank YP_640176.1).
SEQ ID NO:27—*Bacillus cereus* ATCC 10987 putative esterase (Genbank NP_980782).
SEQ ID NO:28—*Nocardia farcinica* IFM 10152 putative esterase (Genbank YP_119481).
SEQ ID NO:29—*Novosphingobium aromaticivorans* DSM 12444 putative esterase (Genbank YP_498129.1).
SEQ ID NO:30—*Mycobacterium vanbaalenii* PYR-1 putative esterase (Genbank YP_954166.1).
SEQ ID NO:31—*Bacillus cereus* AH187 putative esterase (Genbank ZP_02253708.1).
SEQ ID NO:32—*Bacillus cereus* E33L putative hydrolase (Genbank YP_085728.1).
SEQ ID NO:33—*Leptothrix cholodnii* SP-6 putative esterase (Genbank YP_001793382.1).
SEQ ID NO:34—*Bacillus cereus* subsp. *cytotoxis* NVH 391-98 putative esterase (Genbank YP_001376340.1).
SEQ ID NO:35—*Rhodobacterales bacterium* HTCC2654 putative esterase (Genbank ZP_01014266.1).
SEQ ID NO:36—*Bradyrhizobium* sp. BTAi1 putative alpha/beta hydrolase (Genbank YP_001239781.1).
SEQ ID NO:37—*Bradyrhizobium* sp. ORS278 putative alpha/beta hydrolase (Genbank YP_001205313.1).
SEQ ID NO:38—*Bacillus cereus* B4264 putative alpha/beta hydrolase (Genbank ZP_02581895.1).
SEQ ID NO:39—*Burkholderia phytofirmans* PsJN putative esterase (Genbank YP_001890475.1).
SEQ ID NO:40—*Mycobacterium smegmatis* str. MC2 155 putative esterase (Genbank YP_886169.1).
SEQ ID NO:41—*Acinetobacter* sp. ADP1 putative esterase (Genbank YP_046113.1).
SEQ ID NO:42—*Rhodobacterales bacterium* HTCC2654 putative esterase (Genbank ZP_01015348.1).
SEQ ID NO:43—*Silicibacter pomeroyi* DSS-3 putative esterase (Genbank YP_165260.1).

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, plant biology and/or chemistry, recombinant cell biology including transgenic plants, bioremediation, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the term "degrades", "degradation" and variations thereof refers to the product of enzymatic activity being less toxic and/or stable than the substrate. In particular, the product is less toxic to animal cells, especially fish or mammalian cells. In a particularly preferred embodiment, the enzymatic activity is hydrolyzing an ester bond of the substrate. In a preferred embodiment, the polypeptide of the invention is capable of degrading carbendazim to produce 2-aminobenzimidazole.

As used herein the terms "treating", "treat" or "treatment" include administering a therapeutically effective amount of an enzyme or composition as defined herein, or a polynucleotide encoding therefor, sufficient to reduce or eliminate at least one symptom of toxicity caused by benzimidazole carbamate fungicides, carbanilate fungicides, sulfonamide herbicides, thioamide herbicides and/or synthetic pyrethroid insecticides.

As used herein, the term "subject" refers to any organism to which benzimidazole carbamate fungicides, carbanilate fungicides, sulfonamide herbicides, thioamide herbicides and/or synthetic pyrethroid insecticides is toxic. In a preferred embodiment the subject is an animal, e.g., a fish, bird or mammal. In an embodiment, the subject is a human. Other preferred embodiments include companion animals such as cats and dogs, as well as livestock animals such as horses, cattle, sheep and goats.

Carbamates

Carbamates are pesticides that possess an amide linkage, with the carbonyl group also forming a carboxylester linkage (FIG. 1A). Different constituents from either the amine group or the carboxyl ester group determine the target organism of these compounds. Carbamates with aromatic groups from both the amine and carboxylester (e.g. phenmedipham) are herbicidal. Carbamates with an aromatic group coming from the carboxylester group and a small group, such as a methyl group, coming from the amine (such as carbaryl) are insecticidal.

Carbamates with a benzimidazole group coming from the amine and a small methyl group coming from the carboxylester linkage are fungicidal. Such carbamates are referred to herein as benzimidazole carbamate fungicides and include, but are not limited to, benomyl, carbendazim, cypendazole, debacarb and mecarbinzid. A general structure for benzimidazole carbamate fungicides is provided in FIG. 1B.

Pyrethroids

Pyrethroids are synthetic analogs of pyrethrum pesticides. For example, pyrethroids include (in each case common name in accordance with The Pesticide Manual, 12th Edition): permethrin, fenvalerate, esfenvalerate, cypermethrin, alpha-cypermethrin, deltamethrin, fenpropathrin, fluvalinate, flucythrinate, cyfluthrin, acrinathrin, tralomethrin, cyclopro-thrin, lambda-cyhalothrin, tefluthrin, bifenthrin, transfluthrin, zeta-cypermethrin, and halfenprox.

The pyrethroid can be a Type I or Type II pyrethroid. Type I pyrethroid compounds (e.g., permethrin) differ from type II pyrethroid compounds in that type II compounds possess a cyano group on the α-carbon atom of the phenoxybenzyl moiety. Some examples of type II pyrethroids are cypermethrin, deltamethrin, and fenvalerate.

Examples of pyrethroid pesticides which can be hydrolysed using the methods of the present invention include, but are not restricted to; 3-phenoxybenzyl(1RS)-cis,trans-3-(2,2-dichlorovinyl)-2,2-dimethylcyclopropane carboxylate [permethrin], α-cyano-3-phenoxybenzyl-1-(4-ethoxyphenyl)-2,2-dichlorocyclopropane carboxylate [cyloprothrin], (RS)-α-cyano-3-phenoxybenzyl(RS)-2-(4-chlorophenyl)-3-isovalerate [fenvalerate], (S)-α-cyano-3-phenoxybenzyl(S)-2-(4-chlorophenyl)isovalerate [esfenvalerate], α-cyano-3-phenoxybenzyl(S)-2-(4-difluoromethoxyphenyl) isovalerate [flucythrinate], α-cyano-3-phenoxybenzyl 2-(2-chloro-4-trifluoromethylaniline)isovalerate [fluvalinate], (RS)-α-cyano-3-phenoxybenzyl 2,2,3,3-tetramethylcyclopropane carboxylate [fenpropathrin], 3-phenoxybenzyl(1R)-cis,trans-chrysanthemate[d-fenothrin], (RS)-α-cyano-3-phenoxybenzyl(1R)-cis,trans-chrysanthemate [cyfenothrin], (RS)3-allyl-2-methyl-4-oxocyclopento-2-enyl(1RS)-cis,trans-chrysanthemate [allethrin], α-cyano-3-phenoxybenzyl (1R)-cis,trans-3-phenoxybenzyl(1R)-cis,trans-3-(2,2-dichlorovinyl)-2,2-dimethylcyclopropane carboxylate [cypermethrin], (S)-α-cyano-3-phenoxybenzyl(1R)-cis-3-(2,2-dibromovinyl)-2,2-dimethy lcyclopropane carboxylate [deltamethrin], (S)-α-cyano-3-phenoxybenzyl(1R)-cis-2,2-dimethyl-3-(1,2,2,2-tetrabro moethyl)cyclopropane carboxylate [tralomethrin],3,4,5,6-tetrahydro imidomethyl (1RS)-cis,trans-chrysanthemate [tetramethrin], 5-benzyl-3-furylmethyl(1RS)-cis,trans-chrysanthemate [resmethrin], α-cyano-4-fluoro-3-phenoxybenzyl(1R,trans)-2,2-dimethyl-3-(2,2-dichlorovinyl)cyclopropane carboxylate [cyfluthrin].

Polypeptides

By "substantially purified" or "purified" we mean a polypeptide that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated.

The term "recombinant" in the context of a polypeptide refers to the polypeptide when produced by a cell, or in a cell-free expression system, in an altered amount or at an altered rate compared to its native state. In a preferred embodiment, the recombinant (host) cell is a cell that does not naturally produce the polypeptide. In an alternate embodiment, the recombinant cell is a cell which comprises an exogenous gene that causes an altered, preferably increased, amount of the polypeptide to be produced. A recombinant polypeptide of the invention includes polypeptides which have not been separated from other components of the recombinant cell, or cell-free expression system, in which it is produced, and polypeptides produced in such cells or cell-free systems which are subsequently purified away from at least some other components.

The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogues, fragments and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 200 amino acids in length and the GAP analysis aligns the two sequences over a region of at least 200 amino acids. Even more preferably, the GAP analysis aligns the two sequences over their entire length.

As used herein a "biologically active fragment" is a portion of a polypeptide as described herein which maintains a defined activity of the full-length polypeptide. Biologically active fragments can be any size as long as they maintain the defined activity. Preferably, biologically active fragments are at least 100 amino acids, more preferably at least 150 amino acids, and more preferably at least 200 amino acids, in length.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of a polypeptide described herein can be prepared by introducing appropriate nucleotide changes into a nucleic acid defined herein, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (altered) polypeptides can be prepared using any technique known in the art. For example, a polynucleotide described herein can be subjected to in vitro mutagenesis. Such in vitro mutagenesis techniques may include sub-cloning the polynucleotide into a suitable vector, transforming the vector into a "mutator" strain such as the E. coli XL-1 red (Stratagene) and propagating the transformed bacteria for a suitable number of generations. In another example, the polynucleotides of the invention along with other esterease or hydrolase encoding genes (such as those encoding one or more of the polypeptides provided as SEQ ID NO's 14 to 43) are subjected to DNA shuffling techniques as broadly described by Harayama (1998). Products derived from mutated/altered DNA can readily be screened using techniques described herein to determine if they are able to confer the desired phenotype such as enhanced activity and/or altered substrate specificity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as important for function. Other sites of interest are those in which particular residues obtained from various other esterases (see, for example, FIG. 6), and/or strains or species, are identical. These positions may be important for biological activity. These sites, especially those falling within a sequence of at least three other identically conserved sites, are preferably substituted in a relatively conservative manner. Such conservative substitutions are shown in Table 1.

In a preferred embodiment a mutant/variant polypeptide has one or two or three or four conservative amino acid changes when compared to a naturally occurring polypeptide. Details of conservative amino acid changes are provided in Table 1. As the skilled person would be aware, such minor changes can reasonably be predicted not to alter the activity of the polypeptide when expressed in a recombinant cell.

TABLE 1

Exemplary substitutions.

| Original Residue | Exemplary Substitutions |
| --- | --- |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |

TABLE 1-continued

Exemplary substitutions.

| Original Residue | Exemplary Substitutions |
|---|---|
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

Furthermore, if desired, unnatural amino acids or chemical amino acid analogues can be introduced as a substitution or addition into a polypeptide described herein. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide.

Polypeptides described herein can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant (host) cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant (host) cell. Such culturing conditions are within the expertise of one of ordinary skill in the art.

Polynucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the term "nucleic acid".

The term "exogenous" in the context of a polynucleotide refers to the polynucleotide when present in a cell, or in a cell-free expression system, in an altered amount compared to its native state. Preferably, the cell is a cell that does not naturally comprise the polynucleotide. However, the cell may be a cell which comprises an exogenous polynucleotide resulting in an altered, preferably increased, amount of production of the encoded polypeptide. An exogenous polynucleotide of the invention includes polynucleotides which have not been separated from other components of the recombinant cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

With regard to the defined polynucleotides, it will be appreciated that % identity figures higher than those provided above will encompass preferred embodiments. Thus, where applicable, in light of the minimum % identity figures, it is preferred that a polynucleotide of the invention comprises a sequence which is at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Polynucleotides of the invention include those which hybridize under stringent conditions to a nucleic acid encoding SEQ ID NO:1.

As used herein, the term "hybridizes" refers to the ability of two single stranded nucleic acid molecules being able to form at least a partially double stranded nucleic acid through hydrogen bonding.

As used herein, the phrase "stringent conditions" refers to conditions under which a polynucleotide, probe, primer and/or oligonucleotide will hybridize to its target sequence. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 to 50 nucleotides) and at least about 60° C. for longer probes, primers and oligonucleotides. Stringent conditions may also be achieved with the addition of destabilizing agents, such as formamide.

Stringent conditions are known to those skilled in the art and can be found in Ausubel et al. (supra), Current Protocols In Molecular Biology, John Wiley & Sons, N.Y. (1989), 6.3.1-6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2.xSSC, 0.01% BSA at 50° C.

Polynucleotides of the present invention may possess, when compared to naturally occurring polynucleotides, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

The present invention includes oligonucleotides that can be used as, for example, probes to identify nucleic acid molecules, or primers to produce nucleic acid molecules. Oligonucleotides of the present invention used as probes are typically conjugated with a detectable label such as a radioisotope, an enzyme, biotin, a fluorescent molecule or a chemiluminescent molecule. Probes and/or primers can be used to clone homologues of the polynucleotides of the invention from other species or strains. Furthermore, hybridization techniques known in the art can also be used to screen genomic or cDNA libraries for such homologues.

Oligonucleotides of the present invention can be RNA, DNA, or derivatives of either. Although the terms polynucleotide and oligonucleotide have overlapping meaning, oligonucleotides are typically relatively short single stranded molecules. The minimum size of such oligonucleotides is the size required for the formation of a stable hybrid between an oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

Usually, monomers of a polynucleotide or oligonucleotide are linked by phosphodiester bonds or analogues thereof. Analogs of phosphodiester linkages include: phosphorothioate, phosphorodithioate, phosphoroselenoate, phosphorodiselenoate, phosphoroanilothioate, phosphoranilidate, phosphoramidate.

Recombinant Vectors

One embodiment of the present invention includes a recombinant vector, which comprises at least one isolated polynucleotide of the present invention, inserted into any vector capable of delivering the polynucleotide into a host cell. Such a vector contains heterologous polynucleotide sequences, that is polynucleotide sequences that are not naturally found adjacent to polynucleotides of the present invention and that preferably are derived from a species other than the species from which the polynucleotides of the present invention are derived. The vector can be either RNA or DNA, either prokaryotic or eukaryotic, and typically is a transposon (such as described in U.S. Pat. No. 5,792,294), a virus or a plasmid.

One type of recombinant vector comprises a polynucleotide of the present invention operably linked to an expression vector. The phrase "operably linked" refers to insertion of a polynucleotide into an expression vector in a manner such that the polynucleotide is able to be expressed when transformed into a host cell. As used herein, an "expression vector" is a DNA or RNA vector that is capable of transforming a host cell and of effecting expression of a specified polynucleotide. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant (host) cells of the present invention, including in bacterial, fungal, endoparasite, arthropod, animal, and plant cells. Vectors of the invention can also be used to produce the polypeptide in a cell-free expression system, such systems are well known in the art.

"Operably linked" as used herein refers to a functional relationship between two or more nucleic acid (e.g., DNA) segments. Typically, it refers to the functional relationship of a transcriptional regulatory element to a transcribed sequence. For example, a promoter is operably linked to a coding sequence, such as a polynucleotide defined herein, if it stimulates or modulates the transcription of the coding sequence in an appropriate host cell and/or in a cell-free expression system. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

In particular, expression vectors of the present invention contain regulatory sequences such as transcription control sequences, translation control sequences, origins of replication, and other regulatory sequences that are compatible with the recombinant cell and that control the expression of polynucleotides of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, arthropod, nematode, plant or mammalian cells, such as, but not limited to, tac, lac, trp, trc, oxy-pro, omp/lpp, rrnB, bacteriophage lambda, bacteriophage T7, T7lac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences, as well as other sequences capable of controlling gene expression in prokaryotic or eukaryotic cells.

Coding sequences of the polypeptides of the invention can be optimized to maximize expression is a particular host cell using known techniques. An example of this is the open reading frame provided as SEQ ID NO:3 which has been optimized, using standard techniques in the art, for expression in *E. coli*.

Host Cells

As used herein, the terms "host cell" and "recombinant cell" are used interchangeably and include a cell transformed with an exogenous polynucleotide, as well as progeny cells thereof comprising said polynucleotide. Transformation of a polynucleotide into a cell can be accomplished by any method by which a polynucleotide can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotides of the present invention can remain extrachromosomal or can integrate into one or more sites within a chromosome of the transformed (i.e., recombinant) cell in such a manner that their ability to be expressed is retained.

Suitable cells to transform include any cell that can be transformed with a polynucleotide of the present invention. Host cells of the present invention either can be endogenously (i.e., naturally) capable of producing polypeptides of the present invention or can be capable of producing such polypeptides after being transformed with at least one polynucleotide of the present invention. Host cells of the present invention can be any cell capable of producing at least one protein of the present invention, and include bacterial, fungal (including yeast), parasite, nematode, arthropod, animal and plant cells. Examples of host cells include *Salmonella, Escherichia, Bacillus, Listeria, Saccharomyces, Spodoptera, Mycobacteria, Trichoplusia,* BHK (baby hamster kidney) cells, MDCK cells, CRFK cells, CV-1 cells, COS (e.g., COS-7) cells, and Vero cells. Further examples of host cells are *E. coli*, including *E coli* K-12 derivatives; *Salmonella typhi; Salmonella typhimurium*, including attenuated strains; *Spodoptera frugiperda; Trichoplusia ni*; and non-tumorigenic mouse myoblast G8 cells (e.g., ATCC CRL 1246). Particularly preferred host cells are bacterial, fungal, animal or plant cells.

Recombinant DNA technologies can be used to improve expression of an exogenous polynucleotide by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotides of the present invention include, but are not limited to, operatively linking polynucleotides to high-copy number plasmids, integration of the polynucleotide into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotides of the present invention to correspond to the codon usage of the host cell, and the deletion of sequences that destabilize transcripts.

Transgenic Plants

The term "plant" as used herein refers to whole plants and any substance which is present in, obtained from, derived from, or related to a plant, such as, for example, plant organs (e.g. leaves, stems, roots, flowers), single cells (e.g. pollen), seeds, plant cells and the like.

Plants contemplated for use in the practice of the present invention include both monocotyledons and dicotyledons. Target plants include, but are not limited to, the following: cereals (for example, wheat, barley, rye, oats, rice, maize, sorghum and related crops); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (peanut, rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as tobacco, nuts, coffee, sugar cane, tea, vines, hops, turf, bananas and natural rubber plants, as well as ornamentals (flowers, shrubs, broad-leaved trees and evergreens, such as conifers). In a preferred embodiment, the plant is from the families Gramineae, Composite, or Leguminosae, more preferably from the genera: *Fragaria, Lotus, Medicago, Onobrychis, Trifolium, Trigonella, Vigna, Citrus, Linum, Geranium, Manihot, Daucus, Brassica, Raphanus, Sinapis, Atropa, Capsicum, Datura, Hyoscyamus, Lycopersicon, Nicotiana, Solanum, Petunia, Digitalis, Majorana, Chichorium, Helianthus, Lactuca, Bromus, Asparagus, Antirrhinum, Heterocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, Apium, Agrostis, Phleum, Dactylis, Sorgum, Setaria, Zea, Oryza, Triticum, Secale, Avena, Hordeum, Saccharum, Poa, Festuca, Stenotaphrum, Cynodon, Coix, Olyreae, Phareae, Glycine, Pisum, Cicer, Phaseolus, Lens*, or *Arachis*, and even more preferably from corn, rice, triticale, rye, cotton, soybean, sorghum, wheat, oats, barley, millet, sunflower, canola, peas, beans, lentils, peanuts, yam beans, cowpeas, velvet beans, clover, alfalfa, lupine, vetch, lotus, sweet clover, wisteria, sweetpea or a nut plant.

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

A "transgenic plant" refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

A polynucleotide of the present invention may be expressed constitutively in the transgenic plants during all stages of development. Depending on the use of the plant or plant organs, the polypeptides may be expressed in a stage-specific manner. Furthermore, the polynucleotides may be expressed tissue-specifically.

Regulatory sequences which are known or are found to cause expression of a gene encoding a polypeptide of interest in plants may be used in the present invention. The choice of the regulatory sequences used depends on the target plant and/or target organ of interest. Such regulatory sequences may be obtained from plants or plant viruses, or may be chemically synthesized. Such regulatory sequences are well known to those skilled in the art.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triose-phosphate isomerase promoter, the adenine phosphoribosyl-transferase promoter of Arabidopsis, the rice actin 1 gene promoter, the mannopine synthase and octopine synthase promoters, the Adh promoter, the sucrose synthase promoter, the R gene complex promoter, and the chlorophyll α,β binding protein gene promoter. These promoters have been used to create DNA vectors that have been expressed in plants; see, e.g., PCT publication WO 8402913. All of these promoters have been used to create various types of plant-expressible recombinant DNA vectors.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea, the chloroplast fructose-1,6-biphosphatase promoter from wheat, the nuclear photosynthetic ST-LS1 promoter from potato, the serine/threonine kinase promoter and the glucoamylase (CHS) promoter from Arabidopsis thaliana. Also reported to be active in photosynthetically active tissues are the ribulose-1,5-bisphosphate carboxylase promoter from eastern larch (Larix laricina), the promoter for the Cab gene, Cab6, from pine, the promoter for the Cab-1 gene from wheat, the promoter for the Cab-1 gene from spinach, the promoter for the Cab 1R gene from rice, the pyruvate, orthophosphate dikinase (PPDK) promoter from Zea mays, the promoter for the tobacco Lhcb1*2 gene, the Arabidopsis thaliana Suc2 sucrose-$H^{30}$ symporter promoter, and the promoter for the thylakoid membrane protein genes from spinach (PsaD, PsaF, PsaE, PC, FNR, AtpC, AtpD, Cab, RbcS).

Other promoters for the chlorophyll α,β-binding proteins may also be utilized in the present invention, such as the promoters for LhcB gene and PsbP gene from white mustard (Sinapis alba). A variety of plant gene promoters that are regulated in response to environmental, hormonal, chemical, and/or developmental signals, also can be used for expression of RNA-binding protein genes in plant cells, including promoters regulated by (1) heat, (2) light (e.g., pea RbcS-3A promoter, maize RbcS promoter); (3) hormones, such as abscisic acid, (4) wounding (e.g., WunI); or (5) chemicals, such as methyl jasminate, salicylic acid, steroid hormones, alcohol, Safeners (WO 9706269), or it may also be advantageous to employ (6) organ-specific promoters.

For the purpose of expression in sink tissues of the plant, such as the tuber of the potato plant, the fruit of tomato, or the seed of soybean, canola, cotton, Zea mays, wheat, rice, and barley, it is preferred that the promoters utilized in the present invention have relatively high expression in these specific tissues. A number of promoters for genes with tuber-specific or -enhanced expression are known, including the class I patatin promoter, the promoter for the potato tuber ADPGPP genes, both the large and small subunits, the sucrose synthase promoter, the promoter for the major tuber proteins including the 22 kD protein complexes and proteinase inhibitors, the promoter for the granule bound starch synthase gene (GBSS), and other class I and II patatins promoters. Other promoters can also be used to express a protein in specific tissues, such as seeds or fruits. The promoter for β-conglycinin or other seed-specific promoters such as the napin and phaseolin promoters, can be used. A particularly preferred promoter for Zea mays endosperm expression is the promoter for the glutelin gene from rice, more particularly the Osgt-1 promoter. Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins, and the glutenins. Examples of such promoters in rice include those promoters for the ADPGPP subunits, the granule bound and other starch synthase, the branching enzymes, the debranching enzymes, sucrose synthases, and the glutelins. A particularly preferred promoter is the promoter for rice glutelin, Osgt-1 gene. Examples of such promoters for barley include those for the ADPGPP subunits, the granule bound and other starch synthase, the branching enzymes, the debranching enzymes, sucrose synthases, the hordeins, the embryo globulins, and the aleurone specific proteins.

Root specific promoters may also be used. An example of such a promoter is the promoter for the acid chitinase gene. Expression in root tissue could also be accomplished by utilizing the root specific subdomains of the CaMV 35S promoter that have been identified.

The 5' non-translated leader sequence can be derived from the promoter selected to express the heterologous gene sequence of the polynucleotide of the present invention, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. No. 5,362,865 and U.S. Pat. No. 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

At least four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. No. 4,945,050 and U.S. Pat. No. 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) are coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen, such as a strainless steel or Nytex screen, onto a filter surface covered with corn cells cultured in suspension. A particle delivery system suitable for use with the present invention is the helium acceleration PDS-1000/He gun, available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include particle gun delivery of DNA containing a selectable marker and targeting of the DNA to the plastid genome through homologous recombination (U.S. Pat. No. 5,451,513, U.S. Pat. No. 5,545,818, U.S. Pat. No. 5,877,402, U.S. Pat. No. 5,932,479, and WO 99/05265).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. No. 5,177,010, U.S. Pat. No. 5,104,310, U.S. Pat. No. 5,004,863, U.S. Pat. No. 5,159,135). Further, the integration of the T-DNA is a relatively precise process resulting in few rearrangements. The region of DNA to be transferred is defined by the border sequences, and intervening DNA is usually inserted into the plant genome.

Modern *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells; culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. 5,004,863, U.S. Pat. No. 5,159,135, U.S. Pat. No. 5,518,908); soybean (U.S. Pat. No. 5,569,834, U.S. Pat. No. 5,416,011); *Brassica* (U.S. Pat. No. 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, Canadian Patent Application No. 2,092,588, Australian Patent Application No 61781/94, Australian Patent No 667939, U.S. Pat. No. 6,100,447, International Patent Application PCT/US97/10621, U.S. Pat. No. 5,589,617, U.S. Pat. No. 6,541,257, and other methods are set out in Patent specification WO99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts.

The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Transgenic Non-Human Animals

A "transgenic non-human animal" refers to an animal, other than a human, that contains a gene construct ("transgene") not found in a wild-type animal of the same species or breed. A "transgene" as referred to herein has the normal meaning in the art of biotechnology and includes a genetic sequence which has been produced or altered by recombinant DNA or RNA technology and which has been introduced into an animal cell. The transgene may include genetic sequences derived from an animal cell. Typically, the transgene has been introduced into the animal by human manipulation such as, for example, by transformation but any method can be used as one of skill in the art recognizes.

Techniques for producing transgenic animals are well known in the art. A useful general textbook on this subject is Houdebine, Transgenic animals—Generation and Use (Harwood Academic, 1997).

Heterologous DNA can be introduced, for example, into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals.

Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology. Using this method, fibroblasts from donor animals are stably transfected with a plasmid incorporating the coding sequences for a binding domain or binding partner of interest under the control of regulatory sequences. Stable transfectants are then fused to enucleated oocytes, cultured and transferred into female recipients.

Compositions

Compositions of the present invention can include excipients, also referred to herein as "acceptable carriers". An excipient can be any material that the animal, plant, plant or animal material, or environment (including soil and water samples) to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal or o-cresol, formalin and benzyl alcohol. Excipients can also be used to increase the half-life of a composition, for example, but are not limited to, polymeric controlled release vehicles, biodegradable implants, liposomes, bacteria, viruses, other cells, oils, esters, and glycols.

Furthermore, a polypeptide described herein can be provided in a composition which enhances the rate and/or degree of degradation of benzimidazole carbamate fungicides, carbanilate fungicides, sulfonamide herbicides, thioamide herbicides and/or synthetic pyrethroid insecticides, or increases the stability of the polypeptide. For example, the polypeptide can be immobilized on a polyurethane matrix (Gordon et al., 1999), or encapsulated in appropriate liposomes (Petrikovics et al., 2000a and b). The polypeptide can also be incorporated into a composition comprising a foam such as those used routinely in fire-fighting (LeJeune et al., 1998). As would be appreciated by the skilled addressee, the polypeptide of the present invention could readily be used in a sponge or foam as disclosed in WO 00/64539.

One embodiment of the present invention is a controlled release formulation that is capable of slowly releasing a composition of the present invention into an animal, plant, animal or plant material, or the environment (including soil and water samples). As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Preferred controlled release formulations are biodegradable (i.e., bioerodible).

A preferred controlled release formulation of the present invention is capable of releasing a composition of the present invention into soil or water which is in an area comprising benzimidazole carbamate fungicides, carbanilate fungicides, sulfonamide herbicides, thioamide herbicides and/or synthetic pyrethroid insecticides. The formulation is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

The concentration of the polypeptide, vector, bacteria, extract, supernatant, host cell etc of the present invention that will be required to produce effective compositions for degrading benzimidazole carbamate fungicides, carbanilate fungicides, sulfonamide herbicides, thioamide herbicides and/or synthetic pyrethroid insecticides, will depend on the nature of the sample to be decontaminated, the concentration of the benzimidazole carbamate fungicides, carbanilate fungicides, sulfonamide herbicides, thioamide herbicides and/or synthetic pyrethroid insecticides, in the sample, and the formulation of the composition. The effective concentration of the polypeptide, vector, or host cell within the composition can readily be determined experimentally, as will be understood by the skilled artisan.

Enzymes of the invention, and/or microorganisms encoding therefor, can be used in coating compositions as generally described in WO 2004/112482 and WO 2005/26269.

Extracts and Supernatants

Extracts can be prepared using any technique known in the art as long as the desired activity is not abolished. Suitable methods include with no limitation: extended freeze-drying, grinding in the presence of silica or zirconium beads, use of the so-called "French press", sonication and gamma-rays irradiation.

For example, extended freeze-dried bacterial preparation means that essentially all the water has been removed from said preparation; thus, the extended freeze-dried bacterial preparation contains less than 1.5% of residual water, preferably less than 1% and more preferably less than 0.5%. However, in non-optimal freeze-drying conditions, when the preparations of freeze-dried bacteria contain more residual water (about 10%), i.e. all the bacteria are not killed. If required, killing of the residual living bacteria is alternatively obtained by contacting said preparations with air (atmospheric pressure); such preparations have the same properties and activity as the above described extended freeze-dried bacterial preparations. The residual water in the extended freeze-dried bacterial preparation is for instance determined by the coulometric method of Karl Fisher.

Extracts of the invention can be cell lysates.

Supernatants of the invention can be obtained by culturing the *Nocardioides* sp. under suitable conditions. Such conditions include nutrient media (also known as basal or complete media) that contains a carbon source such as glucose for bacterial growth, water, various salts need for bacterial growth and a source of amino acids and nitrogen (e.g., beef, yeast extract). This is an undefined medium because the amino acid source contains a variety of compounds with the exact composition unknown. Nutrient media contain all the elements that most bacteria need for growth and are non-selective, so they are used for the general cultivation and maintenance of bacteria kept in laboratory culture collections. In particular, any rich media like NB, LB, TB, or minimal media with or carbon and nitrogen added, can be used.

Minimal medium (MM) for growth of strain SG-4G can be prepared by dissolving following compounds in a litre of double distilled water: 4.0 g $Na_2HPO_4$, 2.0 g $KH_2PO_4$, 0.8 g $(NH_4)_2SO_4$, 0.8 g $MgSO_4.7H_2O$. Trace element solution (1 ml) is added to the solution after above mentioned compounds were dissolved completely; one liter of the trace element solution contained 0.10 g $Al(OH)_3$, 0.05 g $SnCl_2.2H_2O$, 0.05 g KI, 0.05 g LiCl, 0.08 g $MgSO_4$, 0.05 g $H_3BO_3$, 0.10 g $ZnSO_4.7H_2O$, 0.01 g $CoCl_2$, 0.01 g $NiSO_4.6H_2O$, $BaCl_2$ 0.05 g, 0.05 g $(NH_4)_6Mo_7O_{24}.4H_2O$. The pH of MM is adjusted to 7.0 before autoclaving at 15 lbs for 15 min.

The bacteria can be cultured at least at a temperature ranging from 20° C. (slow growth) to 37° C. (fast growth) in the presence of oxygen in baffled shake flasks shaking at, for example, 150-300 RMP ($OD_{600}$ up to).

Supernatant can be prepared using standard techniques, such as following culturing using centrifugation to collect the cellular material.

Extracts and/or supernatants of the invention include those which have at least been partially purified (also referred to herein as fractions). Such purification includes removing contaminating DNA and/or RNA, lipids, carbohydrates and proteins which do not possess the desired activity. Any purification procedures known in the art can be used.

Micro-organism Deposit Details

*Nocardioides* sp. SG-4G was deposited on 20 Jun. 2007 with the National Measurement Institute, 51-65 Clarke Street, South Melbourne, Victoria 3205, Australia under accession number V07/015,486.

This deposit was made under the provisions of the Budapest Treaty on the International Recognition of the Deposit of Microorganisms for the Purpose of Patent Procedure and the Regulations thereunder. This assures maintenance of viable cultures for 30 years from the date of deposit. The organisms will be made available by the National Measurement Institute under the terms of the Budapest Treaty which assures permanent and unrestricted availability of the progeny of the culture to the public upon issuance of the pertinent patent.

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

Antibodies

The term "antibody" as used in this invention includes polyclonal antibodies, monoclonal antibodies, bispecific antibodies, diabodies, triabodies, heteroconjugate antibodies, chimeric antibodies including intact molecules as well as fragments thereof, such as Fab, $F(ab')_2$, and Fv which are capable of binding the epitopic determinant, and other antibody-like molecules.

The term "specifically binds" refers to the ability of the antibody to bind to at least one polypeptide of the present invention but not other known proteins, in particular the proteins provided as SEQ ID NOs 14 to 43.

If polyclonal antibodies are desired, a selected mammal (e.g., mouse, rabbit, goat, horse, etc.) is immunised with an immunogenic polypeptide of the invention. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals.

Monoclonal antibodies directed against polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

Other techniques for producing antibodies of the invention are known in the art.

Antibodies of the invention may be bound to a solid support and/or packaged into kits in a suitable container along with suitable reagents, controls, instructions and the like.

In an embodiment, antibodies of the present invention are detectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further, exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like. Preferably, the detectable label allows for direct measurement in a plate luminometer, for example, biotin. Such labeled antibodies can be used in techniques known in the art to detect polypeptides of the invention.

EXAMPLES

Example 1

Materials and Methods

LC-MS assay

Before benzimidazole carbamate-degrading enzymes could be either evolved in vitro or identified and isolated from microorganisms, it was necessary to develop an appropriate hydrolysis assay for a representative pesticide, such as carbendazim (MBC). The inventors had difficulties in standardizing a spectrophotometric assay for carbendazim degradation since carbendazim and its metabolite, 2-aminobenzimidazole, had the same absorption spectrum. Therefore, an LC-MS assay for carbendazim degradation was developed.

An Agilent series LC system controlled by Agilent TOF Software (Version A.01.00) was used (Agilent Technologies). The mobile phase consisted of acetonitrile:water (18:82 v/v, and both containing 0.1% v/v formic acid). It was pumped at a flow rate of 0.7 mL min$^{-1}$. The column employed was a Aqua® C18, 5 µm-particle size, 250×4.60 mm (Phenomenex) and was operated at 25° C. The photodiode array detector was operating at a wavelength of 270 nm.

The MS analysis was performed using an LC/MSD TOF mass spectrometer (Agilent Technologies) with an ESI source. The mass spectrometer was connected to the HPLC stream after DAD detector. The scanning mode was in the positive ion mode. Nitrogen was flowing at a rate of 12 l min$^{-1}$ as a drying gas. The capillary temperature was 350° C. and the spray voltage was 3 kv. For MS-TOF scans in the range of 50-300 m/z, the fragmenter and Skimmer were set at 120 V and 60 V, respectively.

High Throughput (HTP) Plate-Clearing Assay for Carbendazim Degradation

A HTP assay for carbendazim degradation was used for screening cosmid or plasmid libraries of carbendazim degrading bacterial strains. In this assay minimal media plates containing 0.7% agarose were sprayed with 0.1% carbendazim as an emulsion in diethyl ether and dried overnight for complete evaporation of the diethyl ether. A 3 µl drop of bacterial culture, grown overnight in nutrient broth, was transferred onto the carbendazim sprayed plate. Clearing around a culture drop indicated carbendazim hydrolytic activity because the hydrolysis product of carbendazim is highly soluble compared with carbendazim (soluble at 8 ppm only).

Resting Cell Assays

E. coli clones were grown overnight in 15 ml LB with appropriate antibiotics. The cells were then collected by centrifugation, washed twice with 50 mM phosphate buffer (pH 7.0) and finally resuspended in 3 ml minimal media containing 8 ppm of carbendazim. Samples were collected over time and culture supernatants tested for production of 2-AB using LC-MS.

Isolation of Mixed Microbial Cultures Degrading Pesticides

The first stage in the development of microbial enzymes that degrade benzimidazole carbamate pesticides like carbendazim was the isolation of mixed microbial cultures obtained from contaminated environments that can degrade the pesticide. Isolation proceeded by successive solid and liquid phase enrichment culturing of inocula from the contaminated environments on media in which the carbendazim must be degraded to provide the carbon or nitrogen required for growth.

Purification and Identification of Microbial Species Degrading Pesticides

Purification of carbendazim-degrading bacterial cultures were undertaken by end-point dilution subculturing from the liquid phase enrichments obtained as described above. Once pure cultures were obtained the bacteria were identified by 16S rDNA sequencing.

Characterisation of Gene/Enzyme Systems in Purified Cultures Responsible for Pesticide Degradation Activities of the purified cultures were first characterised in terms of metabolites generated, using the LC-MS assay. This was necessary to ensure that the relevant culture achieved substantial single step detoxification of the pesticide. The next step was to compare strains to isolate the most efficient degrader, from which the gene/enzyme system responsible for carbendazim detoxification would then be cloned. Alternatively, the organism itself can be used as a radiation-killed whole cell product for carbendazim degradation.

Cloning of the Gene/Enzyme System Responsible for Pesticide Degradation

Libraries of total bacterial genomic DNA were prepared in either pUC18 or pYUB415, which is an E coli-Mycobacterium cosmid shuttle vector. Libraries were screened for gain-of-function (carbendazim transformation to 2-AB) in E. coli and/or Mycobacterium smegmatis, using above mentioned assays.

Standard protein purification strategies such as molecular weight cut-off membranes and ion exchange chromatography were attempted to obtain a pure enzyme catalysing the transformation of carbendazim to 2-AB.

The N-terminus of the pure enzyme and also an internal peptide were sequenced commercially from The Australian Proteome Analysis Facility, Macquarie University, NSW. These sequences were used to design PCR primers to amplify a part of the gene to be used as a probe with which to clone the full-length gene.

Example 2

Soil Enrichments

Soil samples were collected from a local golf course that routinely used carbendazim as a fungicide. Enrichment cultures were then set up using carbendazim as the sole source of carbon or nitrogen, under both aerobic and anaerobic conditions. Several aerobic soil enrichments yielded mixed cultures with carbendazim degrading activity. A pure carbendazim degrading bacterium, Nocardioides sp. SG-4G, was then isolated several times from different enrichments and later identified on the basis of the sequence of its 16S rRNA gene. The sequence of the 16S rRNA gene which was characterized is provided as SEQ ID NO:4.

This strain utilized carbendazim as a sole source of carbon and nitrogen. Resting cell studies demonstrated the complete disappearance and mineralisation of 8 ppm carbendazim in as little as three minutes. This represents extremely rapid turn-over of the pesticide and was a very promising indication that the enzyme responsible would be an effective bioremediant.

Strain SG-4G had 99% identity with several Nocardioides sps. (nitrophenolicus, panaciterrae, kongjuensis). This level of identity confirms that newly isolated bacterium belongs to the genus Nocardioides.

Example 3

Biochemical Characterization of the Carbendazim Catabolic Pathway

Results of resting cell studies and enzyme assays confirmed that carbendazim is hydrolysed by a secreted enzyme to 2-aminobenzimidazole (2-AB), which is further degraded to 2-hydroxybenzimidazole (2-HB). These metabolites were identified on the basis of their retention times in HPLC and m/z in LC-MS, which matched exactly those of authentic standards. The pathway for initial degradation of carbendazim by the strain is shown in FIG. 2.

Example 4

Cloning the Gene Responsible for Carbendazim Degradation in SG-4G

HTP Plate-Clearing Assay

A HTP plate-clearing assay for carbendazim degradation was developed as a screening tool for cloning the gene responsible for activity. The assay is illustrated in FIG. 3.

Activity Screening

Preliminary data comparing the carbendazim degrading activity of culture supernatants and whole cells suggested that the enzyme responsible for conversion of carbendazim to 2-AB in Nocardioides sp. SG-4G was co-factor independent and secreted into the growth medium. While a large plasmid (pSG4G) was present in strain SG-4G, plasmid curing experiments designed to test if the activity were plasmid encoded were inconclusive. Two separate plasmid libraries in E. coli (in pBluescript) were therefore constructed, one from the SG-4G plasmid (pSG-4G) and the other from total DNA isolated from strain SG-4G.

Approximately 2000 clones (insert size of 6-10 kb) were screened using the HTP plate-clearing assay. None of them was found to be positive. It is important to note here that the HTP plate-clearing assay was developed on the basis of the secretion of the carbendazim hydrolysing enzyme from a wild-type Gram positive strain. Gene expression and/or enzyme secretion differences in Gram negative E. coli could be responsible for the lack of a positive result, assuming that the number of clones screened was enough to represent the genome.

A cosmid library (insert size ~40 kb) was also prepared in an E. coli-Mycobacterium shuttle vector and all 520 clones screened using the resting cell assay. Again, no positive clones were obtained.

The cosmid library was then screened in Mycobacterium smegmatis, a Gram positive strain. Approximately 500 cosmid clones were screened twice in M smegmatis for carbendazim degradation; no positives clones were identified.

Transposon Mutagenesis

Attempts to clone the carbendazim-degrading gene-enzyme system using a transposon mutagenesis approach were unsuccessful. The Nocardioides genus is not well characterized in terms of the complex molecular biology required to carry out experiments like transposon mutagenesis and functional cloning (i.e. transposons have yet to be identified for this genus and there are no electroporation protocols published in the literature). Nonetheless, the inventors attempted to generate transposon mutants based on established protocols for other Gram positive bacterial systems, but to no avail.

Reverse Genetics

The inventors developed a two-step protein purification protocol to purify the carbendazim hydrolysing enzyme from strain SG-4G. The first step involved the use of molecular weight cut-off membranes (100 kD and 50 kD, which separated proteins based on size and shape), while the second step involved ion exchange chromatography. Fractions showing carbendazim hydrolytic activity also demonstrated esterase activity when naphthyl acetate was used as a substrate (FIG. 4). Ion exchange chromatography revealed a substantially pure protein of ~25 kD molecular weight (FIG. 5).

The N-terminus of the purified protein and one internal peptide (from a trypsin digest of the purified protein) were sequenced to reveal 15 (ANFVLVHGAWHGGWC) (SEQ ID NO:5) and 11 (LVYLDAFVPEH) (SEQ ID NO:6) amino acid residues, respectively. These sequences aligned extremely well with esterases and other members of the alpha/beta hydrolase fold superfamily of proteins. Based on sequenced amino acids residues, PCR primers were designed to clone the partial gene, which can be used as a probe to clone the full length gene.

Cloning of the Complete Gene

Based on the N-terminus and internal peptide sequences of the carbendazim degrading enzyme degenerate primers F1 (5' ATGGCCAACTTCGTCCTCGTGC) (SEQ ID NO:7) and R2 (5' GACGAAGGCGTCGAGGTAGACC) (SEQ ID NO:8) were designed based on the codon usage of Nocardioides sp. The partial gene was amplified using these primers and genomic DNA (gDNA) of Nocardioides sp. SG-4G. For PCR amplification, approximately 375 ng gDNA from Nocardioides sp. SG-4G, 50 µmol of each primer, 5 µl of 10×PCR buffer with $MgSO_4$, and 1 U of Deep Vent DNA polymerase (NEB Biolabs, USA) were added. The PCR cycle protocol was denaturation at 98° C. for 5 min, followed by 30 cycles of 98° C. for 30 s, 48° C. for 30 sec and 75° C. for 30 sec. A final extension step of 5 min at 75° C. was also used. The resulting PCR products were sequenced commercially at Micromon DNA Sequencing Facility (Monash University, Victoria 3800 Australia). One of the PCR products showed alpha beta hydrolases domains in the Conserved Domain Database search. DNA sequencing primers were designed based on this sequence. Three sequencing primers, namely F2-214 (5' ATCCTCGTCGGCCATTCGTAC) (SEQ ID NO:9), F3-277 (5' AAGATCAGGTCGCTGGTCTACCTC) (SEQ ID NO:10) and R-466 (5' GTTCACCCAGTCGCGCTTGTC) (SEQ ID NO:11), were designed for direct sequencing using the gDNA of Nocardioides sp. SG-4G. The direct gDNA sequencing was performed commercially by Micromon DNA Sequencing Facility. The sequencing results yielded the complete gene, the open reading frame of which is provided as SEQ ID NO:2). The enzyme has been named MheI (MBC-hydrolysing enzyme) (amino acid sequence provided as SEQ ID NO:1). The 729 by gene (including stop codon) has a G+C content of 69.6% and encodes a 242 amino acids protein (26.327 kDa).

An alignment of MheI with esterases and other members of the alpha/beta hydrolase fold superfamily of proteins is provided in FIG. 6.

Example 5

Expression of MheI

A codon optimized mheI for expression in E. coli was commercially synthesized by GENEART AG (BioPark, Josef-Engert-Str. 11, D-93053 Regensburg Germany) (SEQ ID NO:3). GENEART provided the codon optimized mheI in pGA18 vector. The codon optimized gene was cloned into the Invitrogen Gateway Vector pDEST17 using manufacturers protocols (Invitrogen catalogue number 11824-026). In summary, codon optimized mheI was PCR amplified with attB1 (GGGGACAAGTTTGTACAAAAAAGCAG-GCTTAATGGCGAACTTTGTGCTG) (SEQ ID NO:12) and attB2 (GGGGACCACTTTGTACAAGAAAGCTGGG-TATTATCAGCCCAGCGCGGC) (SEQ ID NO:13) primers. For PCR amplification, approximately 20 ng plasmid (pGA18 containing codon optimized mheI), 0.2 uM of each primer, 5 µl of 10×PCR buffer, 1 µl of dNTPs 10 mM, and 2 U of Deep Vent DNA polymerase (NEB Biolabs, USA) were added. The PCR cycle protocol was initial denaturation at 98° C. for 3 min, followed by 5 cycles of 98° C. for 20 s, 48° C. for 20 sec and 75° C. for 1 min then 25 cycles at 98° C. 20 s, 60° C. 20 s, 75° C. 1 min. A final extension of step of 5 min at 75° C. was also used. The amplicon was cloned into pDONOR201 (Invitrogen) using the BP reaction as described in the above mentioned kit protocol. Finally the mheI was cloned into the pDEST17 (final construct is named as pDEST17-mheI, see FIG. 7) by recombining the BP reaction generated pDONOR201 (containing mheI) into pDEST17 by the LR recombination reaction.

For mheI expression from pDEST17-mheI the protocol provided with the Gateway Cloning Kit (Invitrogen catalogue number 11824-026) was followed and the only exception was that expression occurred at 20° C. Cells were harvested by centrifugation at 24 h after induction with arabinose. The cell pellet (4.26 g) from a 250 ml culture was lysed by resuspending into 40 ml of Bugbuster solution (Invitrogen catalogue number 7091) and rotated slowly for 30 min at 22° C. The lysate was centrifuged at 16,000 g for 20 min at 4° C. to remove the cell debris and insoluble protein. The soluble protein was bound and eluted from a His Column (Qiagen catalogue number 30760) according to the manufacturers instructions. After elution from the column the protein was dialyzed against two changes of 200 mM sodium phosphate buffer pH 7.2 and the purified protein was stored at 4° C. Protein expression and purification was confirmed by the presence of an approximately ~29 kDa band in SDS-PAGE (FIG. 8).

Example 6

Enzyme Assays and Determination of Kinetic Constants

Enzyme assays were performed in 96 well microtiter plates (Agilent catalogue number) at 22° C. The assay mixture typically contained 20 µg bovine serum albumin, 0.022 µg purified MheI and 1-40 µM carbendazim in a final volume of 200 µl of 200 mM sodium phosphate buffer. Enzymatic reaction was stopped by adding 5 µl of formic acid after 10 minutes and the initial velocities were measured using HPLC. All these assays were performed in triplicate.

$K_m$ and $V_{max}$ values from enzyme-kinetic data for MheI for carbendazim were determined using version 1.3 Sigma Plot Kinetic Module (FIG. 9). For carbendazim, MheI has a $K_m$ of 6.1 µM and turnover number of 120 per second.

Example 7

Activity of SG-4G Against Synthetic Pyrethroids

A semi-purified protein sample (the SG-4G 30 kD retentate) was used to assay SG-4G activity against synthetic pyrethroid (SP) substrates.

Two 800 ml Nutrient Broth cultures were seeded with 1% SG-4G and incubated at 37° C. for 36 hours with shaking at 150 rpm. Cells were washed three times in 20 mM $Na_2PO_4$ buffer pH 7.0 at 4° C. and resuspended in 100 ml 20 mM $Na_2PO_4$ buffer pH 7.0 (ie these are "resting cells"). 1 ml 10 mM glucose (carbon source) and 10% $NH_4Cl$ (nitrogen source) were added to the suspension, which was then incubated overnight 37° C. with shaking at 50 rpm. The resting cell culture was precitated and the supernatant passed through a 0.22 µm filter. The filtered supernatant was then passed through the following series of size selection and concentrating Amicon centrifugal filters: 100 kD, 50 kD, 30 kD and 10 kD. The 30 kD retentate (ie that sample containing proteins in the size range of 30-50 kD) was assayed for carbendazim degrading activity and shown to have activity. Samples were stored at 4° C. until required.

The SG-4G 30 kD retentate was assayed for activity against SP substrates using the single-isomer fluorogenic analogues and methods of Huang et al. (2005).

The fluorogenic SP analogues and their abbreviated names are as follows:

(S)-α-Cyano-(6-methoxy naphthalen-2-yl)methyl (1R) cis-3-(2,2-Dichlorovinyl)-2,2-dimethylcyclopropanecarboxylate mCNMP 1(R)cis-α(S)

(S)-α-Cyano-(6-methoxy naphthalen-2-yl)methyl (1S) cis-3-(2,2-Dichlorovinyl)-2,2-dimethylcyclopropanecarboxylate mCNMP 1(S)cis-α(S)

(S)-α-Cyano-(6-methoxynaphthalen-2-yl)methyl (1R) trans-3-(2,2-Dichlorovinyl)-2,2-dimethylcyclopropanecarboxylate mCNMP 1(R)trans-α(S)

(S)-α-Cyano-(6-methoxynaphthalen-2-yl)methyl (1S) trans-3-(2,2-Dichlorovinyl)-2,2-dimethylcyclopropanecarboxylate mCNMP 1(S)trans-α(S)

(R)-α-Cyano-(6-methoxynaphthalen-2-yl)methyl (1R) cis-3-(2,2-Dichlorovinyl)-2,2-dimethylcyclopropanecarboxylate mCNMP 1(R)cis-α(R)

(R)-α-Cyano-(6-methoxynaphthalen-2-yl)methyl (1S) cis-3-(2,2-Dichlorovinyl)-2,2-dimethylcyclopropanecarboxylate mCNMP 1(S)cis-α(R)

(R)-α-Cyano-(6-methoxynaphthalen-2-yl)methyl (1R)trans-3-(2,2-Dichloro vinyl)-2,2-dimethylcyclopropanecarboxylate mCNMP 1(R)trans-α(R)

(R)-α-Cyano-(6-methoxynaphthalen-2-yl)methyl (1S)trans-3-(2,2-Dichloro vinyl)-2,2-dimethylcyclopropanecarboxylate mCNMP 1(S)trans-α(R)

(R)-α-Cyano-(6-methoxynaphthalen-2-yl)methyl (2R)-(4-Chlorophenyl)-3-methylbutanoate mCNMF 2(R)-α(R)

(S)-α-Cyano-(6-methoxynaphthalen-2-yl)methyl (2R)-(4-Chlorophenyl)-3-methylbutanoate mCNMF 2(R)-α(S)

(R)-α-Cyano-(6-methoxynaphthalen-2-yl)methyl (2S)-(4-Chlorophenyl)-3-methylbutanoate mCNMF 2(S)-α(R)

(S)-α-Cyano-(6-methoxynaphthalen-2-yl)methyl (2S)-(4-Chlorophenyl)-3-methylbutanoate mCNMF 2(S)-α(S)

The mCNMP fluorogenic isomers are analogues of the isomers found in various cypermethrin, deltamethrin and cyhalothrin insecticidal formulations, whereas the mCNMF fluorogenic isomers are analogues of isomers found in fenvalerate or esfenvalerate.

Briefly, 20 µM substrate solutions were made in glass by carefully mixing 1 volume of 2 mM substrate (in DMSO) into 99 volumes of 25 mM Tris-HCl, pH8.0. 100 µL of each 20 µM substrate solution was added to separate wells of a white 96-well FluoroNUNC plate and the plate equilibrated to 30° C. in a BMG POLARstar fluorescence reader. Cellular extract was diluted into 25 mM Tris-HCl, pH8.0, 50 µg/mL BSA pre-warmed to 30° C. Reactions were commenced by adding 100 µL of diluted extract to the sample wells of the assay plate and the reaction monitored at an excitation wavelength of 340 nm and an emission wavelength of 460 nm.

It can be seen from FIG. 10 that the SG-4G protein extract had significant activity for mCNMP 1(R)cis-α(S), mCNMP 1(S)trans-α(S) and mCNMP 1(R)trans-α(R), and measureable activity for several other isomers. No activity was recorded for mCNMP 1(S)trans-α(R) and mCNMF 2(R)-α(R). A schematic representation of synthetic pyrethroid degradation is provided in FIG. 11.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 60/947,147 and AU 2007903522 both filed 29 Jun. 2007, the entire contents of which are incorporated herein in their entirety by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

References

Abdullah et al. (1986) Biotechnology 4:1087.
Bornscheuer (2002) FEMS Microbiol. Rev. 26:73-81.
Capecchi (1980) Cell 22:479-488
Cheng et al. (1996) Plant Cell Rep. 15:653-657.
Clapp (1993) Clin. Perinatol. 20:155-168.
Curiel et al. (1992) Hum. Gen. Ther. 3:147-154.
Derbyshire (1987) J. Agr. Food Chem. 35:871-877.
Eglitis et al. (1988) Biotechniques 6:608-614.
Fujimura et al. (1985) Plant Tissue Cultural Letters 2:74.
Gordon et al. (1999) Chemical-Biological Interactions 14:463-470.
Graham et al. (1973) Virology 54:536-539.
Grant et al. (1995) Plant Cell Rep. 15:254-258.
Harayama (1998). Trends Biotechnol. 16:76-82.
Hayatsu et al. (2001) MFEMS Microbiol. Lett. 201:99-103.
Huang et al. (2005) Chem. Res. Toxicol. 18:516-527.
Jing-Liang et al. (2006) Curr Microbiol. 53:72-76.
Karns et al. (1986) Pestic. Biochem. Physiol. 25:211-217.
Karns et al. (1991) J. Agric. Food Chem. 39:1004-1008.
Koziel et al. (1996) Plant Mol Biol. 32:393-405.
LeJuene et al. (1998) Nature 395:27-28.
Lu et al. (1993) J. Exp. Med. 178:2089-2096.
Needleman and Wunsch (1970) J. Mol Biol. 45:443-453.
Petrikovics et al. (2000a) Toxicology Science 57:16-21.
Petrikovics et al. (2000b) Drug Delivery 7:83-89.
Tomasek (1989) J Bacteriol. 171:4038-4044.
Topp et al. (1993) Appl. Environ. Microbiol. 59:3339-3349.
Toriyama et al. (1986) Theor. Appl. Genet. 205:34.
Wagner et al. (1992) Proc. Natl. Acad. Sci. USA 89:6099-6103.
Yarden et al. (1990) Can. J. Microbiol. 36:15-23.
Zhang et al. (2005) World. J Microbiol Biotechnol 21:265-269.

The invention claimed is:

1. A composition comprising:
   a *Nocardioides* sp.,
   an extract of the *Nocardioides* sp., or
   a culture supernatant of the *Nocardioides* sp., wherein the extract and the culture supernatant degrades a benzimidazole carbamate fungicide, a carbanilate fungicide, and/or a synthetic pyrethroid insecticide, and
   wherein the *Nocardioides* sp. is strain SG-4G deposited under Accession number V07/015486 on 20 Jun. 2007 at the National Measurement Institute, Australia.

2. The composition of claim 1, wherein the benzimidazole carbamate fungicide is carbendazim.

3. The composition of claim 1, wherein the composition comprises a fraction of the extract.

4. The composition of claim 1, wherein the composition comprises a fraction of the supernatant.

5. An isolated strain of *Nocardioides* sp. which is strain SG4G deposited under Accession number V07/015486 on 20 Jun. 2007 at the National Measurement Institute, Australia.

6. An extract or a culture supernatant of the isolated strain of claim 5, wherein the extract and the culture supernatant degrades a benzimidazole carbamate fungicide, a carbanilate fungicide, and/or synthetic pyrethroid insecticide.

7. A fraction of the extract of claim 6.

8. A fraction of the supernatant of claim 6.

9. A substantially purified polypeptide comprising amino acids comprising the sequence provided as SEQ ID NO:1, an enzymatically active fragment thereof, or an amino acid sequence which is at least 95% identical to SEQ ID NO:1, wherein the polypeptide degrades a benzimidazole carbamate fungicide and/or a carbanilate fungicide.

10. The polypeptide of claim 9 which comprises an amino acid sequence which is at least 99% identical to SEQ ID NO:1.

11. The polypeptide according to claim 9, which is a fusion protein further comprising at least one other polypeptide sequence.

12. The polypeptide of claim 9, wherein the polypeptide is a recombinant polypeptide.

13. A polymeric sponge or foam for degrading a benzimidazole carbamate fungicide and/or a carbanilate fungicide, the foam or sponge comprising the polypeptide according to claim 9 immobilized on a polymeric porous support.

14. An isolated polynucleotide comprising:
   i) the sequence of nucleotides as provided in SEQ ID NO:2 or SEQ ID NO:3,
   ii) a sequence of nucleotides encoding the polypeptide according to claim 9,
   iii) a sequence of nucleotides which is at least 95% identical to i), or
   iv) a sequence of nucleotides complementary to any one of i) to iii).

15. A vector comprising the polynucleotide of claim 14.

16. A host cell comprising the polynucleotide of claim 14.

17. A method of producing a polypeptide comprising amino acids having the sequence provided as SEQ ID NO:1, an enzymatically active fragment thereof, or an amino acid sequence which is at least 95% identical to SEQ ID NO:1, wherein the polypeptide degrades a benzimidazole carbamate fungicide, and/or a carbanilate fungicide, the method comprising cultivating the host cell according to claim 16 under conditions which allow expression of the polynucleotide encoding the polypeptide, and recovering the expressed polypeptide.

18. An extract of a host cell of claim 16, wherein the extract comprises a polypeptide comprising amino acids comprising the sequence provided as SEQ ID NO:1, an enzymatically active fragment thereof, or an amino acid sequence which is at least 95% identical to SEQ ID NO:1, wherein the polypeptide degrades a benzimidazole carbamate fungicide, and/or a carbanilate fungicide.

19. A composition which degrades a benzimidazole carbamate fungicide, and/or a carbanilate fungicide, the composition comprising:
   a polypeptide comprising amino acids comprising the sequence provided as SEQ ID NO:1, an enzymatically active fragment thereof, or an amino acid sequence which is at least 95% identical to SEQ ID NO:1, wherein the polypeptide degrades a benzimidazole carbamate fungicide and/or a carbanilate fungicide; and/or an extract or a culture supernatant of the host cell of claim 16, wherein the extract and the culture supernatant degrades a benzimidazole carbamate fungicide, a carbanilate fungicide, and/or synthetic pyrethroid insecticide.

20. The composition of claim 19, wherein the composition comprises a fraction of the extract.

21. The composition of claim 19, wherein the composition comprises a fraction of the supernatant.

22. A method for degrading a benzimidazole carbamate fungicide, a carbanilate fungicide, and/or a synthetic pyrethroid insecticide, the method comprising:
  contacting the benzimidazole carbamate fungicide, carbanilate fungicide, and/or synthetic pyrethroid insecticide with the composition of claim 1.

23. The method of claim 22, wherein the composition comprises a fraction of the extract.

24. The method of claim 22, wherein the composition comprises a fraction of the supernatant.

25. A method of producing a polypeptide with enhanced ability to degrade a benzimidazole carbamate fungicide, and/or a carbanilate fungicide, or altered substrate specificity for a different type of benzimidazole carbamate fungicide and/or carbanilate fungicide, the method comprising
  (i) altering one or more amino acids of the polypeptide according to claim 9,
  (ii) determining the ability of the altered polypeptide obtained from step (i) to degrade a benzimidazole carbamate fungicide and/or a carbanilate fungicide, and
  (iii) selecting an altered polypeptide with enhanced ability to degrade a benzimidazole carbamate fungicide and/or a carbanilate fungicide, or altered substrate specificity for a different type of benzimidazole carbamate fungicide and/or carbanilate fungicide, when compared to the polypeptide used in step (i).

26. A method for degrading a benzimidazole carbamate fungicide, a carbanilate fungicide, and/or a synthetic pyrethroid insecticide, the method comprising:
  contacting the benzimidazole carbamate fungicide and/or carbanilate fungicide with the composition of claim 19.

27. The method of claim 26, wherein the composition comprises a fraction of the extract.

28. The method of claim 26, wherein the composition comprises a fraction of the supernatant.

29. A method for degrading a benzimidazole carbamate fungicide, a carbanilate fungicide, and/or a synthetic pyrethroid insecticide, the method comprising:
  contacting the benzimidazole carbamate fungicide and/or carbanilate fungicide with the polypeptide of claim 9.

30. A method for degrading a benzimidazole carbamate fungicide, a carbanilate fungicide, and/or a synthetic pyrethroid insecticide, the method comprising:
  contacting the benzimidazole carbamate fungicide and/or carbanilate fungicide with the host cell of claim 16.

31. A method for degrading a benzimidazole carbamate fungicide, a carbanilate fungicide, and/or a synthetic pyrethroid insecticide, the method comprising:
  contacting the benzimidazole carbamate fungicide and/or carbanilate fungicide with the sponge or foam of claim 13.

* * * * *

SEQUENCE LISTING

```
<160> NUMBER OF SEQ ID NOS: 43

<210> SEQ ID NO 1
<211> LENGTH: 242
<212> TYPE: PRT
<213> ORGANISM: Nocardioides sp.
<220> FEATURE:
<223> OTHER INFORMATION: strain SG-4G

<400> SEQUENCE: 1

Met Ala Asn Phe Val Leu Val His Gly Ala Trp His Gly Gly Trp Cys
1               5                   10                  15

Tyr Arg Asp Thr Ala Ala Ala Leu Arg Lys Ala Gly His Arg Val Leu
                20                  25                  30

Thr Pro Thr His Thr Gly Val Gly Gln Arg Ala His Leu Ser Gly Glu
            35                  40                  45

Asn Val Thr Leu Glu Thr His Ile Arg Asp Val Leu Gly Cys Ile Glu
        50                  55                  60

Ala Glu Glu Leu Asp Asp Val Ile Leu Val Gly His Ser Tyr Gly Gly
65                  70                  75                  80

Met Val Ile Thr Gly Val Ala Asp Arg Ile Ala Pro Lys Ile Arg Ser
                85                  90                  95

Leu Val Tyr Leu Asp Ala Phe Val Pro Glu His Gly Asp Ser Leu Met
                100                 105                 110

Ala Leu Leu Pro Lys Ala Leu Pro Pro Glu Val Ser Ala Gln Phe Ile
            115                 120                 125

Gly Gly Phe His Ala Ala Leu Asp Lys His Cys Gly Leu Met Gln
        130                 135                 140

Pro Ile Pro Ala Glu Leu Phe Asn Val Val Ala Asp Lys Arg Asp Trp
145                 150                 155                 160

Val Asn Arg Arg Cys Val Pro Gln Ala Leu Ala Thr Tyr Glu Met Pro
                165                 170                 175

Leu Leu Leu Ala Gly Gly Gly Ser Ala Val Lys Gln Arg Val Tyr Ile
```

```
                    180                 185                 190
Leu Ala Asp Gly Trp Asp Pro Ser Pro Phe Arg Tyr Phe Ala Lys Leu
        195                 200                 205

Tyr Asp Gly Lys Pro Gly Trp Gln Val Val Lys Phe Pro Cys Gly His
    210                 215                 220

Asp Val Met Val Asp Met Pro Asn Glu Leu Ala Glu Lys Leu Ala Ala
225                 230                 235                 240

Leu Gly

<210> SEQ ID NO 2
<211> LENGTH: 729
<212> TYPE: DNA
<213> ORGANISM: Nocardioides sp.
<220> FEATURE:
<223> OTHER INFORMATION: strain SG-4G

<400> SEQUENCE: 2
atggccaact tcgtcctcgt gcacggcgcc tggcacggcg gctggtgcta tcgcgacacc      60
gccgccgcgc tgcgcaaggc cggccaccgc gtactgacgc cgacgcacac cggcgtcggg     120
cagcgcgcgc atctctcggg cgagaacgtg acgctcgaaa cgcacatccg cgacgtgctc     180
ggctgcatcg aggccgaaga gctcgacgac gtcatcctcg tcggccattc gtacggcggc     240
atggtgatca ccggcgtggc ggaccgcatc gcgccgaaga tcaggtcgct ggtctacctc     300
gacgccttcg tgccggagca cggcgactcg ctgatggctc tcctgcccaa ggcgctaccg     360
cctgaagtgt cggcgcaatt catcggcggc ttccacgcgg ccgcgctcga caagcactgc     420
ggcctgatgc agccgattcc ggccgaattg ttcaacgtcg ttgccgacaa cgcgactgg      480 gtgaaccggc gctgcgtgcc gcaggcgctc gccacctacg agatgccgct gctgctcgcg     540
ggaggcggca gcgcggtgaa gcagcgcgtc tacatcctgg ccgacggctg ggatccgagc     600
ccgttccgct acttcgcgaa gctgtacgac ggcaagcccg gctggcaggt cgtcaagttc     660
ccgtgcggcc acgacgtgat ggtcgacatg ccgaacgagc tggcggagaa gctggcggcg     720
ctgggctga                                                            729

<210> SEQ ID NO 3
<211> LENGTH: 729
<212> TYPE: DNA
<213> ORGANISM: Artificial Sequence
<220> FEATURE:
<223> OTHER INFORMATION: Codon optimized MheI polynucleotide sequence

<400> SEQUENCE: 3
atggcgaact ttgtgctggt gcatggcgcg tggcatggtg gctggtgcta tcgtgatacc      60
gcggcggcgc tgcgtaaagc gggccatcgt gtgctgaccc cgacccatac cggtgttggc     120
cagcgtgcgc atctgagcgg cgaaaacgtg accctggaaa cccatattcg tgatgtgctg     180
ggctgcattg aagcggaaga actggatgat gtgattctgg tgggtcacag ctacggcggc     240
atggtgatta ccggcgtggc ggatcgtatt gcgccgaaaa ttcgcagcct ggtgtatctg     300
gatgcgtttg tgccggaaca tggcgatagc ctgatggcgc tgctgccgaa agcgctgccg     360
ccggaagtga gcgcgcagtt tattggcggc tttcatgcgg cggccctgga taaacattgc     420
ggcctgatgc agccgattcc ggcggaactg tttaacgtgg tggcggataa cgtgattgg      480 gtgaaccgtc gttgcgttcc gcaggcgctg gccacctatg aaatgccgct gctgctggcc     540
ggtggtggta gcgcggtgaa acagcgtgtg tatattctgg ccgatggctg gaccccgagc     600
ccgtttcgtt attttgcgaa actgtacgat ggcaaaccgg gctggcaggt tgtgaaattt     660
```

```
ccgtgcggcc atgatgtgat ggtggatatg ccgaacgaac tggccgaaaa actggccgcg    720
ctgggctaa                                                             729
```

<210> SEQ ID NO 4
<211> LENGTH: 1448
<212> TYPE: DNA
<213> ORGANISM: Nocardioides sp.
<220> FEATURE:
<223> OTHER INFORMATION: strain SG-4G
<220> FEATURE:
<221> NAME/KEY: misc_feature
<222> LOCATION: 1198
<223> OTHER INFORMATION: n = A,T,C or G

<400> SEQUENCE: 4

```
agggcctaac acatgcaagt cgagcggaaa ggctccttcg ggggtactcg agcggcgaac     60
gggtgagtaa cacgtgagta atctgccctg tgctctggga tagccaccgg aaacggtgat    120
taataccgga tacgaccact ataggcatct gttggtggtg aaagttttt tcggcatggg     180 atgtgctcgc ggcctatcag cttgttggtg aggtaatggc tcaccaaggc tttgacgggt    240
agccggcctg agagggtgac cggtcacact gggactgaga cacggcccag actcctacgg    300
gaggcagcag tggggaatat tggacaatgg gcggaagcct gatccagcaa cgccgcgtga    360
gggatgacgg ccttcgggtt gtaaacctct ttcagtaccg acgaagcgaa agtgacggta    420
ggtacagaag aaggaccggc caactacgtg ccagcagccg cggtaatacg tagggtccga    480
gcgttgtccg gaattattgg gcgtaaaggg ctcgtaggcg gtttgtcgcg tcggagtgaa    540
aaacaccggg cttaactcgg tgcttgcttc cgatacgggc agactagagg tatgcagggg    600
agaatggaat tcctggtgta gcggtgaaat gcgcagatat caggaggaac accggtggcg    660
aaggcggttc tctgggcatt acctgacgct gaggagcgaa agtgtgggga cgaacagga    720 ttagataccc tggtagtcca caccgtaaac gttgggcgct aggtgtgggg cctattccat    780
gggttccgtg ccgtagctaa cgcattaagc gccccgcctg gggagtacgg ccgcaaggct    840
aaaactcaaa ggaattgacg ggggcccgca caagcggcgg agcatgcgga ttaattcgat    900
gcaacgcgaa gaaccttacc tgggtttgac atacaccgga agccccagA gatggggtc     960 tctttgatac tggtgtacag gtggtgcatg gctgtcgtca gctcgtgtcg tgagatgttg   1020
ggttaagtcc cgcaacgagc gcaaccctcg ttccatgttg ccagcgggtt atgccgggga  1080
ctcatgggag actgccgggg tcaactcgga ggaaggtggg gatgacgtca agtcatcatg   1140
ccccttatgt ccagggcttc acgcatgcta caatggccgg tacaaagggc tgcgatcncc   1200
gtgaggggga gcgaatccca aaaagccggt ctcagttcgg attggggtct gcaactcgac   1260
cccatgaagt cggagtcgct agtaatcgca gatcagcaac gctgcggtga atacgttccc   1320
gggccttgta cacaccgccc gtcacgtcac gaaagtcggc aacacccgaa gccggtggcc   1380 taaccccttgt gggggggagcc gtcgaaggtg gggctggcga ttgggacgaa gtcgtaacaa  1440
ggtagccg                                                            1448
```

<210> SEQ ID NO 5
<211> LENGTH: 15
<212> TYPE: PRT
<213> ORGANISM: Nocardioides sp.
<220> FEATURE:
<223> OTHER INFORMATION: strain SG-4G

<400> SEQUENCE: 5

Ala Asn Phe Val Leu Val His Gly Ala Trp His Gly Gly Trp Cys

<210> SEQ ID NO 6
<211> LENGTH: 11
<212> TYPE: PRT
<213> ORGANISM: Nocardioides sp.
<220> FEATURE:
<223> OTHER INFORMATION: strain SG-4G

<400> SEQUENCE: 6

Leu Val Tyr Leu Asp Ala Phe Val Pro Glu His
1               5                   10

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 7
atggccaact tcgtcctcgt gc                                    22

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 8
gacgaaggcg tcgaggtaga cc                                    22

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 9
atcctcgtcg gccattcgta c                                     21

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 10
aagatcaggt cgctggtcta cctc                                  24

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 11
gttcacccag tcgcgcttgt c                                     21

<210> SEQ ID NO 12
<211> LENGTH: 49
<212> TYPE: DNA
<213> ORGANISM: Artificial Sequence

```
<220> FEATURE:
<223> OTHER INFORMATION: Oligonucleotide primer

<400> SEQUENCE: 12
ggggacaagt ttgtacaaaa aagcaggctt aatggcgaac tttgtgctg                49

<210> SEQ ID NO 13
<211> LENGTH: 48
<212> TYPE: DNA
<213> ORGANISM: Artificial Sequence
<220> FEATURE:
<223> OTHER INFORMATION: Oligonucleotide primer

<400> SEQUENCE: 13
ggggaccact ttgtacaaga aagctgggta ttatcagccc agcgcggc                 48

<210> SEQ ID NO 14
<211> LENGTH: 235
<212> TYPE: PRT
<213> ORGANISM: Alpha proteobacterium
<220> FEATURE:
<223> OTHER INFORMATION: BAL199

<400> SEQUENCE: 14
```

Met Thr Thr Tyr Val Leu Val His Gly Ala Trp His Gly Gly Trp Cys
1               5                   10                  15

Trp Val Arg Val Ala Asp Arg Leu Arg Ala Ala Gly His Thr Val Phe
                20                  25                  30

Thr Pro Thr Leu Thr Gly Leu Ala Glu Arg Ala His Thr Leu Thr Pro
            35                  40                  45

Thr Ile Ser Leu Gln Thr His Ile Lys Asp Ile Ala Arg Leu Leu Gln
        50                  55                  60

Trp Glu Glu Leu Arg Asp Val Val Leu Val Gly His Ser Tyr Gly Gly
65                  70                  75                  80

Met Val Ile Thr Gly Thr Ala Asp Arg Val Ala Asp Arg Val Arg Asn
                85                  90                  95

Leu Ala Phe Val Asp Ala Leu Leu Pro Lys His Gly Gln Ser Ala Phe
            100                 105                 110

Asp Leu Arg Thr Ala Glu Ala Asn Ala Gln Ile Arg Glu Arg Ala Arg
        115                 120                 125

Ala Leu Gly Gly Gly Trp Arg Ile Pro Pro Thr Ser Ala Glu Ala Phe
    130                 135                 140

Met Val Asn Pro Ala Asp Arg Thr Trp Val Asp Ala Lys Cys Thr Asp
145                 150                 155                 160

Leu Pro Ile Gly Cys Phe Ser Glu Lys Leu His Leu Ser Gly Ala Gly
                165                 170                 175

Asp Arg Ile Ala Asp Arg Val Tyr Ile Arg Ala Gly Gly Tyr Pro Asn
            180                 185                 190

Pro Ala Phe Asp Ala Ala Leu Glu Met Ala Arg Ala Asp Ser Arg Phe
        195                 200                 205

Arg Cys His Val Val Asp Cys Gly His Asp Ile Met Val Asp Ala Pro
    210                 215                 220

Asp Glu Leu Thr Arg Ile Leu Leu Glu Ser Ala
225                 230                 235

```
<210> SEQ ID NO 15
<211> LENGTH: 273
<212> TYPE: PRT
<213> ORGANISM: Xanthobacter autotrophicus
<220> FEATURE:
```

-continued

<223> OTHER INFORMATION: Py2

<400> SEQUENCE: 15

Met Thr Ile Ala Pro Thr Leu Gly Pro Asp Ile Ile Ala Ala Glu
1               5                   10                  15

Ile Leu Thr Met Ala Asp Phe Leu Val His Gly Ala Trp His Gly
            20                  25                  30

Gly Trp Cys Trp Arg Arg Val Val Ala Ile Leu Ala Gly Glu Gly His
        35                  40                  45

Arg Val Phe Ala Pro Ser Leu Thr Gly Leu Gly Asp Arg Ala His Leu
    50                  55                  60

Leu Ser Pro Asp Val Gly Leu Ala Thr His Val Asp Val Leu Ala
65                  70                  75                  80

Val Ile Glu Ala Glu Leu Ala Asp Ile Val Leu Cys Ala His Ser
                85                  90                  95

Tyr Gly Gly Ala Val Ala Thr Gln Val Ala Asp Arg Met Pro Gly Lys
            100                 105                 110

Ile Gly Ala Leu Val Phe Leu Asp Ala Leu Leu Pro Gln Asp Gly Arg
        115                 120                 125

Ser Leu Leu Asp Leu Asp Ser Pro Lys Arg Arg Glu Ala Ile Val Ser
    130                 135                 140

Arg Val Val Glu Thr Pro Arg Gly Pro Val Leu Pro Pro Ala Pro Ala
145                 150                 155                 160

Ala Leu Tyr Ala Leu Ala Ala Pro Glu Asp Val Ala Trp Val Asp Arg
                165                 170                 175

Arg Cys Val Pro Gln Ala Leu Arg Thr Tyr Thr Asp Pro Ala Val Leu
            180                 185                 190

Thr Gly Ala Trp Met Glu Ile Lys Val Leu Ala Tyr Ala Cys Thr Leu
        195                 200                 205

Arg Phe Pro Ala Pro Asp Phe Arg Asp Ile Ala Ala Gln Leu Ala Lys
    210                 215                 220

Asp Pro Arg Phe Thr Ile Arg Glu Leu Thr Ser Gly His Asp Ala Met
225                 230                 235                 240

Ile Asp Val Pro Gln Asp Val Ala Asp Leu Leu Ala Cys Ala Glu
                245                 250                 255

Ala Ala Arg Thr Val Glu Ala Cys Ala Pro Thr Gly Ser Pro
            260                 265                 270
Ser

<210> SEQ ID NO 16
<211> LENGTH: 246
<212> TYPE: PRT
<213> ORGANISM: Methylobacterium nodulans
<220> FEATURE:
<223> OTHER INFORMATION: ORS 2060

<400> SEQUENCE: 16

Met Thr Gly Arg Glu Arg Ser Leu Thr Phe Val Leu Val His Gly Ala
1               5                   10                  15

Trp His Gly Gly Trp Cys Trp Arg Arg Val Ala Asp Arg Leu Ala Ala
            20                  25                  30

Gln Gly His Arg Val Phe Ala Pro Thr Cys Thr Gly Leu Gly Glu Arg
        35                  40                  45

Ala His Leu Leu Ser Arg Ala Ile Thr Leu Asp Thr Phe Val Gln Asp
    50                  55                  60

Ile Ala Gly Val Ile Ala Ala Glu Glu Leu Ala Glu Ile Ile Leu Val

```
                    65                  70                  75                  80
Gly His Ser Phe Gly Gly Leu Ala Val Ser Gly Val Ala Asp Ala Met
                        85                  90                  95
Pro Glu Arg Ile Arg His Leu Val Tyr Leu Asp Ser Leu Leu Val Glu
                100                 105                 110
Pro Gly Arg Ala Pro Phe Asp Ala Leu Pro Pro Glu Val Ala Ala Ala
                115                 120                 125
Arg Arg Gln Ala Ala Ala Glu Thr Ser Gly Gly Val Ser Leu Pro Val
            130                 135                 140
Pro Pro Pro Glu Ser Phe Gly Val Ile Asp Ala Ala Asp Ala Ala Trp
145                 150                 155                 160
Leu Gly Arg Arg Leu Thr Pro His Pro Leu Gly Thr Tyr Glu Ser Pro
                165                 170                 175
Leu Arg Leu Lys Gly Pro Leu Gly Asn Gly Leu Pro Arg Thr Tyr Val
            180                 185                 190
Asp Cys Thr Asn Pro Ser Tyr Pro Pro Leu Asp Gly Val Lys Asp Trp
                195                 200                 205
Val Arg Arg Gln Pro Gly Trp Asp Trp Ala Ala Leu Ala Thr Gly His
        210                 215                 220
Asp Ala Met Val Ser Thr Pro Asp Ala Leu Ala Arg Leu Leu Val Glu
225                 230                 235                 240
Leu Ala Thr Pro Arg Pro
                245

<210> SEQ ID NO 17
<211> LENGTH: 243
<212> TYPE: PRT
<213> ORGANISM: Methylobacterium sp.
<220> FEATURE:
<223> OTHER INFORMATION: 4-46

<400> SEQUENCE: 17

Met Ala Glu Arg Glu Arg Pro Ala Phe Val Leu Val His Gly Ala Trp
1               5                   10                  15
His Gly Gly Trp Cys Trp Arg Arg Val Ala Asp Leu Leu Arg Gly Arg
                20                  25                  30
Gly His Arg Val Phe Ala Pro Thr Cys Thr Gly Leu Gly Glu Arg Ala
            35                  40                  45
His Leu Leu Ser Arg Ala Val Thr Leu Asp Thr Phe Val Arg Asp Val
        50                  55                  60
Ala Gly Leu Ile Val Ala Glu Glu Leu Asp Val Val Leu Val Val Gly
65                  70                  75                  80
His Ser Phe Gly Gly Leu Pro Val Ser Gly Val Ala Asp Ala Met Pro
                85                  90                  95
Glu Arg Ile Arg His Leu Val Leu Leu Asp Ala Met Leu Val Glu Pro
                100                 105                 110
Gly Arg Ala Pro Phe Asp Ala Val Pro Pro Asp Leu Ala Ala Ala Arg
            115                 120                 125
Arg Arg Ala Ala Ala Glu Thr Ser Gly Gly Val Ser Leu Pro Val Pro
        130                 135                 140
Pro Pro Glu Ala Phe Gly Val Phe Asp Pro Ala Asp Ala Ala Trp Leu
145                 150                 155                 160
Ala Arg Arg Leu Thr Pro His Pro Leu Gly Thr Tyr Glu Ser Pro Leu
                165                 170                 175
Val Leu Arg Asn Pro Val Gly Asn Gly Leu Pro Arg Thr Tyr Val Asp
            180                 185                 190
```

```
Cys Thr Ala Pro Thr Tyr Pro Ala Leu Asp Gly Val Lys Glu Trp Val
            195                 200                 205

Arg Arg Gln Pro Gly Trp Arg Phe Ala Asp Leu Ala Thr Gly His Asp
        210                 215                 220

Ala Met Val Ser Ala Pro Glu Ala Thr Ala Arg Leu Leu Leu Asp Cys
225                 230                 235                 240

Ala Gly Ala

<210> SEQ ID NO 18
<211> LENGTH: 237
<212> TYPE: PRT
<213> ORGANISM: Sphingomonas wittichii
<220> FEATURE:
<223> OTHER INFORMATION: RW1

<400> SEQUENCE: 18

Met Ser Arg Ser Phe Val Leu Val His Gly Ala Trp Arg Gly Gly Trp
1               5                   10                  15

Cys Tyr Thr Arg Thr Ala Ala Leu Leu Arg Ala Ala Gly His Arg Val
            20                  25                  30

Phe Thr Pro Thr Leu Thr Gly Leu Gly Glu Arg Ser His Leu Ala Thr
        35                  40                  45

Gly Ser Val Gly Phe Arg Thr His Val Asp Asp Val Ala Asn Val Leu
    50                  55                  60

Arg Trp Glu Gly Leu Asp Asp Val Val Leu Cys Gly His Ser Tyr Gly
65                  70                  75                  80

Gly Met Val Ala Ala Val Ala Asp Ala Met Pro Asp Arg Ile Ala
                85                  90                  95

Ala Leu Leu Phe Leu Asp Ala Ile Leu Pro Glu Ala Gly Lys Ser Leu
            100                 105                 110

Leu Asp Ile Cys Ala Ala Glu Glu Val Ala Thr Gly Leu Leu Arg Ser
        115                 120                 125

Ala Ala Ala Ser Gly Gly Arg Leu Val Pro Pro Leu Pro Ala Ala Leu
    130                 135                 140

Phe Gly Leu Asn Glu Ala Asp Val Ala Met Val Glu Ala Leu Cys Thr
145                 150                 155                 160

Pro His Pro Leu Pro Cys Phe Cys Glu Pro Val Glu Leu Thr Gly Ala
                165                 170                 175

Trp Glu Gly Ile Ala Arg Lys Thr Tyr Val Arg Ala Thr Gly Trp Ala
            180                 185                 190

Gly Tyr Ala Ala Leu Gly Phe Asp Pro Met Ala Lys Val Glu Ala Gly
        195                 200                 205

Ala Gly Trp Ser Thr Ile Asp Val Asp Cys Gly His Glu Val Ala Leu
    210                 215                 220

Asp Ala Pro Ala Arg Leu Ala Asp Met Leu Leu Asn Ala
225                 230                 235

<210> SEQ ID NO 19
<211> LENGTH: 243
<212> TYPE: PRT
<213> ORGANISM: Polaromonas naphthalenivorans
<220> FEATURE:
<223> OTHER INFORMATION: CJ2

<400> SEQUENCE: 19

Met Ala Asn Phe Val Leu Val His Gly Ala Trp His Gly Gly Trp Cys
1               5                   10                  15
```

```
Trp Gln Arg Val Thr Ala Val Leu Gln Arg Gly Gly His Arg Val His
                 20                  25                  30

Ala Val Thr Leu Thr Gly Leu Gly Glu Arg Ala His Leu Leu Ser Pro
             35                  40                  45

Ala Ile Thr Leu Asp Thr His Ile Asp Asp Val Ile Asn Leu Ile Glu
         50                  55                  60

Ala Glu Glu Leu Leu Asp Val Val Leu Ala Val His Ser Tyr Ala Gly
 65                  70                  75                  80

Met Ile Gly Thr Ala Val Ala Asp Arg Leu Gly Gln Arg Leu Lys His
                 85                  90                  95

Leu Val Tyr Val Asp Ala Val Val Pro Lys Pro Gly Glu Ser Trp Ser
            100                 105                 110

Ser Thr Gln Ser Ser Ala Thr Gln Gln Gln Arg Leu Ala Ala Ala Gln
            115                 120                 125

Ala Ser Ala His Phe Ser Phe Pro Pro Asp Pro Glu Val Tyr Gly
        130                 135                 140

Leu Lys Asp Asp Asp Arg Glu Trp Val Lys Arg Arg Gln Thr Pro His
145                 150                 155                 160

Pro Gly Asn Thr Tyr Gln Ala Pro Leu Asp Phe Asp Val Gln Arg Val
                165                 170                 175

Ala Ala Val Pro Arg Thr Phe Val Ser Cys Thr Glu Pro Ala Leu Ala
            180                 185                 190

Thr Ile Ala Pro Ser Arg Leu Arg Ala Lys Asp Pro Lys Phe Trp Asp
        195                 200                 205

Gly Ala Trp Leu Pro Gly Ala Ser Thr Ile Glu Leu Gln Thr Gly His
                210                 215                 220

Asp Pro Met Val Ser Glu Pro Ala Ala Leu Val Arg Ile Leu Leu Gly
225                 230                 235                 240

Cys Gly Ala

<210> SEQ ID NO 20
<211> LENGTH: 268
<212> TYPE: PRT
<213> ORGANISM: Bordetella avium
<220> FEATURE:
<223> OTHER INFORMATION: 197N

<400> SEQUENCE: 20

Met Gln Arg Arg Thr Leu Leu Lys Met Ala Ala Gly Leu Pro Leu Ile
 1               5                  10                  15

Thr Gly Gly Thr Ala Leu Ala Glu Ala Ala Pro Lys Lys Ser Asn Thr
                 20                  25                  30

Tyr Val Leu Ala Ser Gly Ser Trp His Gly Gly Trp Cys Trp Arg Pro
             35                  40                  45

Val Ala Asp Arg Leu Arg Ala Ala Gly His Arg Val Tyr Thr Pro Ser
         50                  55                  60

Tyr Thr Gly Met Gly Asp Arg Ala His Leu Leu Ala Gln Gly Ile Thr
 65                  70                  75                  80

Ile Asp Thr Phe Val Glu Asp Leu Val Gln Leu Ile Gln Ser Glu Glu
                 85                  90                  95

Leu Asn Asp Val Ile Leu Val Gly His Ser Phe Gly Gly Ile Pro Ile
            100                 105                 110

Thr Gly Val Ala Asp Arg Ile Pro Glu Ala Leu Ala His Leu Val Tyr
            115                 120                 125

Phe Asp Ser Ile Val Leu Lys Asn Gly Gln Asn Ala Phe Ser Val Tyr
        130                 135                 140
```

Pro Lys Ala Asp Ala Asp Ala Arg Ile Ala Ala Thr Lys Ala Thr
145                 150                 155                 160

Gln Gly Leu Ala Val Pro Ile Pro Asp Pro Leu Pro Ala Ala Trp Gly
                165                 170                 175

Ile Ala Pro Gly Ser Asp Thr Glu Ala Trp Val Lys Arg Leu Thr
            180                 185                 190

Gln His Pro Leu Ala Ser Tyr Thr Thr Pro Leu Thr Leu Gln His Pro
        195                 200                 205

Ile Gly Asn Gly Arg Pro Arg Thr Tyr Ile His Cys Thr Gln Pro Glu
    210                 215                 220

Leu Pro Val Leu Glu Gln Ser Arg Lys Leu Val Lys Ser Gln Gln Gly
225                 230                 235                 240

Trp Asn Trp Val Asp Leu Ala Ala Pro His Glu Ala His Ile Thr His
                245                 250                 255

Pro Ala Leu Leu Thr Glu Val Leu Leu Gly Leu Ser
            260                 265

<210> SEQ ID NO 21
<211> LENGTH: 244
<212> TYPE: PRT
<213> ORGANISM: Polaromonas sp.
<220> FEATURE:
<223> OTHER INFORMATION: JS666

<400> SEQUENCE: 21

Met Ser His Asn Phe Val Phe Val His Gly Ala Trp His Gly Gly Trp
1               5                   10                  15

Cys Trp Arg Arg Val Thr Gln Ala Leu Gln Leu Asp His His Lys Val
                20                  25                  30

Tyr Pro Val Thr Leu Thr Gly Leu Gly Glu Arg Ala His Leu Leu Ser
            35                  40                  45

Pro Ser Ile Asn Leu Asp Thr His Ile Asp Asp Val Ile Ser Ala Ile
    50                  55                  60

Glu Val Glu Glu Leu Ser Glu Val Ile Leu Ala Val His Ser Tyr Ala
65                  70                  75                  80

Gly Met Ile Gly Thr Ala Val Ala Asp Arg Val Pro Lys Arg Ile Lys
                85                  90                  95

His Leu Val Tyr Val Asp Ala Val Leu Pro Lys Pro Gly Glu Ser Trp
            100                 105                 110

Ser Ser Thr Gln Ser Ala Ala Thr Gln Gln Gln Arg Leu Thr Ala Ala
        115                 120                 125

Gln Ala Ser Thr Arg Phe Ser Phe Pro Pro Asp Pro Glu Val Phe
130                 135                 140

Gly Leu His Asp Ala Asp Arg Glu Trp Val Lys Arg Arg Gln Thr Pro
145                 150                 155                 160

His Pro Gly Asn Thr Tyr Gln Ala Pro Leu Asn Phe Asp Met Gln Arg
                165                 170                 175

Val Ala Ala Val Pro Arg Thr Tyr Val Ser Cys Thr Gln Pro Ala Leu
            180                 185                 190

Ala Thr Ile Asp Pro Ser Arg Leu Arg Ala Arg Asp Pro Lys Phe Trp
        195                 200                 205

Asp Gly Ala Trp Leu Pro Asn Ser Lys Phe Val Glu Ile Gln Thr Gly
    210                 215                 220

His Asp Pro Met Ile Ser Asp Pro His Ala Leu Thr Lys Ile Leu Leu
225                 230                 235                 240

-continued

Asp Cys Ala Ala

<210> SEQ ID NO 22
<211> LENGTH: 241
<212> TYPE: PRT
<213> ORGANISM: Streptomyces coelicolor
<220> FEATURE:
<223> OTHER INFORMATION: A3(2)

<400> SEQUENCE: 22

Met Ser Thr Phe Leu Leu Ile His Gly Ala Trp His Ser Gly Arg Cys
1               5                   10                  15

Trp Glu Arg Val Val Pro Leu Leu Glu Ala Ala Gly His Arg Val Phe
            20                  25                  30

Ala Pro Ser Leu Thr Gly Tyr Gly Asp Lys Ala His Leu Leu Gly Pro
        35                  40                  45

Glu Val Gly Leu Asp Thr His Val Asp Val Val Gly Leu Ile Ala
    50                  55                  60

Gly Glu Asn Leu Ser Asp Val Val Leu Val Gly His Ser Tyr Ala Gly
65                  70                  75                  80

Leu Val Ile Ser Ser Ala Ala His Arg Ile Pro Glu Arg Ile Ala His
                85                  90                  95

Leu Val Tyr Leu Asp Ala Met Val Pro Glu Asp Gly Glu Ser Ala Val
            100                 105                 110

Asp Val His Pro Val Thr Gln Arg Leu Ile Glu Leu Ala Glu Lys Ser
        115                 120                 125

Glu Ser Gly Trp Arg Val Pro Pro Met Pro Glu Gln Pro Ala Pro Leu
    130                 135                 140

Gly Leu Phe Gly Val Thr Asp Pro Ala Asp Val Ala Trp Leu His Gly
145                 150                 155                 160

Met Leu Ser Asp Gln Pro Val Arg Cys Leu Arg Gln Pro Val Arg Leu
                165                 170                 175

Gly Asn Pro Ala Ala Asp Ala Ile Pro Arg Thr His Ile His Asn Val
            180                 185                 190

Gly Ala Met Pro Thr Gly Ile Thr Arg Arg Pro Val Pro Pro Ile Gln
        195                 200                 205

Pro Asn Gly Thr Ala Ala Gln Val Trp Glu Leu Pro Thr Gly His Asp
    210                 215                 220

Cys Met Ile Thr Met Pro Thr Glu Leu Ser Glu Leu Leu Lys Leu
225                 230                 235                 240

Pro

<210> SEQ ID NO 23
<211> LENGTH: 274
<212> TYPE: PRT
<213> ORGANISM: Burkholderia ambifaria
<220> FEATURE:
<223> OTHER INFORMATION: IOP40-10

<400> SEQUENCE: 23

Met Asn Arg Arg Asn Phe Asn Asn Gly Ala Leu Gly Leu Thr Leu Gly
1               5                   10                  15

Ala Phe Ala Ala Arg Gln Val Asn Ala Gln Asp Thr Pro Ala Lys Ala
            20                  25                  30

Pro Ala Pro Ser Pro Ser Lys Ala Arg Thr Phe Val Leu Val His Gly
        35                  40                  45

Ala Trp Tyr Gly Gly Trp Cys Trp Lys Lys Val Ala Glu Lys Leu Arg
    50                  55                  60

```
Ala Ala Gly His Tyr Val Ser Thr Pro Thr Cys Pro Gly Val Gly Glu
 65                  70                  75                  80

Ala Lys His Leu Leu Ser Lys Asp Ile Thr Leu Thr His Ile Thr
             85                  90                  95

Ser Ile Val Asn His Ile Gln Tyr Glu Gly Leu Ser Asp Val Ile Leu
            100                 105                 110

Val Gly Ser Gly Phe Ser Gly Leu Ile Ile Ser Gly Val Ala Asp Arg
        115                 120                 125

Ile Pro Gln Lys Leu Arg Thr Leu Val Tyr Leu Asp Ala Leu Val Val
130                 135                 140

Pro Asn Gly Val Ser Ala Phe Asp Ala Gln Pro Ala Glu Ile Thr Arg
145                 150                 155                 160

Lys Arg Leu Asp Gln Val Ala Arg Glu Gly Asn Gly Ile Ala Ile Pro
                165                 170                 175

Pro Pro Pro Leu Ser Thr Tyr Asp Ile Val Met Glu Lys Asp Lys Ala
            180                 185                 190

Trp Val Gly Ser Leu Leu Thr Pro His Pro Val Gly Pro Tyr Gln Glu
        195                 200                 205

Lys Phe Tyr Leu Lys Asn Pro Ile Gly Asn Gly Val Pro Arg Ile Tyr
210                 215                 220

Val Asp Cys Val Ala His Ser Phe Ala Pro Leu Ala Lys Leu Lys Lys
225                 230                 235                 240

Asp Ile Arg Ala Gln Pro Gly Trp Ile Trp Arg Glu Leu Asp Ala Arg
                245                 250                 255

His Asp Pro Met Val Thr Glu Pro His Leu Leu Asp Glu Phe Leu Gln
            260                 265                 270

Ser Ile

<210> SEQ ID NO 24
<211> LENGTH: 241
<212> TYPE: PRT
<213> ORGANISM: Bradyrhizobium japonicum
<220> FEATURE:
<223> OTHER INFORMATION: USDA 110

<400> SEQUENCE: 24

Met Glu Thr Pro Met Ala Ala Arg Ala Lys Thr Phe Leu Leu Cys His
  1               5                  10                  15

Gly Ala Trp Ser Gly Gly Trp Ala Trp Lys Lys Met His Pro Leu Met
             20                  25                  30

Ala Gln Ala Gly His Arg Leu Val Ala Pro Thr Tyr Thr Gly Leu Gly
         35                  40                  45

Glu Arg Ser His Leu Ala Asn Pro Ser Ile Asp Leu Glu Thr His Ile
     50                  55                  60

Gln Asp Ile Leu Asn Val Ile Lys Phe Glu Asp Leu Ser Asp Leu Val
 65                  70                  75                  80

Leu Leu Gly His Ser Tyr Gly Gly Met Val Ala Thr Gly Val Ala Asp
             85                  90                  95

Arg Ala Arg Glu Arg Val Thr Gln Leu Ile Tyr Leu Asp Ala Phe Val
            100                 105                 110

Pro Arg Asp Gly Gln Ser Leu Phe Asp Leu Asn Glu Ser Gly Arg Glu
        115                 120                 125

Pro Met Arg Lys Ala Ala Ala Gly Asp Gly Tyr Arg Ile Pro Pro
130                 135                 140

Asn Pro Pro Pro Pro Asp Thr Pro Gln Ala Asp Leu Asp Trp Leu Asn
```

```
                145                 150                 155                 160
Ala Arg Arg Ile Asn Met Pro Ile Lys Cys Phe Glu Thr Lys Leu Lys
                    165                 170                 175

Leu Glu His Gly Asp Pro Pro Met Pro Arg Ser Tyr Ile Tyr Cys Thr
                180                 185                 190

Arg Ile Pro Pro Gly Asp Val Phe Gly Gln Phe Ala Lys His Thr Lys
            195                 200                 205

Asn Glu Asp Gly Trp Arg Tyr Phe Glu Leu Asp Ala Ser His Ala Pro
        210                 215                 220

Asn Val Thr Ala Pro Ala Ala Leu Met Ala Val Leu Asn Glu Ile Ala
225                 230                 235                 240

Ala

<210> SEQ ID NO 25
<211> LENGTH: 223
<212> TYPE: PRT
<213> ORGANISM: Mycobacterium sp.
<220> FEATURE:
<223> OTHER INFORMATION: JLS

<400> SEQUENCE: 25

Met Ala Thr Phe Val Leu Ile Pro Gly Ala Cys His Gly Ala Trp Cys
1               5                   10                  15

Phe Asp Asp Leu Val Gly Ala Leu Arg Asn Arg Gly His Arg Ala Asp
                20                  25                  30

Ala His Thr Leu Thr Gly Val Ala Glu Arg Ala His Leu Ala His Ala
            35                  40                  45

Gly Val Asn Leu Asp Thr His Ile Thr Asp Met Cys Glu Ala Val Ala
        50                  55                  60

Ala Met Pro Asp Asp Leu Val Leu Val Gly His Ser Tyr Gly Gly
65                  70                  75                  80

Met Val Ile Thr Ala Val Ala Asp Arg Met Pro Asp Arg Val Asp Ala
                85                  90                  95

Leu Val Tyr Leu Asp Ala Leu Val Pro Arg Asp Gly Glu Ser Cys Trp
            100                 105                 110

Asp Leu Val Asn Asp Ala Glu Arg Gln Trp Tyr Leu Gly Val Asp Asp
        115                 120                 125

Thr Gly Tyr Gly Val Pro Pro Leu Pro Phe Phe Asp Asp Arg Ala Ser
    130                 135                 140

Ser His Pro Leu Ala Ser Leu Leu Gln Pro Ile Arg Leu Ala Gly Gly
145                 150                 155                 160

Ala Asp Gly Val Arg Arg Arg Asp Tyr Ala Tyr Ala Leu Asn Trp Pro
                165                 170                 175

Gly Gln Ser Pro Met Arg Arg Ser Tyr Glu Arg Val Arg Asp Asp Pro
            180                 185                 190

Ala Trp Thr Val His Glu Leu Asp Gly Lys His Asn Leu Met Arg Asp
        195                 200                 205

Asn Pro Asp Asp Leu Leu Arg Ile Leu Leu Ala Ala Ala Ala His
    210                 215                 220

<210> SEQ ID NO 26
<211> LENGTH: 223
<212> TYPE: PRT
<213> ORGANISM: Mycobacterium sp.
<220> FEATURE:
<223> OTHER INFORMATION: MCS

<400> SEQUENCE: 26
```

```
Met Ala Thr Phe Val Leu Ile Pro Gly Ala Cys His Gly Ala Trp Cys
1               5                   10                  15

Phe Asp Ala Leu Val Gly Ala Leu Arg Asn Arg Gly His Arg Ala Asp
            20                  25                  30

Ala His Thr Leu Thr Gly Val Ala Glu Arg Ala His Leu Ala His Ala
        35                  40                  45

Gly Val Asn Leu Asp Thr His Ile Thr Asp Met Cys Glu Ala Val Ala
50                  55                  60

Ala Met Thr Asp Asp Asp Leu Val Leu Val Gly His Ser Tyr Gly Gly
65                  70                  75                  80

Met Val Ile Thr Ala Val Ala Asp Arg Ile Pro Asp Arg Val Asp Ala
                85                  90                  95

Leu Val Tyr Leu Asp Ala Leu Val Pro Arg Asp Gly Glu Ser Cys Trp
            100                 105                 110

Asp Leu Val Asn Asp Ala Glu Arg Gln Trp Tyr Leu Gly Val Asp Asp
            115                 120                 125

Thr Gly Tyr Gly Val Pro Pro Leu Pro Phe Phe Asp Asp Arg Ala Ser
    130                 135                 140

Ser His Pro Leu Ala Ser Leu Leu Gln Pro Ile Arg Leu Ala Gly Gly
145                 150                 155                 160

Ala Ala Gly Val Arg Arg Arg Asp Tyr Ala Tyr Ala Leu Asp Trp Pro
                165                 170                 175

Gly Glu Ser Pro Leu Arg Arg Ser Tyr Glu Arg Val Arg Asp Asp Pro
            180                 185                 190

Ala Trp Thr Val His Glu Leu Asp Gly Lys His Asn Leu Met Arg Asp
        195                 200                 205

Asn Ala Asp Asp Leu Leu Arg Ile Leu Leu Ala Ala Ala His
    210                 215                 220

<210> SEQ ID NO 27
<211> LENGTH: 231
<212> TYPE: PRT
<213> ORGANISM: Bacillus cereus
<220> FEATURE:
<223> OTHER INFORMATION: ATCC 10

```
Lys Lys Ser Ala Met Ser Leu Leu Ala Phe Thr Gln Ser Val Glu Ile
145                 150                 155                 160

Lys Asn Ser Lys Ala Gln Leu Ile Pro His Ile Tyr Val Glu Val Lys
                165                 170                 175

Asp Asn Pro Glu His Trp Pro Met Thr Pro Ile Phe Leu Glu Ser Ala
            180                 185                 190

Lys Lys Ala Arg Asp Arg Lys Trp Glu Val Phe Ser Ile Glu Val Gly
        195                 200                 205

Gly His Trp Val Met Glu Thr Asn Pro Glu Ala Leu Val Arg Ile Leu
    210                 215                 220

Asn Gln Cys Val Glu Val Val
225                 230

<210> SEQ ID NO 28
<211> LENGTH: 234
<212> TYPE: PRT
<213> ORGANISM: Nocardia farcinica
<220> FEATURE:
<223> OTHER INFORMATION: IFM 10152

<400> SEQUENCE: 28

Met Ser Thr Phe Val Leu Val His Gly Ser Trp Ala Gly Gly Trp His
1               5                   10                  15

Trp Ala Asp Ile Arg Ala Arg Leu Glu Gln Ala Gly His Arg Val His
                20                  25                  30

Ala Pro Ser Leu Thr Gly Met Ala Asp Arg His His Leu Ala Gly Glu
            35                  40                  45

His Val Gly Leu His Thr His Ile Asp Asp Val Ala Arg Leu Leu Glu
        50                  55                  60

Trp Glu Arg Leu Thr Asp Val Ile Leu Val Gly His Ser Tyr Gly Gly
65                  70                  75                  80

Met Val Ile Thr Gly Ala Ala Ala Arg Val Pro Glu Arg Ile Ala His
                85                  90                  95

Val Val Tyr Leu Asp Ala Phe Leu Pro Arg Ala Gly Glu Ala Ala Trp
            100                 105                 110

Asp Leu Leu Pro Trp Gln Arg Glu Ala Phe Gln Gln Leu Arg Leu Pro
        115                 120                 125

Asp Arg Pro Trp Leu Val Arg Pro Val Asp Ala Ala Phe Phe Pro
130                 135                 140

Glu Leu Gly Glu Asp Phe Asp Asp Asn Arg Pro Thr Pro Met Pro Ile
145                 150                 155                 160

Ala Thr His Glu Gln Pro Val Pro Asp Ala Pro Ala Pro Gly Ala Leu
                165                 170                 175

Pro Gly Thr Tyr Ile His Cys Thr Ala Ala Pro Ala Tyr Phe Asp Asp
            180                 185                 190

Val Ala Arg Arg Ala Ala Asp Asp Gly Leu Ala Val Val Thr Leu Asp
        195                 200                 205

Ala Gly His Met Ala Leu Leu Thr His Ala Asp Glu Val Ser Ala Thr
    210                 215                 220

Leu Leu Glu Leu Ala Gln Glu Ala Pro Arg
225                 230

<210> SEQ ID NO 29
<211> LENGTH: 222
<212> TYPE: PRT
<213> ORGANISM: Novosphingobium aromaticivorans
<220> FEATURE:
<223> OTHER INFORMATION: DSM 12444
```

<400> SEQUENCE: 29

```
Met Thr Asp Phe Val Leu Val His Gly Ala Trp Gly Gly Ser Phe Ala
1               5                   10                  15

Trp Asp Arg Leu Lys Ala Asp Leu Val Ala Ala Gly His Arg Val Leu
            20                  25                  30

Ala Ala Asp Leu Thr Gly Leu Gly Lys Arg Lys Ala Gly Phe His Pro
        35                  40                  45

Gly Ile Thr Leu Thr Thr His Thr Asp Asp Val Cys Ala Gln Ile Ala
    50                  55                  60

Asp Ala Gly Phe Asp Arg Phe Val Leu Val Gly His Ser Trp Gly Gly
65                  70                  75                  80

Met Val Ile Thr Gly Val Ala Thr Arg Leu Gly Gly Arg Ile Asp Ala
                85                  90                  95

Ile Val Tyr Val Asp Ala Phe Leu Pro Gln Asp Gly Gln Ser Leu Trp
            100                 105                 110

Asp Leu Thr Gly Gln Trp Glu His Asp His Tyr Ile Ser Ser Gln Lys
        115                 120                 125

His Ser Pro Gly Ala Val Ala Pro Leu Pro Gly Leu Glu Ser Pro Val
    130                 135                 140

Leu Ser Ala His Pro Leu Leu Thr Leu Val Glu Ala Val Arg Phe Thr
145                 150                 155                 160

Gly Glu Glu Ala Lys Ile Pro Arg Arg Ile Tyr Val Tyr Ala Asn Gly
                165                 170                 175

Trp Gln Pro Thr Pro Phe Ala Lys Phe Ala Asp Ala Val Gln Asp Asp
            180                 185                 190

Pro Ala Trp Glu Tyr His Glu Ala Glu Ala Ser His Asn Val Met Ala
        195                 200                 205

Asp Gln Pro Glu Gln Leu Leu Arg Ile Val Leu Gly Cys Ala
    210                 215                 220
```

<210> SEQ ID NO 30
<211> LENGTH: 225
<212> TYPE: PRT
<213> ORGANISM: Mycobacterium vanbaalenii
<220> FEATURE:
<223> OTHER INFORMATION: PYR-1

<400> SEQUENCE: 30

```
Met Ser Ser Tyr Val Leu Ile Pro Gly Met Cys His Gly Ala Trp Cys
1               5                   10                  15

Phe Asp Glu Val Ala Ala Ser Leu Arg Ser Ala Gly His His Val Leu
            20                  25                  30

Ala Leu Thr Leu Thr Gly Val Gly Glu Arg Ser His Leu Met Pro Gly
        35                  40                  45

Gly Val Asn Leu Asp Thr His Ile Val Asp Val Leu Ala Ala Ile Asp
    50                  55                  60

Asn Asp Ala Ala Thr Gly Ala Asp Leu Ile Leu Val Gly His Ser Tyr
65                  70                  75                  80

Gly Gly Met Val Ile Thr Gly Val Ala Asp Arg Ile Pro Asp Arg Val
                85                  90                  95

Asp Ser Leu Val Phe Leu Asp Ala Val Val Pro Arg Asp Gly Glu Ala
            100                 105                 110

Cys Trp Asp Leu Val Asn Asp Glu Glu Arg Gln Trp Tyr Val Lys Val
        115                 120                 125

Asp Asp Ser Gly Phe Gly Val Pro Pro Met Pro Phe Phe Asp Asp Arg
```

```
                130                 135                 140
Ala Thr Ser His Pro Leu Ala Thr Val Leu Gln Pro Leu Arg Leu Arg
145                 150                 155                 160

Gly Asp Leu Asn Gly Phe Arg Arg Ile Phe Val Tyr Ala Leu Asp
                165                 170                 175

Trp Pro Gly Glu Ser Pro Leu Arg Pro Ser Tyr Asp Arg Val Arg Asp
                180                 185                 190

Asp Pro Thr Trp Ile Cys His Glu Leu Asp Gly Arg His Asn Leu Met
                195                 200                 205

Arg Asp Arg Pro Ala Asp Leu Leu Arg Ile Leu Leu Ser Ala Ser Gln
210                 215                 220

Ser
225

<210> SEQ ID NO 31
<211> LENGTH: 231
<212> TYPE: PRT
<213> ORGANISM: Bacillus cereus
<220> FEATURE:
<223> OTHER INFORMATION: AH187

<400> SEQUENCE: 31

Met Glu Thr Phe Val Leu Val His Gly Ala Trp Asp Gly Gly Tyr Val
1               5

```
<220> FEATURE:
<223> OTHER INFORMATION: E33L

<400> SEQUENCE: 32

Met Glu Thr Phe Val Leu Val His Gly Ala Trp Asp Gly Gly Tyr Val
1               5                   10                  15

Trp Lys Lys Leu Ala Glu Leu Arg Glu Glu Gly His Ser Val Tyr
            20                  25                  30

Thr Pro Thr Leu Thr Gly Leu Gly Glu Arg Thr His Leu Met Gln Pro
        35                  40                  45

Asn Ile Gly Leu Lys Thr Phe Ile Gln Asp Ile Val Asn Thr Ile Lys
    50                  55                  60

Tyr Gln Gly Leu Lys Asp Val Ile Leu Val Gly His Ser Tyr Ser Gly
65                  70                  75                  80

Met Val Ile Thr Gly Val Ala Glu Val Ile Pro Glu Phe Ile Lys Glu
                85                  90                  95

Leu Val Tyr Val Asp Ala Met Leu Pro Glu Asp Gly Asp Ser Val Met
            100                 105                 110

Asp Ile Ser Gly Pro Glu Met Ala Ala His Phe Ile Glu Glu Val Lys
        115                 120                 125

Val Tyr Gly Glu Gly Trp Arg Val Leu Pro Arg Asn Thr Ile Asp Glu
    130                 135                 140

Arg Lys Ser Ala Met Pro Leu Leu Ala Phe Thr Gln Ser Val Glu Ile
145                 150                 155                 160

Lys Asn Ser Lys Ala Gln Cys Ile Pro His Ile Tyr Val Glu Val Lys
                165                 170                 175

Asp Asn Pro Glu His Trp Pro Met Thr Ser Ile Phe Leu Glu Ser Ala
            180                 185                 190

Lys Lys Ala Arg Asp Arg Lys Trp Glu Ile Phe Ser Ile Glu Val Gly
        195                 200                 205

Gly His Trp Val Met Glu Thr Asn Pro Glu Ala Leu Val Arg Ile Leu
    210                 215                 220

Asn Gln Ser Val Glu Val Ile
225                 230

<210> SEQ ID NO 33
<211> LENGTH: 241
<212> TYPE: PRT
<213> ORGANISM: Leptothrix cholodnii
<220> FEATURE:
<223> OTHER INFORMATION: SP-6

<400> SEQUENCE: 33

Met Thr Pro Pro Pro Ile Val Leu Val His Gly Ala Trp Gly Gly Ala
1               5                   10                  15

Trp Ile Trp Arg Arg Val Leu Gly Pro Leu Arg Ala Ala Gly His Glu
            20                  25                  30

Val His Ala Val Thr Leu Thr Gly Asp Gly Glu Arg Ala His Leu Arg
        35                  40                  45

His Pro Gly Ile Thr Leu Gln Thr His Ile Ala Asp Val Val Gly Leu
    50                  55                  60

Ile Glu Ala Glu Glu Leu Arg Asp Val Met Leu Val Gly His Ser Tyr
65                  70                  75                  80

Gly Gly Gln Val Ile Thr Gly Ala Ala Asp Ala Leu Leu Ala Arg Asp
                85                  90                  95

Ala Gly Ala Ile Arg Gln Leu Val Tyr Val Asp Ala Met Val Pro Leu
            100                 105                 110
```

Pro Gly Glu Gly Trp Gly Gly Ser His Ser Ala Glu Ile Val Ala Ala
            115                 120                 125

Arg Thr Ala Ala Ala Leu Ala Asn His His Ala Leu Pro Pro Pro Asp
        130                 135                 140

Pro Ala Asp Phe Gly Ile Ser Gly Ala Asp Arg Asp Trp Leu Leu Arg
145                 150                 155                 160

Arg Gln Val Pro His Pro Phe Gly Pro Tyr Arg Glu Pro Leu Pro Phe
                165                 170                 175

Asp Gly Glu Arg Trp Ala Arg Leu Arg Arg Ser Phe Ile Asp Cys Asn
            180                 185                 190

Ala Pro Ala Tyr Pro Thr Ile Ser Ala Met Arg Glu Arg Val Arg Gln
        195                 200                 205

Leu Pro Gly Phe Asp Val Arg Glu Ile Ala Thr Gly His Cys Pro Met
    210                 215                 220

Val Ser Glu Pro Ala Ala Leu Val Ala His Leu Leu Ala Ile Ala Ala
225                 230                 235                 240

Thr

<210> SEQ ID NO 34
<211> LENGTH: 229
<212> TYPE: PRT
<213> ORGANISM: Bacillus cereus
<220> FEATURE:
<223> OTHER INFORMATION: subsp. cytotoxis NVH 391-98

<400> SEQUENCE: 34

Met Glu Thr Phe Val Leu Val His Gly Ala Trp Asp Gly Ser Tyr Val
1               5                   10                  15

Trp Gly Lys Val Ala Ala Leu Leu Arg Lys Asp Gly His Arg Val Tyr
            20                  25                  30

Thr Pro Thr Leu Thr Gly Leu Gly Glu Arg Thr His Leu Met Gln Pro
        35                  40                  45

Ser Ile Gly Leu Asn Thr Tyr Ile Gln Asp Ile Val Asn Val Ile Arg
    50                  55                  60

Tyr Glu Glu Leu Lys Asp Val Ile Leu Val Gly His Ser Tyr Ser Gly
65                  70                  75                  80

Met Val Ile Thr Gly Val Ala Glu Val Ile Pro Glu Phe Ile Lys Lys
                85                  90                  95

Met Val Tyr Val Asp Ala Met Ile Pro Asp Asp Gly Asp Ser Val Met
            100                 105                 110

Asp Ile Ser Gly Ser Lys Met Ala Ala His Phe Ile Glu Glu Val Lys
        115                 120                 125

Ala Tyr Gly Glu Gly Trp Arg Val Leu Pro Arg Asn Thr Phe Asp Glu
    130                 135                 140

Arg Lys Ser Ala Met Ser Leu Leu Ala Phe Thr Gln Ala Val Glu Ile
145                 150                 155                 160

Lys Asn Pro Ile Val Gln His Ile Pro His Ile Tyr Val Glu Ile Gln
                165                 170                 175

Asp His Pro Glu Tyr Trp Pro Met Thr Pro Ile Phe Leu Ala Ser Ala
            180                 185                 190

Lys Lys Ala Arg Asp Arg Lys Trp Asn Val Phe Ser Ile Glu Ser Gly
        195                 200                 205

Gly His Trp Ile Met Glu Thr Asn Pro Glu Ala Leu Val His Ile Leu
    210                 215                 220

Asn Lys Cys Val Glu
225

<210> SEQ ID NO 35
<211> LENGTH: 241
<212> TYPE: PRT
<213> ORGANISM: Rhodobacterales bacterium
<220> FEATURE:
<223> OTHER INFORMATION: HTCC2654

<400> SEQUENCE: 35

Met Ala Val Tyr Val Leu Val His Gly Ala Trp His Thr Gly Asp Leu
1               5                   10                  15

Leu Glu Pro Val Ala Ala Pro Ile Arg Ala Ala Gly His Glu Val His
            20                  25                  30

Leu Pro Thr Ile Ala Gly Asn Leu Pro Gly Gly Ser Lys Asp Val Gly
        35                  40                  45

Leu Asp Ala Ala Ile Gly Ser Ile Val Asp Tyr Leu Asp Glu His Asp
    50                  55                  60

Leu Arg Asp Val Val Leu Gly His Ser Tyr Gly Gly Met Val Ile
65                  70                  75                  80

Thr Gly Val Ala Asp Arg Val Pro Glu Arg Leu Arg Arg Leu Val Tyr
                85                  90                  95

Trp Asn Ala Phe Val Pro Asn Asp Gly Glu Cys Leu Asn Asp Met Val
            100                 105                 110

Pro Pro His Tyr Val Ala Leu Phe Asp Gly Val Ser Gln Ala Ser Ala
        115                 120                 125

Asp Asn Thr Val Met Leu Pro Phe Pro Ile Trp Arg Glu Ala Phe Ile
    130                 135                 140

Asn Asp Ala Asp Leu Ala Arg Ala Glu Glu Thr Phe Ala Met Leu Asn
145                 150                 155                 160

Pro His Pro Tyr Ala Thr Phe Thr Asp Ala Ile Ser Leu Ser Lys Asn
                165                 170                 175

Pro Ala Glu Met Glu Ile Gly Lys Ser Tyr Val Leu Cys Val Glu Asp
            180                 185                 190

Thr Ala Leu Pro His Ser Met Pro Trp His Pro Arg Leu Ser Glu Lys
        195                 200                 205

Leu Gly Leu Phe Arg Leu Val Thr Thr Gly Gly Ser His Glu Ala Cys
    210                 215                 220

Phe Thr Asp Pro Glu Gly Leu Ala Asp Ala Ile Leu Arg Ala Gly Arg
225                 230                 235                 240

Asp

<210> SEQ ID NO 36
<211> LENGTH: 247
<212> TYPE: PRT
<213> ORGANISM: Bradyrhizobium sp.
<220> FEATURE:
<223> OTHER INFORMATION: BTAi1

<400> SEQUENCE: 36

Met Gln Arg Asn Leu Ile Met Ser Thr Tyr Val Leu Val His Gly Ala
1               5                   10                  15

Trp His Thr Gly Ala Glu Leu Glu Pro Val Ala Ala His Ile Arg Ser
            20                  25                  30

Ala Gly His Ile Val His Leu Pro Thr Ile Arg Gly Asn Arg Pro Gly
        35                  40                  45

Asp Pro Lys Thr Thr Gly Leu Asp Glu Ala Ile Gln Ser Ile Cys Asp
    50                  55                  60

Tyr Phe Thr Glu Gln Asp Ile Thr Asp Ala Ile Leu Met Gly His Ser
65                  70                  75                  80

Tyr Gly Gly Met Val Ile Thr Gly Val Ala Asp Arg Ile Pro Thr Arg
                85                  90                  95

Ile Arg Arg Leu Ile Tyr Trp Asn Ala Phe Val Pro Asn Asn Gly Glu
            100                 105                 110

Cys Leu Asn Asp Met Val Pro Pro Gln Tyr Val Ala Leu Phe Asp Ala
            115                 120                 125

Val Ala Ala Glu Arg Gly Asp Gly Ser Val Val Leu Pro Phe Pro Ile
130                 135                 140

Trp Arg Glu Ala Phe Ile Asn Asp Ala Asp Leu Ala Thr Ala Thr Arg
145                 150                 155                 160

Ala Tyr Glu Val Leu Asn Pro His Pro Asn Lys Thr Phe Thr Asp Ala
            165                 170                 175

Ile Lys Leu Arg Thr Asn Pro Ala Glu Met Thr Ile Ala Lys Ser Tyr
            180                 185                 190

Ile Asn Cys Thr Glu Asp Thr Ala Leu Pro His Gly Leu Pro Trp His
            195                 200                 205

Pro Arg Leu Ser Ser Lys Leu Gly Leu Phe Arg Leu Val Gln Val Pro
            210                 215                 220

Gly Ser His Glu Leu Cys Phe Ser Glu Pro Ala Arg Leu Ala Gln Ala
225                 230                 235                 240

Ile Met Asp Ala Gly Arg Asp
                245

<210> SEQ ID NO 37
<211> LENGTH: 247
<212> TYPE: PRT
<213> ORGANISM: Bradyrhizobium sp.
<220> FEATURE:
<223> OTHER INFORMATION: ORS278

<400> SEQUENCE: 37

Met Gln Arg Asn Leu Thr Met Ser Thr Tyr Val Leu Ile His Gly Ala
1               5                   10                  15

Trp His Thr Gly Ala Glu Leu Glu Pro Val Ala Ala Pro Ile Arg Ala
                20                  25                  30

Ala Gly His Ile Val His Leu Pro Thr Ile Ser Gly Asn Arg Pro Gly
            35                  40                  45

Asp Ala Lys Thr Thr Gly Leu Asn Glu Ala Ile Ser Ser Ile Val Asp
        50                  55                  60

Tyr Phe Thr Glu His Asp Ile Thr Asp Ala Val Leu Met Gly His Ser
65                  70                  75                  80

Tyr Gly Gly Met Val Ile Thr Gly Val Ala Asp Arg Ile Pro Gly Arg
                85                  90                  95

Ile Arg Arg Leu Ile Tyr Trp Asn Ala Phe Val Pro Asn Asp Gly Glu
            100                 105                 110

Cys Leu Asn Asp Met Val Pro Pro His Tyr Val Ala Leu Phe Asp Ala
            115                 120                 125

Val Ala Ala Glu Arg Gly Asp Gly Ser Val Val Leu Pro Phe Pro Ile
130                 135                 140

Trp Arg Glu Ala Phe Ile Asn Asp Ala Asp Leu Ala Thr Ala Thr Arg
145                 150                 155                 160

Thr Tyr Glu Ile Leu Asn Pro His Pro Asn Lys Thr Phe Thr Asp Ala
            165                 170                 175

```
Ile Lys Leu Lys Thr Asn Pro Ala Glu Met Thr Ile Ala Lys Ser Tyr
            180                 185                 190

Ile Asn Cys Thr Glu Asp Thr Ala Leu Pro His Ser Leu Pro Trp His
        195                 200                 205

Pro Arg Leu Ser Gly Lys Leu Gly Leu Phe Arg Leu Val Gln Val Pro
    210                 215                 220

Gly Ser His Glu Leu Cys Phe Ser Asp Pro Ala Arg Leu Ala Gln Ala
225                 230                 235                 240

Ile Met Asp Ala Gly Arg Asp
                245

<210> SEQ ID NO 38
<211> LENGTH: 235
<212> TYPE: PRT
<213> ORGANISM: Bacillus cereus
<220> FEATURE:
<223> OTHER INFORMATION: B4264

<400> SEQUENCE: 38

Met Ser Thr Tyr Ile Leu Val His Gly Ala Trp Gln Gly Glu Trp Ala
1               5                   10                  15

Trp Glu Leu Val Lys Pro Glu Leu Glu Ala Leu Gly His Thr Val Val
            20                  25                  30

Thr Leu Asp Leu Pro Gly Ser Gly Lys Asp Met Thr Pro Ser Gln Asn
        35                  40                  45

Ile Thr Leu Asp Ser Tyr Val Ser Ala Val Thr Glu Val Ile Asn Gln
    50                  55                  60

Gln Asn Glu Gln Val Ile Leu Val Gly His Ser Met Gly Gly Ile Ile
65                  70                  75                  80

Ile Thr Gln Thr Ala Glu Leu Ile Pro Asn Lys Ile Asp Lys Leu Val
                85                  90                  95

Tyr Leu Cys Ala Phe Leu Pro Gln Asn Gly Glu Ser Leu Gly Ser Lys
            100                 105                 110

Leu Asp Gly Glu Asp Gly Pro Gln Phe Thr Ile Asn Glu Asn Asp Leu
        115                 120                 125

Thr Ala Glu Leu Ile Pro Asn Leu Ile Glu Gln Thr Phe Leu Asn Ala
    130                 135                 140

Ile Glu Asp Glu Ala Ile Ile Glu Thr Ser Phe Lys Gln Met Arg Pro
145                 150                 155                 160

Gln Pro Leu Gly Pro Phe Gln Gln Glu Leu Lys Ile Ser Glu Glu Asn
                165                 170                 175

Phe Gly Ala Ile Asp Arg Ile Tyr Ile Glu Thr Thr Leu Asp Arg Ala
            180                 185                 190

Ile Pro Ile Asp Phe Gln Arg Arg Met Asn Thr Glu Thr Pro Cys Lys
        195                 200                 205

Lys Ile Ile Thr Leu Glu Ala Asp His Ser Pro Phe Phe Ser Lys Val
    210                 215                 220

Ser Glu Leu Val Leu Asn Leu Asn Glu Leu Ser
225                 230                 235

<210> SEQ ID NO 39
<211> LENGTH: 247
<212> TYPE: PRT
<213> ORGANISM: Burkholderia phytofirmans
<220> FEATURE:
<223> OTHER INFORMATION: PsJN

<400> SEQUENCE: 39
```

Met Glu Arg Gly Tyr Thr Phe Val Leu Val His Gly Ala Trp His Tyr
1               5                   10                  15

Gly Asp Leu Trp Ala Pro Val Ala Glu Ser Leu Arg Ile Ala Gly His
                20                  25                  30

Glu Val His Thr Pro Thr Val Ala Gly His Ala Tyr Asn Ala Gln Pro
            35                  40                  45

Gly Glu Arg Asp Val Gly His Ala Asp Gly Val Ala Ser Ile Val Glu
        50                  55                  60

Tyr Ile Arg Arg Asn Glu Leu Lys Asn Ile Val Leu Val Ala His Ser
65                  70                  75                  80

Phe Gly Gly Ser Ile Ile Ser Arg Val Ala Glu Glu Val Pro Glu Leu
                85                  90                  95

Ile Arg Arg Leu Val Tyr Trp Asn Ala Phe Val Leu Lys Asp Gly Glu
            100                 105                 110

Ser Val Ala Asp Val Ser Pro Pro Thr Tyr Asn Leu Met Met Asp Ala
        115                 120                 125

Ile Ala Glu Glu Arg Gly Asp Asn Cys Val Val Leu Pro Tyr Gln Val
    130                 135                 140

Trp Arg Asp Ser Phe Ile Gly Asp Ala Asp Glu Ala Thr Ala Arg His
145                 150                 155                 160

Thr Tyr Gly Leu Leu Cys Pro Glu Pro Tyr Arg Met Leu Thr Asp Lys
                165                 170                 175

Val Pro Leu Lys Ser Phe Asp Lys Leu Gln Ile Pro Lys Thr Tyr Leu
            180                 185                 190

Asn Ala Gln Ala Asp Val Ala Met Pro Pro Gly Gln Tyr Ala Trp Phe
        195                 200                 205

Pro Arg Phe Ala Glu Arg Leu Phe Pro Cys Arg Val Val His Met Ser
    210                 215                 220

Gly Ser His Gln Val Met Phe Ser Asn Pro Ala Gly Leu Ala Glu Lys
225                 230                 235                 240

Ile Ile Gln Ala Gly Arg Asp
                245

<210> SEQ ID NO 40
<211> LENGTH: 238
<212> TYPE: PRT
<213> ORGANISM: Mycobacterium smegmatis
<220> FEATURE:
<223> OTHER INFORMATION: str. MC2 155

<400> SEQUENCE: 40

Met Ala Asp Phe Val Ile Val His Gly Ser Trp His Asp Gly Thr Leu
1               5                   10                  15

Leu Glu Pro Val Ala Ala Ala Ile Arg Gly Leu Gly His Arg Ala Tyr
                20                  25                  30

Ala Pro Thr Val Ala Gly His Gly His Gly Ala Asp Thr Asp Val Ser
            35                  40                  45

Ile Asp Asp Gly Val Gln Ser Val Ile Asp Tyr Cys Arg Thr Arg Asp
        50                  55                  60

Leu Arg Glu Ile Val Leu Val Gly His Ser Leu Gly Gly Thr Ile Ile
65                  70                  75                  80

Ala Arg Val Ala Glu Glu Ile Pro Asp Arg Ile Thr Arg Leu Ile Phe
                85                  90                  95

Trp Ser Ala Phe Val Pro Arg Pro Gly Arg Ser Ile Thr Glu Glu Val
            100                 105                 110

Glu Gln Pro Ser Thr Pro Ala Ala Glu Lys Gln Ala Pro Ala Thr Gly 115                 120                 125
Ser Ser Glu Thr Leu Ser Leu Gln Val Trp Arg Asp Val Phe Val Pro
130                 135                 140

Asp Val Asp Pro Glu Gln Ala Ala Thr Trp His Ala Leu Leu Ser Pro
145                 150                 155                 160

Glu Pro Arg Arg Pro Lys Thr Glu Arg Leu Asp Leu Arg Arg Phe Tyr
                165                 170                 175

Arg Ser Thr Leu Pro Met His Tyr Ile Asp Ala Val Asp Asp Arg Ala
                180                 185                 190

Leu Pro Arg Gly Leu Asp Arg Glu Ala Met Ile Glu Arg Leu Lys Asn
                195                 200                 205

Val Arg Val His Arg Val Arg Gly Gly His Glu Val Leu Phe Thr Asp
                210                 215                 220

Pro Ala Gly Ile Ala Ala Val Ile Val Glu Ala Gly Val Ser
225                 230                 235

<210> SEQ ID NO 41
<211> LENGTH: 239
<212> TYPE: PRT
<213> ORGANISM: Acinetobacter sp.
<220> FEATURE:
<223> OTHER INFORMATION: ADP1

<400> SEQUENCE: 41

Met Ile Thr Tyr Val Leu Val His Gly Ser Trp His Asp Gly Ser Leu
1               5                   10                  15

Trp Glu Pro Val Ala Thr His Leu Arg Ala Gln Gly His Thr Val His
                20                  25                  30

Cys Pro Thr Val Ala Gly His Gly Pro Asn Ala Asp Arg Asn Val Thr
                35                  40                  45

His Ala Gln Cys Ser Gln Ser Ile Ala Asp Tyr Ile Val Lys His Asp
                50                  55                  60

Leu Ser Glu Ile Val Leu Leu Gly His Ser Tyr Gly Gly Thr Ile Ile
65                  70                  75                  80

Ser Lys Val Ala Glu Ala Ile Pro Glu Arg Ile Gln Arg Leu Ile Tyr
                85                  90                  95

Trp Asn Ala Phe Val Leu Gln Asp Gly Glu Asn Met Phe Asp Asn Met
                100                 105                 110

Pro Glu Ala Tyr Tyr Glu Leu Phe Thr Ser Leu Ala Ala Ala Ser Gly
                115                 120                 125

Asp Asn Thr Val Leu Leu Pro Tyr Glu Val Trp Arg His Ala Phe Ile
130                 135                 140

Asn Asp Ala Asp Asp Gln Met Ala Glu Glu Thr Tyr Lys Met Leu Thr
145                 150                 155                 160

Pro Glu Pro Cys Gln Pro Phe His Asp Arg Leu Asp Leu Lys Lys Phe
                165                 170                 175

Tyr Thr Leu Asn Ile Pro Lys Ser Tyr Leu Asn Cys Thr Glu Asp Gln
                180                 185                 190

Ala Leu Pro Ala Gly Phe Trp His Pro Lys Met Ser Asn Arg Leu Gly
                195                 200                 205

Glu Phe Lys Leu Val Glu Met Gly Gly Ser His Glu Ala Met Phe Thr
                210                 215                 220

Arg Pro Gln Glu Leu Ala Thr Lys Ile Ile Glu Ala Ser His Asp
225                 230                 235

<210> SEQ ID NO 42

<211> LENGTH: 237
<212> TYPE: PRT
<213> ORGANISM: Rhodobacterales bacterium
<220> FEATURE:
<223> OTHER INFORMATION: HTCC2654

<400> SEQUENCE: 42

```
Met Ala His Phe Leu Leu Val His Gly Ser Asn His Gly Ala Trp Cys
1               5                   10                  15

Trp Arg Asp Val Val Pro Glu Leu Glu Ala Arg Gly His Thr Ala Thr
            20                  25                  30

Ala Leu Asp Leu Pro Ser His Gly Ala Asp Lys Thr Pro Ile Ala Glu
        35                  40                  45

Val Thr Leu Asp Ala Tyr Ala Asp Lys Ile Leu Ala Ala Leu Asp Gly
    50                  55                  60

Pro Thr Ile Leu Val Gly His Ser Ala Gly Gly Tyr Ala Ile Thr Gln
65                  70                  75                  80

Ala Ala Glu Arg Asp Pro Thr Asn Val Ala Gly Leu Val Phe Leu Thr
                85                  90                  95

Ala Tyr Val Pro Gln Pro Gly Lys Ser Leu Val Asp Met Leu Gly Glu
            100                 105                 110

Ala Pro Glu Gln Pro Met Lys Gly Ala Phe Asp Met Ala Pro Asp Lys
        115                 120                 125

Lys Ser Phe Arg Phe Lys Pro Glu Phe Leu Thr Arg Ala Leu Tyr Gly
130                 135                 140

Asp Cys Pro Glu Gly Thr Tyr Asp Tyr Ala Met Ala His Ile Gly Trp
145                 150                 155                 160

Gln Pro Leu Ser Thr Gln Thr Val Pro Ala Thr Leu Thr Gly Ala Ser
                165                 170                 175

Asp Thr Val Pro Arg Arg Tyr Ile Phe Cys Thr Glu Asp Arg Ala Ile
            180                 185                 190

Pro Leu Ala His Gln Lys Gln Met Ala Ala Gly Phe Ser Ala Asp Glu
        195                 200                 205

Thr Phe Asp Leu Ala Thr Gly His Ser Pro Phe Phe Ser Ala Pro Gly
    210                 215                 220

Pro Leu Ala Asp Ile Leu Asp Arg Ile Ala Asn Ala Thr
225                 230                 235
```

<210> SEQ ID NO 43
<211> LENGTH: 237
<212> TYPE: PRT
<213> ORGANISM: Silicibacter pomeroyi
<220> FEATURE:
<223> OTHER INFORMATION: DSS-3

<400> SEQUENCE: 43

```
Met Ala Asp Phe Leu Leu Ile His Gly Ser Cys His Gly Ala Trp Cys
1               5                   10                  15

Trp Arg Asp Leu Ile Pro Ala Leu Glu Glu Arg Gly His Thr Ala Arg
            20                  25                  30

Ala Val Asn Met Pro Ser His Gly Ser Asp Val Thr Pro Ile Gly Glu
        35                  40                  45

Val Thr Leu Asn Ser Cys Arg Asp Ala Val Leu Gly Ala Ser Thr Pro
    50                  55                  60

Asp Thr Leu Ile Val Gly His Ser Trp Gly Gly Tyr Pro Ile Ser Ala
65                  70                  75                  80

Ala Ala Glu Gln Ala Pro Asp Ala Met Arg Gly Leu Ile Tyr Leu Cys
                85                  90                  95
```

-continued

```
Ala Tyr Val Pro Leu Ser Gly His Ser Met Ile Asp Met Arg Lys Arg
            100                 105                 110

Ala Pro Arg Gln Thr Leu Leu Asp Ala Val Ile Lys Ser Glu Asp Gly
            115                 120                 125

Leu Ser Tyr Thr Val Asp Pro Glu Arg Val Ala Asp Leu Phe Tyr His
        130                 135                 140

Asp Cys Arg Ala Glu Arg Val His Tyr Ala Gln Pro Arg Leu Cys Pro
145                 150                 155                 160

Gln Ala Ile Ala Pro Gln Glu Thr Pro Leu Thr Leu Ser Asp Arg Phe
                165                 170                 175

Ala Ser Val Pro Lys Val Tyr Ile Arg Cys Ala Glu Asp Arg Thr Ile
            180                 185                 190

Pro Pro Glu Tyr Gln Glu Glu Met Thr Ala Asp Trp Pro Ser Asp Arg
            195                 200                 205

Val His Val Met Asn Ser Ser His Ser Pro Phe Phe Ala Asp Pro Gln
        210                 215                 220

Gly Leu Ala Arg Leu Leu Thr Arg Ile Glu Gly Gln Phe
225                 230                 235
```